United States Patent
Dong et al.

(10) Patent No.: US 11,091,442 B2
(45) Date of Patent: Aug. 17, 2021

(54) FLUOROSULFONYL-CONTAINING COMPOUND, INTERMEDIATE THEREOF, PREPARATION METHOD THEREFOR AND USE THEREOF

(71) Applicant: SHANGHAI INSTITUTE OF ORGANIC CHEMISTRY, CHINESE ACADEMY OF SCIENCES, Shanghai (CN)

(72) Inventors: Jiajia Dong, Shanghai (CN); Qian Yang, Shanghai (CN); Taijie Guo, Shanghai (CN); Xiongjie Zhan, Shanghai (CN); Genyi Meng, Shanghai (CN)

(73) Assignee: SHANGHAI INSTITUTE OF ORGANIC CHEMISTRY, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 16/766,193

(22) PCT Filed: Nov. 22, 2018

(86) PCT No.: PCT/CN2018/116922
§ 371 (c)(1),
(2) Date: May 21, 2020

(87) PCT Pub. No.: WO2019/101132
PCT Pub. Date: May 31, 2019

(65) Prior Publication Data
US 2020/0369619 A1  Nov. 26, 2020

(30) Foreign Application Priority Data
Nov. 22, 2017  (CN) .......................... 201711176351.8
Jun. 13, 2018  (CN) .......................... 201810609858.6

(51) Int. Cl.
*C07D 233/56*  (2006.01)
*C07D 235/08*  (2006.01)

(52) U.S. Cl.
CPC ......... *C07D 233/56* (2013.01); *C07D 235/08* (2013.01)

(58) Field of Classification Search
CPC ................................................... C07D 233/56
See application file for complete search history.

(56) References Cited

FOREIGN PATENT DOCUMENTS

| CN | 107857730 A | 3/2018 |
| CN | 110590609 A | 12/2019 |
| WO | 2015188120 A1 | 12/2015 |
| WO | 2018157240 A1 | 9/2018 |

OTHER PUBLICATIONS

Nov. 22, 2018 International Search Report issued in International Patent Application No. PCT/CN2018/116922.
Nov. 22, 2018 Written Opinion of the International Searching Authority issued in International Patent Application No. PCT/CN2018/116922.
K.Barry Sharpless, Jiajia Dong-Sulfur (VI) Fluoride Exchange (SuFEx): Another Good Reaction for Click Chemistry-Angewandte Chemie international Edition (vol. 53, ISSN:1433-7851, p. 9430-9448)—Aug. 11, 2014.
Guo, Taijie et al., A New Portal to SuFEx Click Chemistry: A Stable Fluorosulfuryl Imidazolium Salt Emerging as an "F-SO2+" Donor of Unprecedented Reactivity, Selectivity, and Scope Angewandte Chemie, International Edition (No. 10 vol. 57, ISSN:1433-7851 p. 2605-2610, Figure 1 and Figure 2 on p. 2606)—Feb. 1, 2018.
Dey, Soumyadeb et al.,—Quantification of Aromaticity of Heterocyclic Systems using Interaction Coordinates—Journal of Physical Chemistry A (No. 34, vol. 122, ISSN:1089-5639 p. 6953-6960, entry 8 in Table 5 on p. 6958)—Aug. 3, 2018.
Curutchet, Carles et al., Analysis of the Effects of N-Substituents on Some Aspects of the Aromaticity of imidazoles and Pyrazoles—Journal of Physical Chemistry A (No. 30 vol. 115 ISSN:1089-56396 p. 8571-8577, Table 1 and Scheme 1 on p. 8573)—Jun. 30, 2011.
Extended European Search Report dated Jun. 4, 2021 issued in corresponding European Patent Application No. 18880337.3, 6 pages.
First Office Action dated Jun. 15, 2021 issued in corresponding Chinese Patent Application No. 201810609858.6, with English translation, 25 pages.

*Primary Examiner* — Shawquia Jackson
(74) *Attorney, Agent, or Firm* — Foley & Lardner LLP

(57) ABSTRACT

Disclosed in the present invention were a fluorosulfonyl-containing compound, an intermediate thereof, a preparation method therefor and use thereof. The fluorosulfonyl-containing compound disclosed in the present invention comprises a cation and an anion, the cation being as shown in Formula (1). The fluorosulfonyl-containing compound of the present invention can react with a substrate to efficiently synthesize a fluorosulfonylation product, has low toxicity, was simple to prepare, was convenient to use, and was in a solid stable state at normal temperature. Furthermore, the compound has a wide range of adaptable substrates, including phenolic compounds and amine compounds, and was the only solid form agent that can achieve such a chemical conversion, and therefore has important academic and application value.

(1)

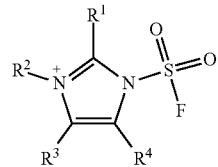

20 Claims, 1 Drawing Sheet

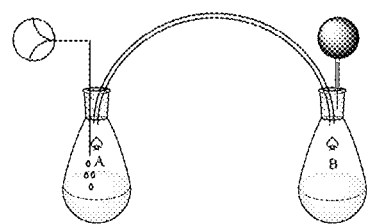

FLUOROSULFONYL-CONTAINING COMPOUND, INTERMEDIATE THEREOF, PREPARATION METHOD THEREFOR AND USE THEREOF

This application is a 371 of PCT/CN2018/116922, filed Nov. 22, 2018, which claims the benefits of Chinese patent application CN201711176351.8 filed on Nov. 22, 2017 and Chinese patent application CN201810609858.6 filed on Jun. 13, 2018. The contents of these Chinese patent applications are incorporated herein by reference in their entireties.

FIELD OF THE INVENTION

The present disclosure relates to a fluorosulfonyl-containing compound, an intermediate, preparation method and use thereof

BACKGROUND OF THE INVENTION

The high-valency fluorides of main group elements have high chemical stability, but their activation under specific conditions can realize extremely efficient chemical bond conversion and linkage. This unique stability-reactivity combination pattern determines that these compounds would have unique potential applications in organic synthesis chemistry, material chemistry, chemical biology and pharmaceutical chemistry. The success of the Sulfur (VI) Fluoride Exchange (SuFEx) is precisely due to the special reactivity of the hexavalent sulfur-fluorine bond. Since Professor K. Barry Sharpless and Professor Jiajia Dong first proposed and successfully implemented the Sulfur (VI) Fluoride Exchange in 2014 (*Angew. Chem. Int. Ed.* 2014, 9430), this type of reaction has attracted extensive attention and has shown a good application prospect in organic synthesis chemistry, material chemistry, pharmaceutical chemistry and chemical biology, especially in selective labeling and modification of protein molecules and other fields, and it is called a new generation of click chemistry, triggering a new hot spot in fluorine chemistry research at present. Among a series of hexavalent sulfur fluoride functional groups that can be widely used, fluorosulfonyl functional group is the most widely used. According to the types of atoms directly linked with the sulfur atom, the functional groups can be further subdivided into: fluorosulfonyl groups (C—SO$_2$F, Sulfonyl Fluoride, the sulfur atom is directly linked with a carbon atom in the molecule), and (fluorosulfonyl)oxy groups (O—SO$_2$F, fluorosulfate, the sulfur atom is directly linked with an oxygen atom in the molecule); and N-fluorosulfonyl groups (N—SO$_2$F, Sulfamoyl Fluoride, the sulfur atom is directly linked with a nitrogen atom in the molecule). The systematic synthesis of these series of functional groups is systematically discussed in articles on the Sulfur (VI) Fluoride Exchange (*Angew. Chem. Int. Ed.* 2014, 9430).

In the above literature, Dong and Sharpless employ a gas called sulfinyl fluoride (SO$_2$F$_2$, a large-scale industrial fumigant, sulfuryl fluoride, trade name: Vikane) to realize the direct conversion of phenolic compounds (ArOH, Ar=aryl) to fluorosulfonate groups (ArO—SO$_2$F), and the direct conversion of secondary amine compounds (R$_x$R$_y$NH) to sulfamoyl fluorides (RxRyN-SO$_2$F, Sulfamoyl fluoride). This is the best way to synthesize these two classes of functional groups among those having been reported in literature currently. Although sulfuryl fluoride can be efficient for synthesizing these two classes of compounds with —OSO$_2$F and —NSO$_2$F, the use of sulfuryl fluoride to synthesize these series of compounds in the laboratory also has extremely obvious drawbacks: this compound is a fumigant gas with certain toxicity; and it is difficult to give the gas in many countries worldwide, including areas with developed chemical industry, such as Europe, the United States, Japan, and many areas with underdeveloped chemical industry due to control; moreover, most of the laboratories that need to use this type of fluorosulfonyl-containing compounds are chemical biology and material chemistry laboratories, and it is difficult for these non-professional synthetic chemistry laboratories to use this type of compounds.

CONTENT OF THE INVENTION

The present disclosure aims to overcome the drawback of the existing fluorosulfonylating reagents in the field, e.g., high toxicity, incapability of popularization and application, difficulty in preparation, thus providing a fluorosulfonyl-containing compound, an intermediate, preparation method and use thereof. The fluorosulfonyl-containing compound can be efficient for synthesizing fluorosulfonyl-containing products, and has low toxicity, synthetic simplicity and use convenience. In addition, the compound is in stable solid state at normal temperature and is applicable for an extremely wide range of substrates, and it is the only solid form reagent capable of realizing this type of chemical conversion at present, thus having favourable academic and application values.

The present disclosure solves the above problem through the following technical solutions.

The present disclosure provides a fluorosulfonyl-containing compound comprising a cation and an anion, the cation is as shown in formula 1:

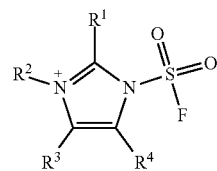

wherein each of R$^1$, R$^2$, R$^3$ and R$^4$ is independently H or C$_{1-6}$ alkyl, or R$^3$ and R$^4$ together with the carbon atoms between them form unsaturated C$_5$-C$_8$ cyclohydrocarbyl.

In a certain embodiment, when R$^3$ and R$^4$ together with the carbon atoms between them form unsaturated C$_5$-C$_8$ cyclohydrocarbyl, then the "unsaturated C$_5$-C$_8$ cyclohydrocarbyl" is benzene ring.

In a certain embodiment, the fluorosulfonyl-containing compound consists of the cation and the anion.

In a certain embodiment, when R$^1$ is C$_{1-6}$ alkyl, then the C$_{1-6}$ alkyl is C$_{1-4}$ alkyl (e.g., methyl, ethyl, isopropyl or butyl (e.g., n-butyl, sec-butyl, isobutyl or tert-butyl), or e.g., methyl or butyl (e.g., n-butyl)).

In a certain embodiment, when R$^2$ is C$_{1-6}$ alkyl, then the C$_{1-6}$ alkyl is C$_{1-4}$ alkyl (e.g., methyl or butyl (e.g., n-butyl, sec-butyl, isobutyl or tert-butyl, or e.g., n-butyl)).

In a certain embodiment, when R$^3$ is C$_{1-6}$ alkyl, then the C$_{1-6}$ alkyl is C$_{1-4}$ alkyl (e.g., methyl or butyl (e.g., n-butyl, sec-butyl, isobutyl or tert-butyl, or e.g., n-butyl)).

In a certain embodiment, when R$^4$ is C$_{1-6}$ alkyl, then the C$_{1-6}$ alkyl is C$_{1-4}$ alkyl (e.g., methyl or butyl (e.g., n-butyl, sec-butyl, isobutyl or tert-butyl, or e.g., n-butyl)).

In a certain embodiment, $R^4$ is H, $R^3$ is H or $C_{1-6}$ alkyl.

In a certain embodiment, each of $R^1$ and $R^2$ is independently H or $C_{1-6}$ alkyl, $R^4$ is H, $R^3$ is H or $C_{1-6}$ alkyl, or, $R^3$ and $R^4$ together with the carbon atoms between them form benzene ring.

In a certain embodiment the anion can be a conventional anion in the field, preferably $^-R^5$, wherein $R^5$ can be

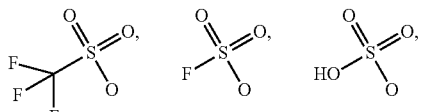

$BF_4$ or $PF_6$.

In a certain embodiment, $R^5$ is

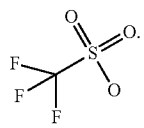

In a certain embodiment, the cation is

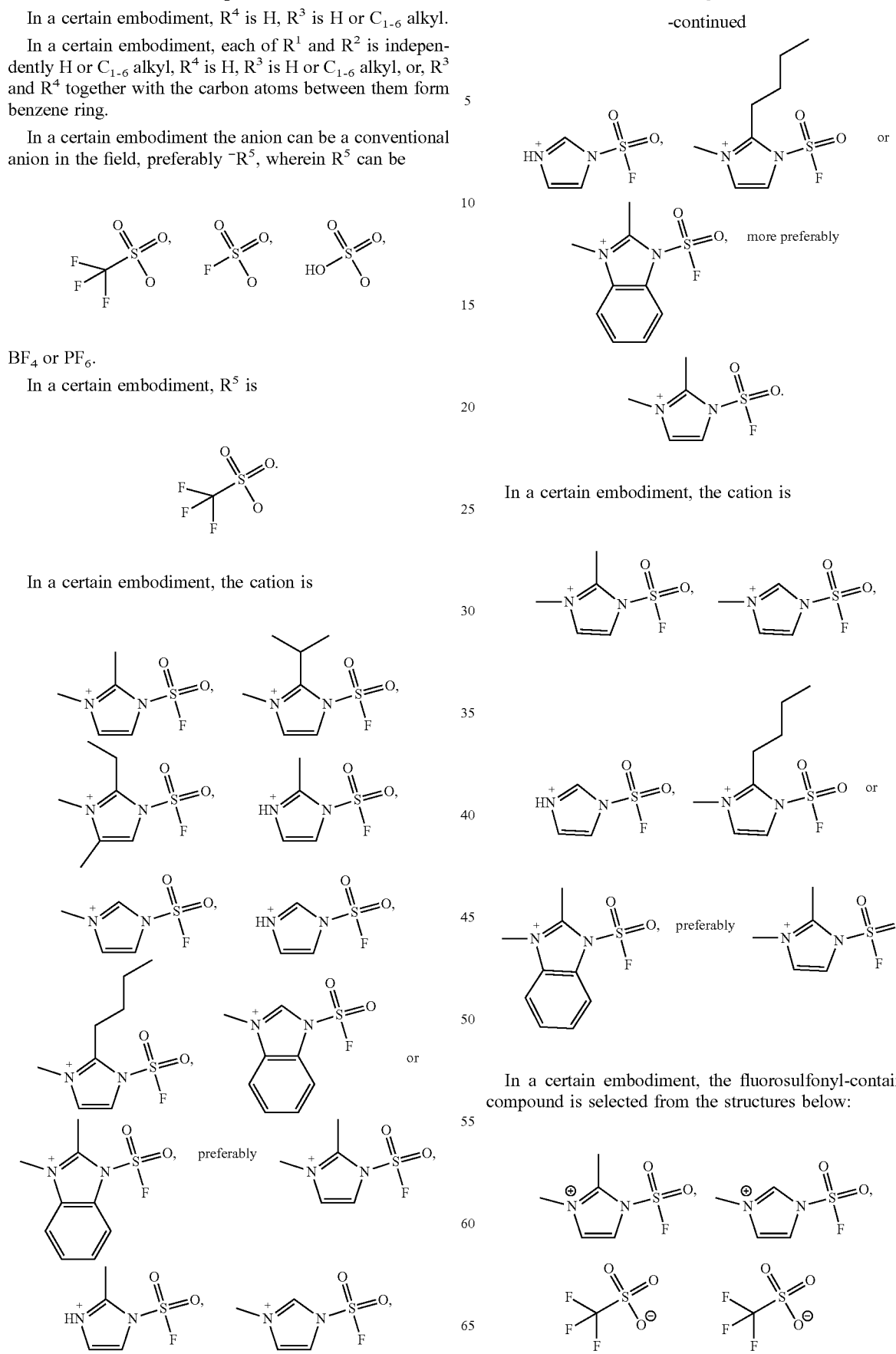

In a certain embodiment, the fluorosulfonyl-containing compound is selected from the structures below:

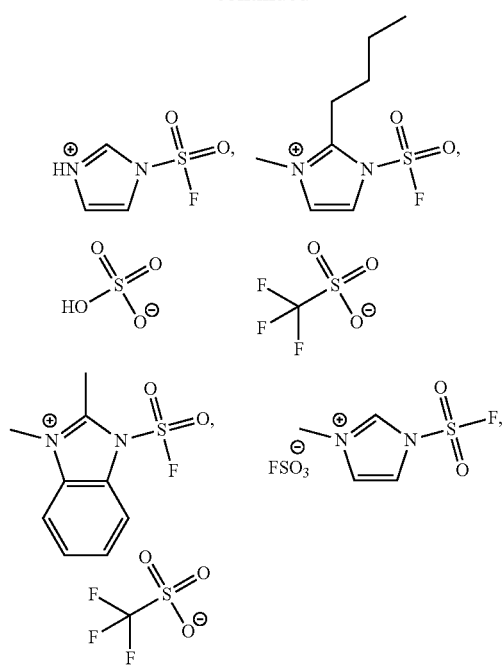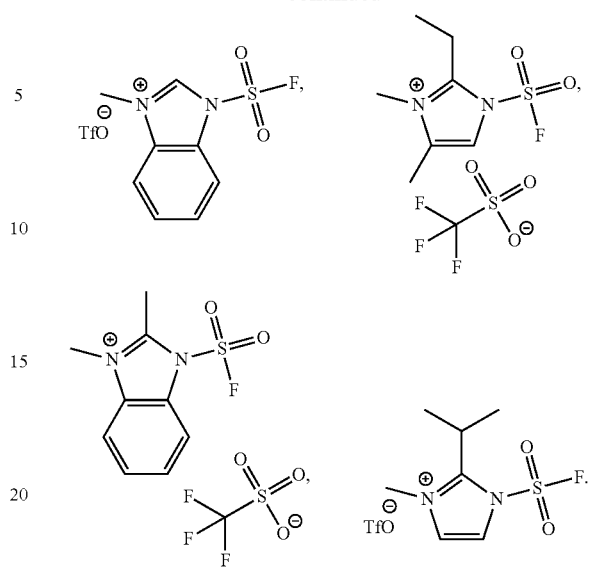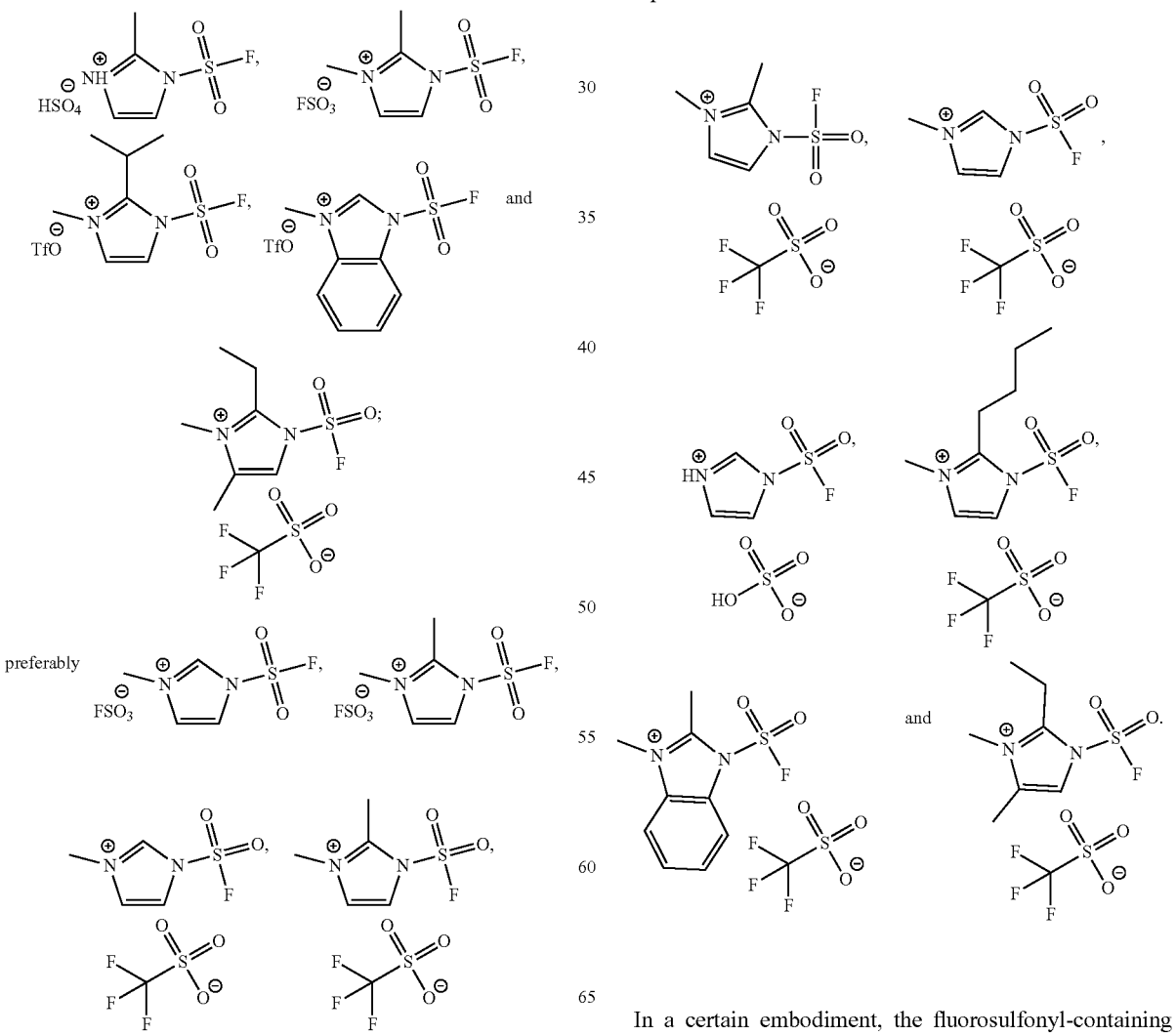
In a certain embodiment, the fluorosulfonyl-containing compound is selected from the structures below:
In a certain embodiment, the fluorosulfonyl-containing compound is selected from the structures below:

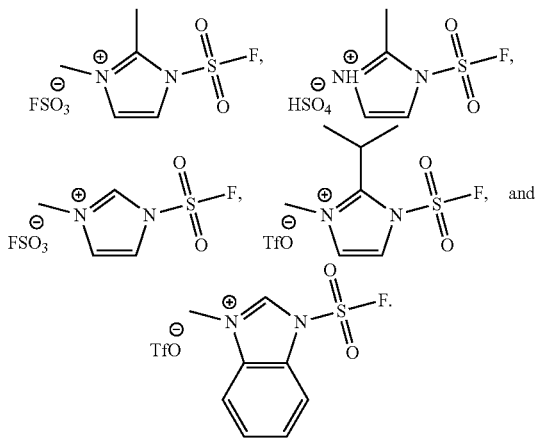

The present disclosure also provides a method for preparing the fluorosulfonyl-containing compound, wherein the method comprises the following step:

reacting the compound represented by formula 2 with "$R^2$-anion" in a first organic solvent;

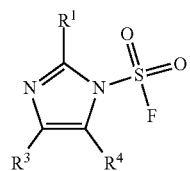

2 wherein $R^1$, $R^2$, $R^3$, $R^4$ and the anion in the fluorosulfonyl-containing compound is as defined above.

Wherein, in the structure of "$R^2$-anion", the "anion" is actually a free radical, which is called "anion" herein in order to correspond to the anion in the compound represented by formula 1 above, and can be $R^5$; in the reaction, $R^2$ is linked to the N in the compound represented by formula 2, forming the cation represented by formula 1; and $R^5$ forms the anion $^-R^5$.

The present disclosure also provides a method for preparing the fluorosulfonyl-containing compound, wherein the method comprises the following step:

reacting a compound represented by formula 2 with $R^2$-anion in a first organic solvent;

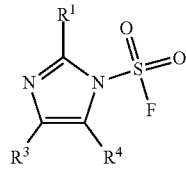

wherein $R^1$, $R^2$, $R^3$ and $R^4$ are as defined above.

Wherein, in the structure of $R^2$-anion, the anion can be $R^5$; in the reaction, $R^2$ is linked to N to form the cation; and $R^5$ forms the anion $^-R^5$.

Where in the structure of $R^2$-anion, e.g., when $R^2$ is methyl, then the structure of $R^2$-anion can be

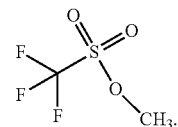

The conditions for each reaction of the method for preparing the fluorosulfonyl-containing compound can be conventional reaction conditions in the field, the present disclosure especially selects the following conditions:

wherein, the first organic solvent is preferably one or more selected from acetonitrile, dichloromethane, diethyl ether, tetrahydrofuran, 1,2-dichloroethane, dimethyl sulfoxide (DMSO), N,N-dimethylformamide, methyl tert-butyl ether (MTBE) and chloroform, preferably methyl tert-butyl ether (MTBE).

Wherein, the reaction temperature can be (−15) ° C.-20° C., preferably 0° C.

Wherein, the progress of the reaction can be monitored by TLC or HPLC, generally the disappearance of

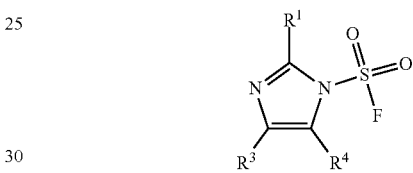

or $R^2$-$R^5$ is regarded as the endpoint of the reaction. The reaction time can be 0.5-8 hours, preferably 1-4 hours.

Wherein, the reaction can further comprise a post-treatment step, wherein the post-treatment step can comprise the following operations: concentrating, washing, and removing the solvent. The concentrating can be performed by rotary evaporation, the washing can be performed with methyl tert-butyl ether, e.g., washing three times; the solvent for the washing can be directly poured out after solid precipitation, and the residual solvent can be removed by suction with an oil pump.

Wherein, the reaction further comprises the following step:

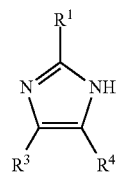

reacted with sulfuryl fluoride ($SO_2F_2$) in the presence of a base in a second organic solvent to give the

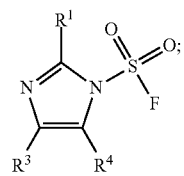

wherein $R^1$, $R^3$ and $R^4$ are as defined above.

As for the reaction for preparing

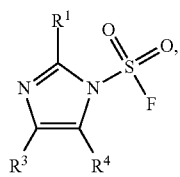

wherein, the second organic solvent can be a commonly used organic solvent in the field, one or more selected from acetonitrile, dichloromethane, ethyl acetate, benzene, toluene, acetone, 1,4-dioxane, diethyl ether, tetrahydrofuran, 1,2-dichloroethane, dimethyl sulfoxide (DMSO), N,N-dimethylformamide, N-methylpyrolidone, methyl tert-butyl ether (MTBE) and chloroform, preferably acetonitrile.

Wherein, the base can be a conventional base in the art, and can be an inorganic base (e.g., one or more selected from sodium carbonate, potassium carbonate, cesium carbonate, sodium hydroxide, potassium hydroxide, sodium bicarbonate and potassium bicarbonate; preferably sodium carbonate) and/or an organic base (e.g., one or more selected from triethylamine, N,N-diisopropylethylamine, pyrrole and pyridine; preferably triethylamine).

Wherein, the reaction can be performed at (−20) ° C.-35° C., preferably at room temperature.

Wherein, the progress of the reaction can be monitored by TLC or HPLC, generally the disappearance of

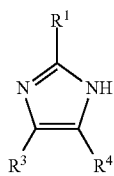

or $R^2$-$R^5$ is regarded as the endpoint of the reaction. The reaction time can be 0.5-48 hours, preferably 1-24 hours, e.g., 2-16 hours.

Wherein the sulfuryl fluoride is in a gas state; the method for introducing the sulfuryl fluoride is not particularly limited and can be a conventional gas introduction method in the art, e.g., generating negative pressure in the reaction system by suction with a water pump and then introducing the sulfuryl fluoride gas from a balloon.

The reaction also comprises a post-treatment step, wherein the post-treatment comprises the following operations: filtering, washing the filter cake, first washing, extracting, second washing, drying, filtering and concentrating. The washing the filter cake can be performed with dichloromethane or ethyl acetate; the first washing can be performed with water; the extraction can be performed with dichloromethane or ethyl acetate; the second washing can be performed with saturated brine: the drying can be performed with anhydrous sodium sulfate or anhydrous magnesium sulfate.

The present disclosure also provides a use of the fluorosulfonyl-containing compound as a fluorosulfonylating reagent.

The use as a fluorosulfonylating reagent can comprise reacting a substrate with the fluorosulfonyl-containing compound: wherein the substrate is a phenolic hydroxyl-containing compound, a primary amine or a secondary amine.

The use as a fluorosulfonylating reagent, wherein the number of phenolic hydroxyl in the phenolic hydroxyl-containing compound can be one, two or three.

The use as a fluorosulfonylating reagent, wherein when the substrate is a phenolic hydroxyl-containing compound, then the product obtained by the reaction can be selected from the following compounds:

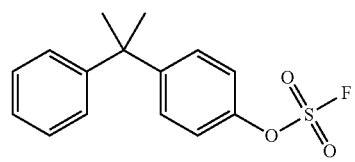
33

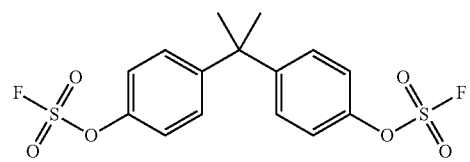
35

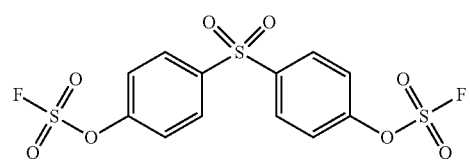
37

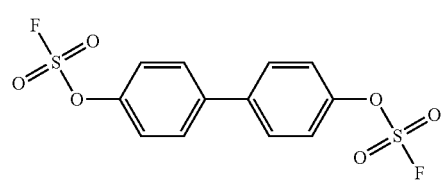
39

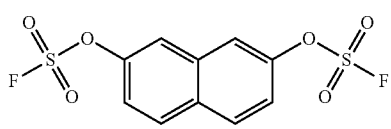
41

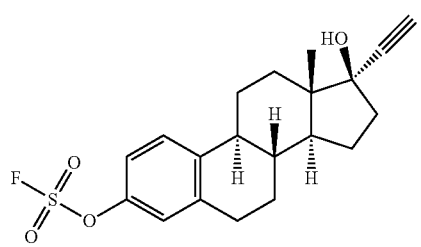
43

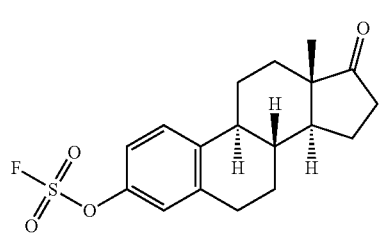
45

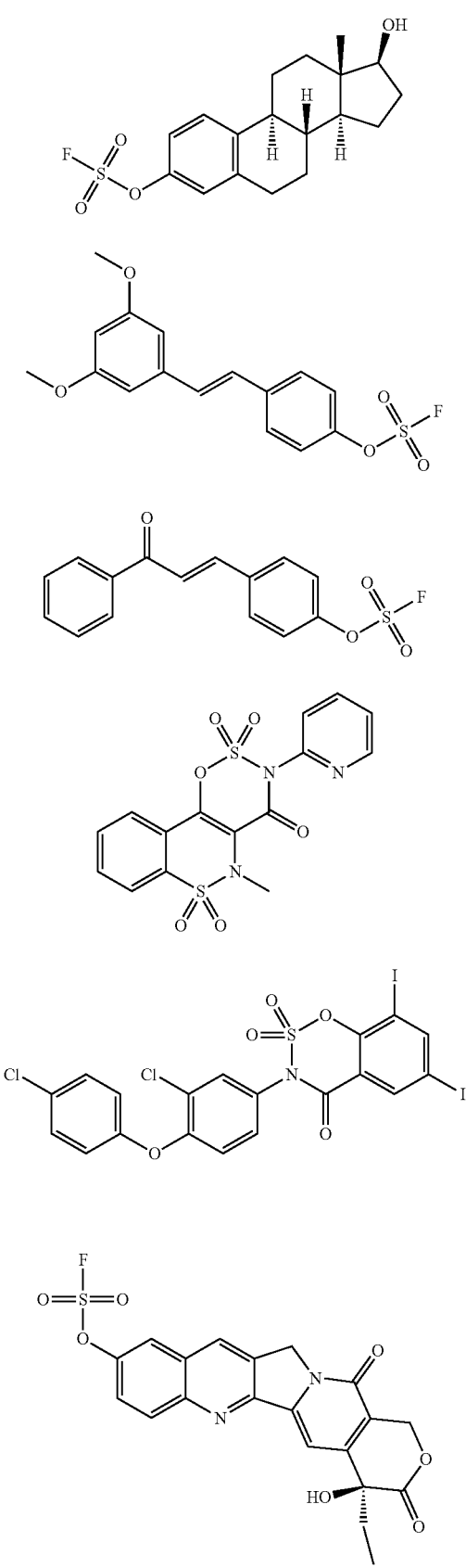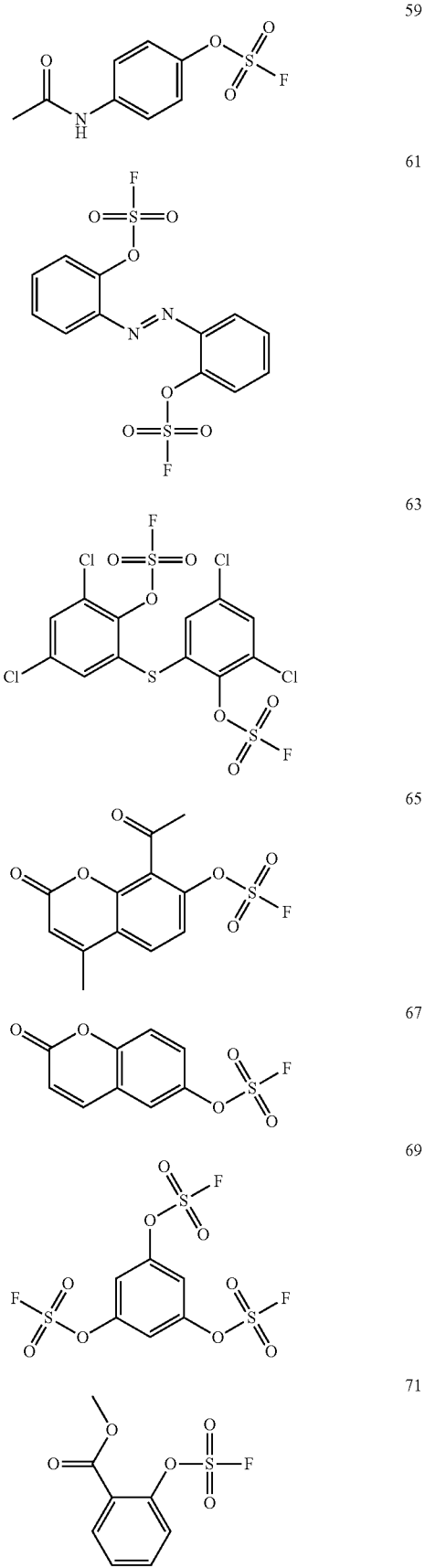

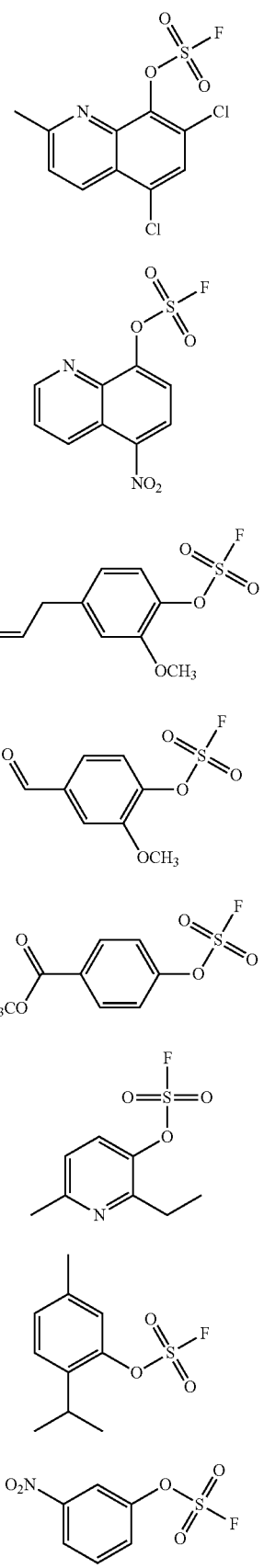
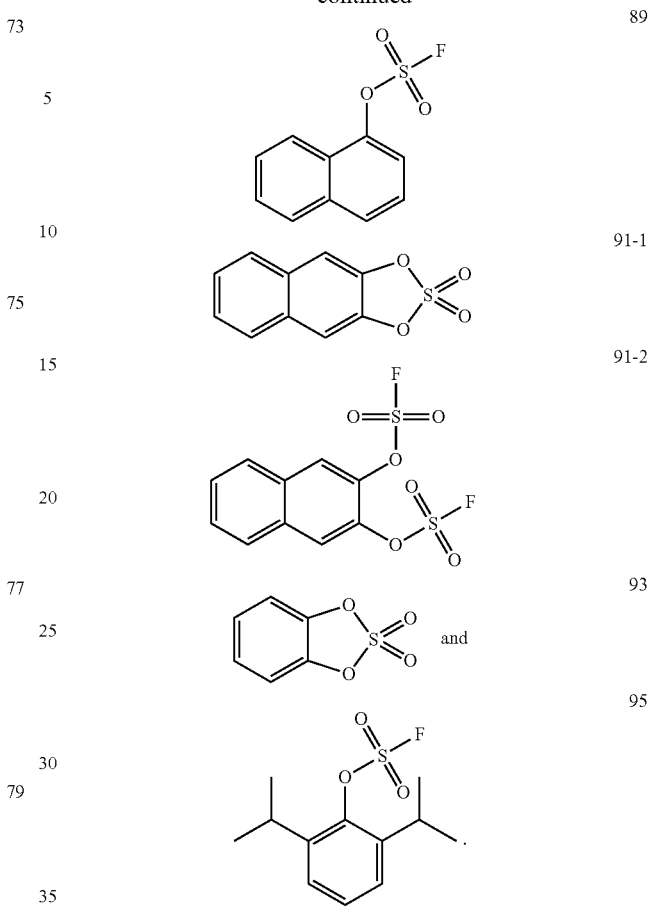
The use as a fluorosulfonylating reagent, wherein when the substrate is a primary amine, then the product obtained by the reaction can be selected from the following compounds:
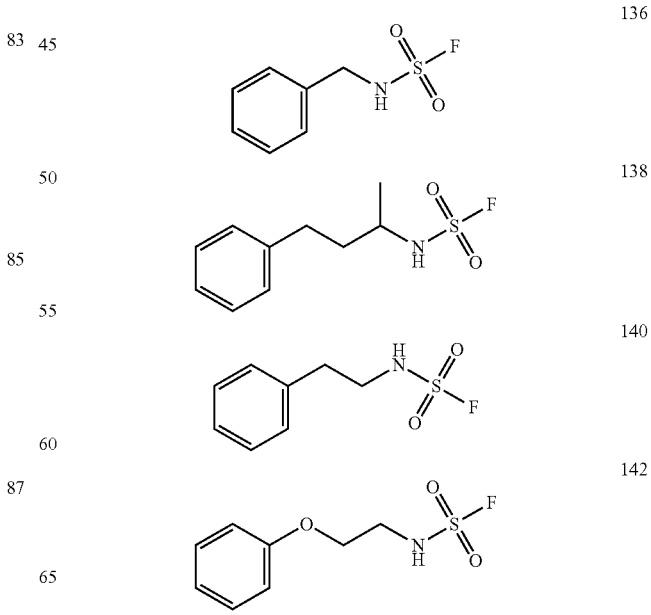

| | |
|---|---|
| 144 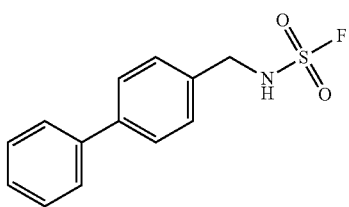 | 164 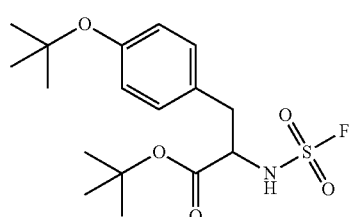 |
| 146 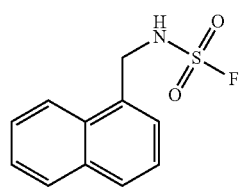 | 166 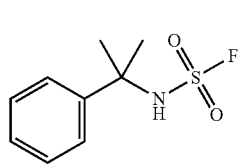 |
| 148 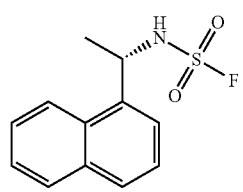 | 168 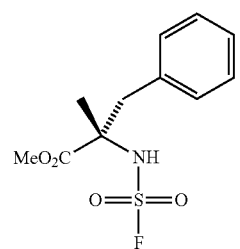 |
| 150 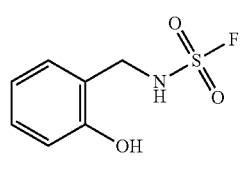 | 170 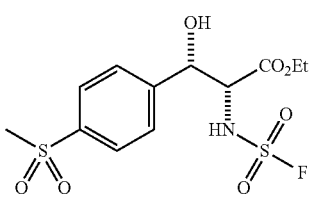 |
| 152 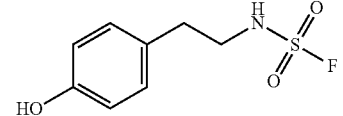 | 172 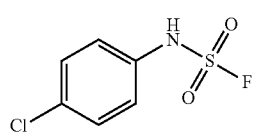 |
| 154 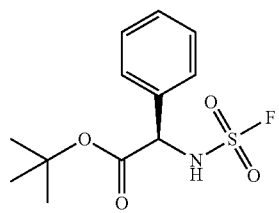 | 174 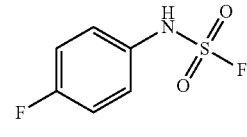 |
| 156 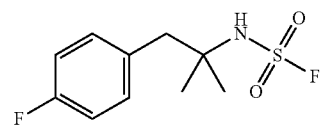 | 176 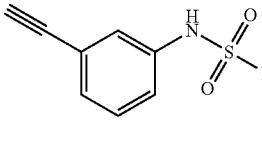 |
| 158 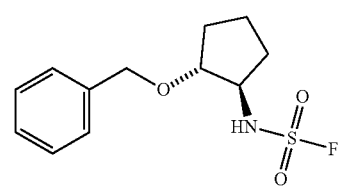 | 178 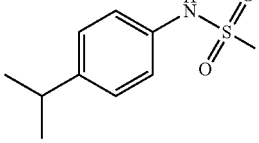 |
| 161 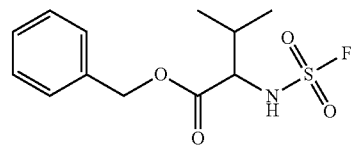 | 180 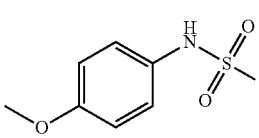 |

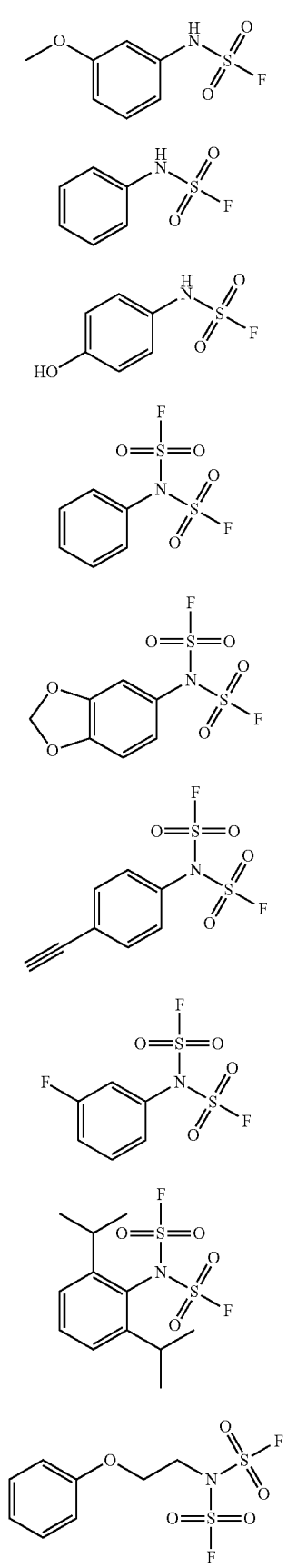
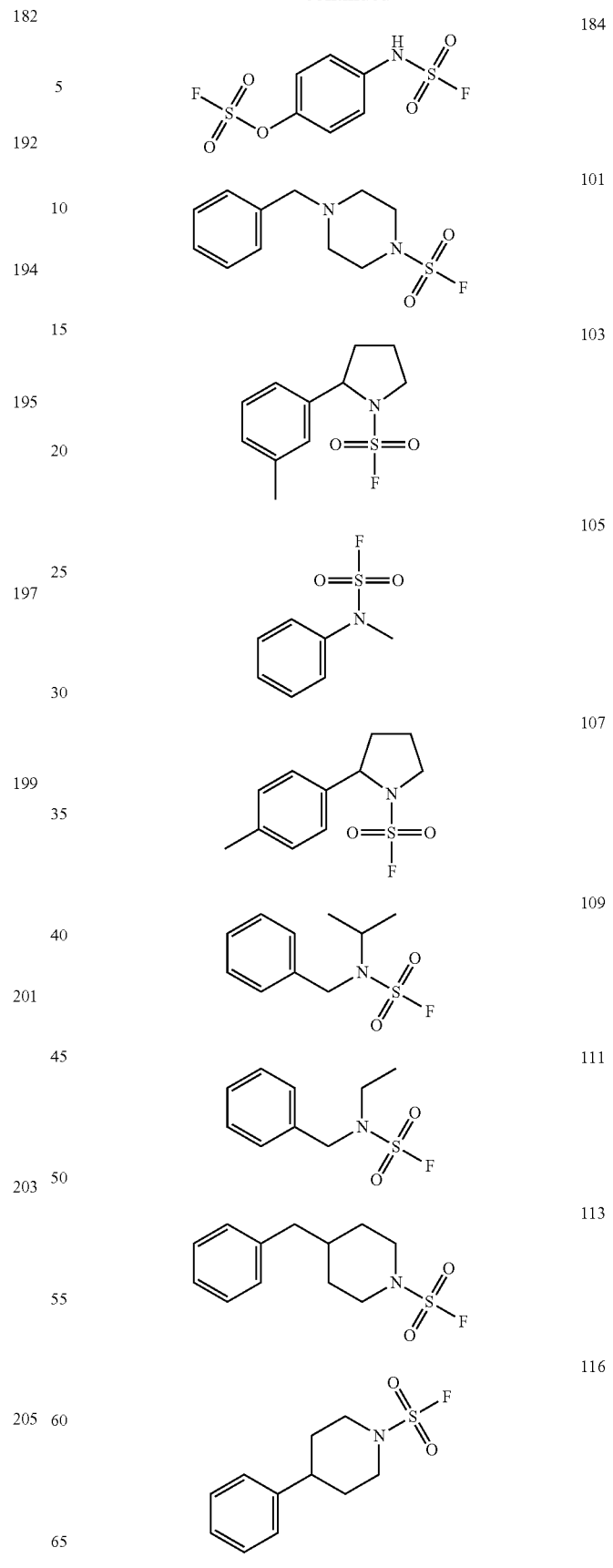

-continued

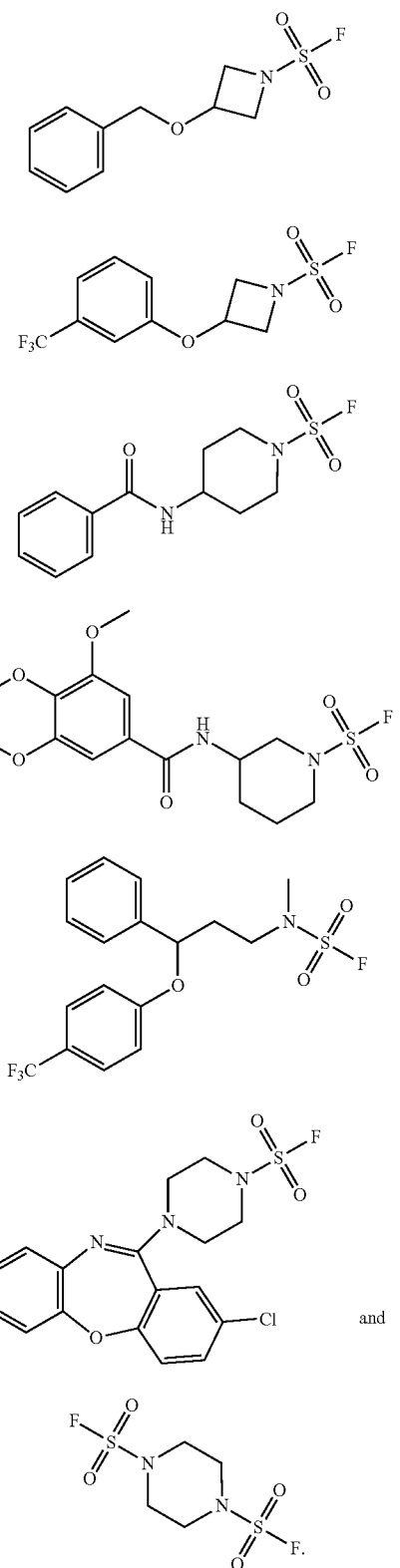

The use as a fluorosulfonylating reagent, wherein the reaction of the substrate and the fluorosulfonyl-containing compound can be carried out at 0-35° C., preferably at room temperature.

The use as a fluorosulfonylating reagent, wherein the reaction time of the substrate and the fluorosulfonyl-containing compound can be 5 min-6 h, preferably 10 min-4 h, more preferably 1 h or 2 h.

The use as a fluorosulfonylating reagent, wherein the reaction of the substrate and the fluorosulfonyl-containing compound can be carried out in an organic solvent, and the organic solvent can be a conventional organic solvent for this type of reaction, preferably acetonitrile, dichloromethane or ethyl acetate.

The use as a fluorosulfonylating reagent, wherein the progress of the reaction of the substrate and the fluorosulfonyl-containing compound can be monitored by LC-MS or GC-MS, and generally the disappearance of a substrate is regarded as the endpoint of the reaction.

The use as a fluorosulfonylating reagent, wherein the reaction of the substrate and the fluorosulfonyl-containing compound can also comprise a post-treatment step, wherein the post-treatment step can comprise the following operations: adding water to terminate the reaction, extracting, washing, drying, filtering, concentrating and removing the solvent. The extracting can be performed with ethyl acetate, preferably extracting three times; the washing can be performed with water and saturated sodium chloride solution sequentially; the drying can be carried out with anhydrous sodium sulfate: the concentrating can be performed by rotary evaporation; the removing the solvent can be performed by suction with an oil pump.

The present disclosure also provides a compound represented by formula 2:

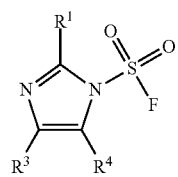

wherein $R^1$, $R^3$ and $R^4$ are as defined above.

In the present disclosure, the butyl can be n-butyl, sec-butyl, isobutyl or tert-butyl.

In the present disclosure, the room temperature can have the conventional definition of room temperature in the art, preferably 5-30° C.

In the present disclosure, the primary amine can be defined as a conventional primary amine in the art, which means that one of the hydrogen atoms in the amine molecule is substituted by a substituent.

In the present disclosure, the secondary amine can be defined as a conventional secondary amine in the art, which means that two hydrogen atoms in the amine molecule are substituted by substituents.

In accordance with common knowledge in the art, the preferred conditions can be combined arbitrarily to give various preferred embodiments of the present disclosure.

The reagents and raw materials used in the present disclosure are all commercially available.

The advantageous effects of the present disclosure:

the fluorosulfonyl-containing compound of the present disclosure is an amphoteric compound, which comprises a cation and an anion. The fluorosulfonyl-containing compound can be efficient for synthesizing fluorosulfonyl-containing products, and has low toxicity, synthetic simplicity and use convenience. In addition, the compound is in stable solid state at normal temperature and is applicable for an extremely wide range of substrates including phenolic compounds and amine compounds, and it is the only solid form reagent capable of realizing this type of chemical conversion at present, thus having favourable academic and application values.

BRIEF DESCRIPTION OF THE DRAWINGS

FIG. 1 is an experimental apparatus for preparing sulfuryl fluoride gas, in which A and B are both reaction bottles.

DETAILED DESCRIPTION OF THE PREFERRED EMBODIMENT

The following embodiments further illustrate the present disclosure, but the present disclosure is not limited by the scope of the following embodiments. The experimental methods without specifying the specific condition in the following embodiments are performed according to conventional methods and conditions, or according to the commercial instructions.

Experimental Instruments:

$^1$H NMR spectra were recorded on an Agilent-400 (400 MHz) nuclear magnetic resonance spectrometer, the internal standard of $^1$H NMR was TMS (δ 0.00) or CDCl$_3$ (δ 7.26).

$^{13}$C NMR spectra were recorded on an Bruker AM-400 (100.7 MHz) nuclear magnetic resonance spectrometer, the internal standard of $^{13}$C NMR was CDCl$_3$ (δ 77.16), DMSO-d$_6$ (δ 39.52), CD$_3$CN (δ 1.32), (CD$_3$)$_2$CO (δ 29.84, 206.26).

$^{19}$F NMR spectra were recorded on an Agilent-400 (376 MHz) nuclear magnetic resonance spectrometer, the external standard of $^{19}$F NMR was FCCl$_3$ (δ 0.00), low field was regarded as positive.

LC-MS (ESI) data were recorded on a Waters ACQUITY UPLC H-Class system and a ACQUITY QDa mass spectrometry detector (eluent: 0.1% trifluoroacetic acid aqueous solution and acetonitrile).

GC-MS (EI) data was recorded on SHIMADZU's GC-2010 Plus and GCMS-QP2010 Ultra (method: T$_0$=50° C., t=3 min, ramp=25° C./min; T$_1$=100° C., t=2 min, ramp=10° C./min; T$_2$=300° C., t=3 min) or Agilent 7890A GC System and Agilent 5975C Inert MSD system (method: T$_0$=80° C., t=3 min, ramp=20° C./min; T$_1$=300° C., t=15 min).

HRMS spectra were determined on a Finnigan MAT 8430 mass spectrometer.

Melting point was recorded on BUCHI M-565 melting point meter.

Experimental Reagents and Materials:

Column chromatography used silica gel (300-400 mesh or 100-200 mesh) produced by Yantai Jiangyou Silica Gel Development Co., Ltd, thin layer chromatography plate used was the thin layer chromatography plate produced by Yantai Jiangyou Silica Gel Development Co., Ltd, the color development tools included ZF-7A portable ultraviolet detector, iodine cylinder and alkaline potassium permanganate solution.

The reagents used were purchased from Shanghai Aladdin Biochemical Technology Co., Ltd., Tokyo Chemical Industry (TCI, Shanghai) Co., Ltd., Shanghai Macklin Biochemical Technology Co., Ltd., Energy Chemical (Shanghai) Co., Ltd., Alfa Aesar (China) Chemical Co., Ltd., Shanghai Adamas Technology Co., Ltd., Shanghai Shuya Pharmaceutical Technology Co., Ltd., Shanghai Bide Pharmaceutical Technology Co., Ltd., Shanghai Tianlian Chemical Technology Co., Ltd., Shanghai Xianding Biological Technology Co., Ltd., Shanghai Lingfeng Chemical Reagent Co., Ltd. or Shanghai Reagent Plant III.

Solvents were purchased from Shanghai Macklin Biochemical Technology Co., Ltd (Macklin), Shanghai Adamas Technology Co., Ltd., Shanghai Tianlian Chemical Technology Co., Ltd., Shanghai Dahe Chemicals Co., Ltd., and Shanghai Hebang Pharmaceutical Technology Co., Ltd., and were directly used after purchase without additional treatment.

In the embodiments of the present disclosure, Tfo is

i.e., CF$_3$SO$_3$; RT refers to room temperature.

Embodiment 1

Preparation of 1-(fluorosulfonyl)-2,3-dimethyl-1H-imidazolium trifluoromethanesulfonate Scheme 1 preparation of 1-(fluorosulfonyl)-2,3-dimethyl-1H-imidazolium trifluoromethanesulfonate

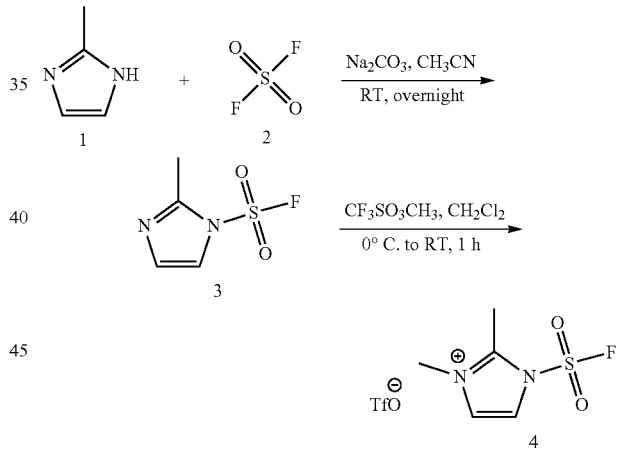

2-Methylimidazole [Compound 1] (49.3 g, 600 mmol) was added to a suspension of sodium carbonate (159.1 g, 1500 mmol) in acetonitrile (600 mL) at room temperature. The reaction system was degassed to generate negative pressure by a water pump, and then sulfuryl fluoride gas [Compound 2] (18 L, 730 mmol) was introduced from a balloon filled with the gas. The reaction mixture was stirred overnight. After completion of the reaction as indicated by TLC (petroleum ether:ethyl acetate=10:1, product: R$_f$=0.44), the reaction mixture was filtered through silica gel (10-40 mesh), the filter cake was washed with dichloromethane (600 mL), and the filtrate was extracted with distilled water (3000 mL×3). The combined aqueous phase was back extracted with dichloromethane (600 mL). The combined organic phase was washed with saturated brine (600 mL) and dried over anhydrous sodium sulfate. The filtrate was concentrated by a rotary evaporator (as the boiling point of 2-methyl-1H-imidazole-1-sulfonyl fluoride is relatively low, the temperature was controlled below 20° C. and the pressure was controlled above 140 torr during concentration) to give 271.1 g of a mixed solution of 2-methyl-1H-imidazole-1-sulfonyl fluoride [Compound 3], dichloromethane and acetonitrile. After being quantified with p-toluenesulfonyl fluoride, the amount of the product was 96.4 g and the yield was 97.8%. Dichloromethane (600 mL) was added to the mixed solution prepared above under nitrogen atmosphere and cooled to 0° C. in an ice bath, and then methyl trifluoromethanesulfonate (67 mL, 592 mmol) was dropwise added to the mixture under stirring at a rate of 4.5 mL/min by a syringe. Subsequently, the ice bath was allowed to naturally melt and warm to room temperature, and the reaction lasted for 1 hour. After completion of the reaction as indicated by LC-MS, the reaction mixture was concentrated by a rotary evaporator to give a viscous oil, to which methyl tert-butyl ether (500 mL) was then added. The resulting mixture was stirred, during which time a solid precipitated out. The supernatant was poured out, and then the solid was washed with methyl tert-butyl ether (500 mL×2) and suctioned by an oil pump to remove the residual solvent to give 1-(fluorosulfonyl)-2,3-dimethyl-1H-imidazolium trifluoromethanesulfonate [Compound 4] as a white solid (179.6 g, 93.2%, total yield 91% (Scheme 1).

White solid, m.p. 58-60° C., 179.6 g 91% yield; $^1$H NMR (400 MHz, CD$_3$CN) δ 7.87 (d, J=2.4 Hz, 1H), 7.56 (d, J=2.8 Hz, 1H), 3.85 (s, 3H), 2.86 (s, 3H); $^{13}$C NMR (100 MHz, CD$_3$CN) δ 151.4, 125.5, 122.1, 122.0 (q, J=318 Hz), 37.5, 12.9; $^{19}$F NMR (376 MHz, CD$_3$CN) δ 61.4 (s, 1F), −78.1 (s, 3F); LC-MS (t$_R$): 0.23 min; ESI-MS (m/z): 179 [M]$^+$, 148 [M]$^-$; HRMS (DART, m/z): calculated for C$_5$H$_8$O$_2$N$_2$FS: 179.0285 [M]$^+$, found: 179.0284; HRMS (DART, m/z): calculated for CO$_3$F$_3$S: 148.9526 [M]$^-$, found: 148.9525.

Embodiment 2

Preparation of 1-(fluorosulfonyl)-3-methyl-1H-imidazolium trifluoromethanesulfonate Scheme 2: Preparation of 1-(fluorosulfonyl)-3-methyl-1H-imidazolium trifluoromethansulfonate

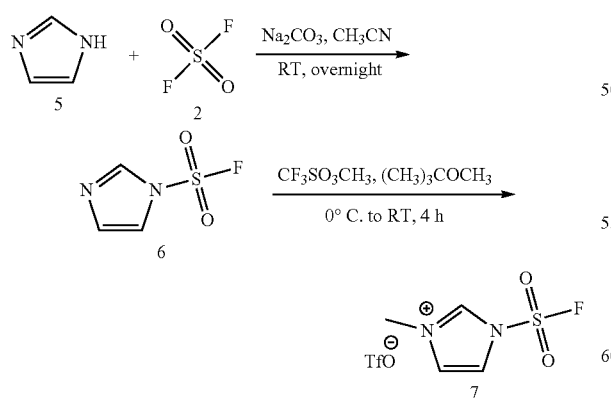

Imidazole [Compound 5] (1.36 g, 20 mmol) was added to a suspension of sodium carbonate (4.2 g, 40 mmol) in acetonitrile (80 mL) at room temperature. The reaction system was degassed to generate negative pressure by a water pump, and then sulfuryl fluoride gas [Compound 2] (0.6 L, 25 mmol) was introduced from a balloon filled with the gas. The resulting mixture was stirred overnight. After completion of the reaction as indicated by TLC (petroleum ether:ethyl acetate=10:1, product: R$_f$=0.48), water (200 mL) was added to partition the reaction mixture, which was then extracted with dichloromethane (200 mL×3). The combined organic phase was washed with saturated brine (150 mL), dried over anhydrous magnesium sulfate, and filtered through diatomite. The filtrate was concentrated to about 40 mL by a rotary evaporator (as the boiling point of 1H-imidazole-1-sulfonyl fluoride is relatively low, the temperature was controlled below 28° C. and the pressure was controlled above 140 torr during concentration) to give a mixed solution of the product 1H-imidazole-1-sulfonyl fluoride [compound 6], dichloromethane and acetonitrile. Under nitrogen atmosphere, methyl tert-butyl ether (50 mL) was added to the mixed solution prepared above. Subsequently, the resulting mixture was cooled to 0° C. in an ice bath, followed by slow addition of methyl trifluoromethanesulfonate (3.28 g, 20 mmol) by a syringe while stirring. After the dropwise addition of methyl trifluoromethanesulfonate, the ice bath was removed, and the reaction was allowed to run for 4 hours at room temperature. After completion of the reaction as indicated by TLC, the reaction mixture was concentrated by a rotary evaporator to give a white solid, which was washed with methyl tert-butyl ether (50 mL×3) and then suctioned by an oil pump to remove the residual solvent to give 1-(fluorosulfonyl)-3-methyl-1H-imidazolium trifluoromethanesulfonate [Compound 7] as a white solid (5.3 g, 84%) (Scheme 2).

White solid, m.p. 67-71° C., 5.3 g, 84% yield; $^1$H NMR (400 MHz, CD$_3$CN) δ 9.41 (s, 1H), 8.01 (s, 1H), 7.68 (s, 1H), 3.98 (s, 3H); $^{13}$C NMR (100 MHz, CD$_3$CN) δ 141.3 (s), 127.6, 121.9 (q, J=318 Hz), 122.4, 38.5; $^{19}$F NMR (376 MHz, CD$_3$CN) δ 61.2 (s, 1F), −78.1 (s, 3F).

Embodiment 3

Preparation of 1-(fluorosulfonyl)-1H-imidazolium bisulfate

Scheme 3 Preparation of 1-(fluorosulfonyl)-1H-imidazolium bisulfate

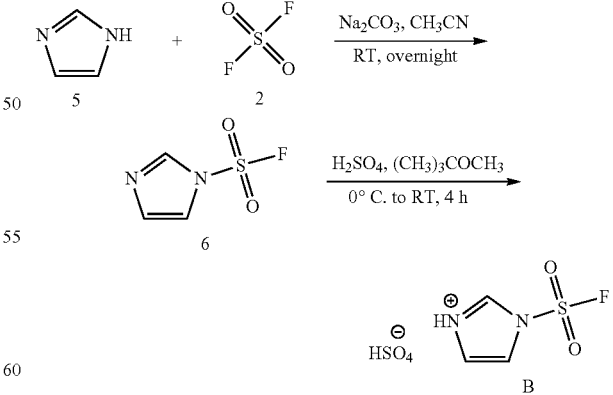

Imidazole [Compound 5] (0.68 g, 10 mmol) was added to a suspension of sodium carbonate (2.1 g, 20 mmol) in acetonitrile (40 mL) at room temperature. The reaction system was degassed to generate negative pressure by a water pump, and then sulfuryl fluoride gas [Compound 2]

(0.4 L, 16 mmol) was introduced from a balloon filled with the gas. The resulting mixture was stirred overnight. After completion of the reaction as indicated by TLC (petroleum ether:ethyl acetate=10:1, $R_f$=0.48), water (100 mL) was added to partition the reaction mixture, which was then extracted with dichloromethane (80 mL×3). The combined organic phase was washed with saturated brine (60 mL), dried over anhydrous magnesium sulfate, and filtered through diatomite. The filtrate was concentrated to 20 mL by a rotary evaporator (as the boiling point of 1H-imidazole-1-sulfonyl fluoride is relatively low, the temperature was controlled below 28° C. and the pressure was controlled above 140 torr during concentration) to give a mixed solution of 1H-imidazole-1-sulfonyl fluoride [compound 6], dichloromethane and acetonitrile. Under nitrogen atmosphere, methyl tert-butyl ether (20 mL) was added to the mixed solution prepared above, and then the resulting mixture was cooled to 0° C. in an ice bath, followed by addition of concentrated sulfuric acid (0.55 mL, 10 mmol) by a syringe while stirring. After the dropwise addition, the ice bath was removed, and the reaction was allowed to run for 4 hours at room temperature. After completion of the reaction as indicated by TLC, the reaction mixture was filtered through a filter paper to give a white solid, which was washed with methyl tert-butyl ether (20 mL×3) and then suctioned by an oil pump to remove the residual solvent to give 1-(fluorosulfonyl)-1H-imidazolium bisulfate [Compound 8] as a white solid (2.36 g, 95%) (Scheme 3).

On a melting point meter, the temperature was set at 60-120° C. and the heating gradient 1° C./min, the sample started melting at 94.5° C., started bubbling at 96° C., bubbles disappeared at 104° C., and the sample became a colorless and transparent liquid.

White solid, 2.36 g, 95% yield; $^1$H NMR (400 MHz, DMSO-$d_6$) δ 11.55 (br, 2H), 8.65 (s, 1H), 8.08 (s, 1H), 7.38 (s, 1H); $^{19}$F NMR (376 MHz, DMSO-$d_6$) δ 59.7 (s, 1F).

Embodiment 4

Preparation of 2-butyl-1-(fluorosulfonyl)-3-methyl-1H-imidazolin trifluoromethanesulfonate Scheme 4 Preparation of 2-butyl-1-(fluorosulfonyl)-3-methyl-1H-imidazolium trifluoromethanesulfonate

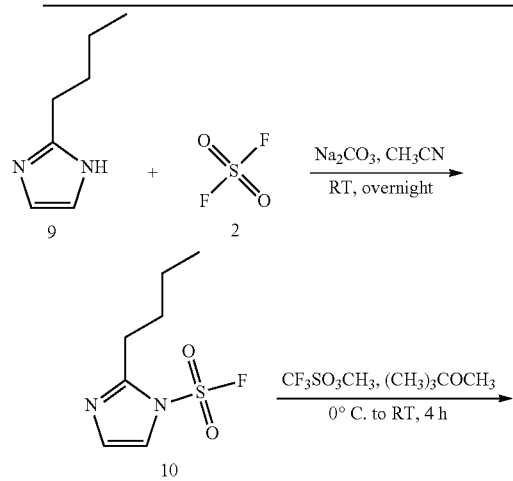

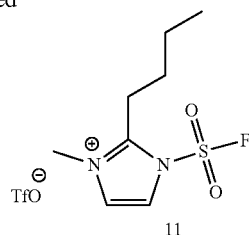

2-Butylimidazole [Compound 9] (0.62 g, 5 mmol) was added to a suspension of sodium carbonate (1.06 g, 10 mmol) in acetonitrile (50 mL) at room temperature. The reaction system was degassed to generate negative pressure by a water pump, and then sulfuryl fluoride gas [Compound 2] (0.25 L, 10 mmol) was introduced from a balloon filled with the gas. The resulting mixture was stirred overnight. After completion of the reaction as indicated by TLC (petroleum ether ethyl acetate=10:1, product: $R_f$=0.50), water (100 mL) was added to partition the reaction mixture, which was then extracted with ethyl acetate (100 mL×3). The combined organic phase was washed with saturated brine (80 mL), dried over anhydrous sodium sulfate, and filtered through a filter paper. The filtrate was concentrated by a rotary evaporator, and then purified by column chromatography (petroleum ether:dichloromethane=5:1) to give 2-butyl-1-H imidazole-1-sulfonyl fluoride [compound 10] as a colorless oil (938 mg, 88%). Under nitrogen atmosphere, methyl tert-butyl ether (50 mL) was added to the 2-butyl-1-H imidazole-1-sulfonyl fluoride [compound 10] (938 mg, 4.5 mmol) prepared above and cooled to 0° C. in an ice bath, followed by slow addition of methyl trifluoromethanesulfonate (0.51 mL, 5 mmol) by a syringe while stirring. After the dropwise addition, the ice bath was removed, and the reaction was allowed to run for 4 hours at room temperature, during which time the reaction was monitored by TLC. The reaction mixture was concentrated by a rotary evaporator, washed with methyl tert-butyl ether (50 mL×3), and then suctioned by an oil pump to remove the residual solvent to give 2-butyl-1-(fluorosulfonyl)-3-methyl-1H-imidazolium trifluoromethanesulfonate [Compound 11] as a colorless oil (0.2 g, 12%) (Scheme 4).

Colorless oil, 0.2 g, 12% yield; $^1$H NMR (400 MHz, CDCl$_3$) δ 7.79 (d, J=5.7 Hz, 2H), 4.03 (s, 3H), 3.29 (t, J=8 Hz, 2H), 1.71 (quin, J=7.6 Hz, 2H), 1.52 (sext, J=7.6 Hz, 2H), 1.00 (t, J=7.2 Hz, 3H); $^{19}$F NMR (376 MHz, CDCl$_3$) δ 62.7 (s, 0.7F), −78.7 (s, 3F).

Embodiment 5

Preparation of 1-(fluorosulfonyl)-2-isopropyl-3-methyl-1H-imidazolium trifluoromethanesulfonate Scheme 5 Preparation of 1-(fluorosulfonyl)-2-isopropyl-3-methyl-1H-imidazolium trifluoromethanesulfonate

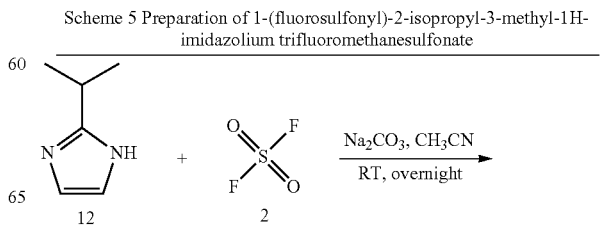

-continued

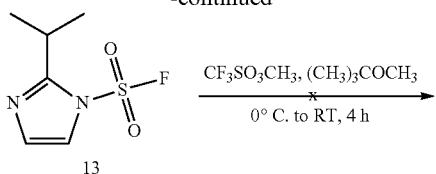

2-Isopropylimidazole [Compound 12] (3.5 g, 32 mmol) was added to a suspension of sodium carbonate (6.78 g, 64 mmol) in acetonitrile (100 mL) at room temperature. The reaction system was degassed to generate negative pressure by a water pump, and then sulfuryl fluoride gas [Compound 2] (1 L, 40 mmol) was introduced from a balloon filled with the gas. The resulting mixture was stirred overnight. After completion of the reaction as indicated by TLC (petroleum ether:ethyl acetate=10:1, product: $R_f$=0.53), water (200 mL) was added to partition the reaction mixture, and the resulting mixture was extracted with ethyl acetate (200 mL×3). The combined organic phase was washed with saturated brine (150 mL), dried over anhydrous sodium sulfate, and filtered through a filter paper. The filtrate was concentrated by a rotary evaporator, and purified by column chromatography (silica gel 300-400 mesh, petroleum ether:ethyl acetate=10:1) to give 2-isopropyl-1-H-imidazole-1-sulfonyl fluoride [compound 13] as a colorless oil (2.2 g, 35%) (Scheme 5).

Colorless oil, 2.2 g, 35% yield: $^1$HNMR (400 MHz, CDCl$_3$) δ 7.32 (s, 1H), 7.03 (s, 1H), 3.47 (sept, J=6.8 Hz, 1H), 1.38 (d, J=6.8 Hz, 6H); $^{19}$F NMR (376 MHz, CDCl$_3$) δ 59.3 (s, 1F).

Methylation reaction was messy, and 1-(fluorosulfonyl)-2-isopropyl-3-methyl-1H-imidazolium trifluoromethanesulfonate was not obtained [Compound 14].

Embodiment 6

Preparation of 1-(fluorosulfonyl)-2,3-dimethyl-1H-benzimidazolium trifluoromethanesulfonate Scheme 6 Preparation of 1-(fluorosulfonyl)-2,3-dimethyl-1H-benzimidazolium trifluoromethanesulfonate

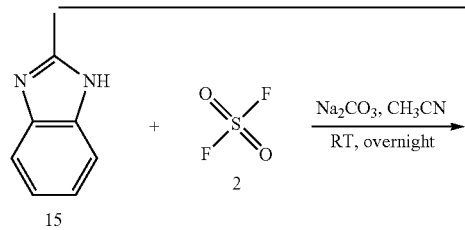

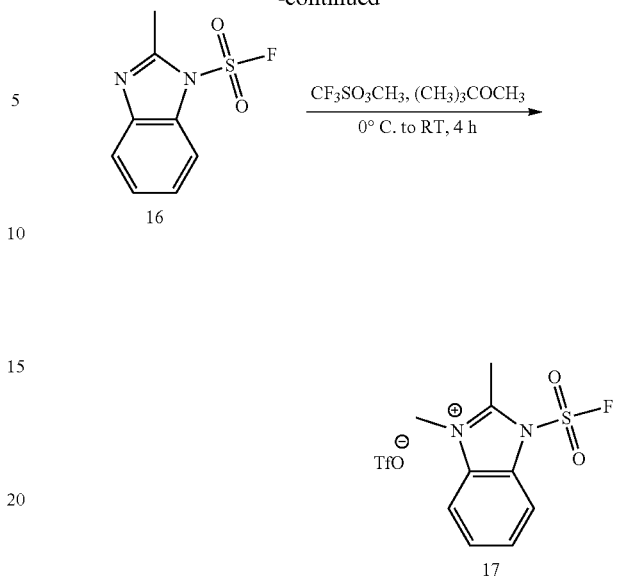

2-Methylbenzimidazole [Compound 15] (3.96 g, 30 mmol) was added to a suspension of sodium carbonate (6.3 g, 60 mmol) in acetonitrile (50 mL) at room temperature. The reaction system was degassed to generate negative pressure by a water pump, and then sulfuryl fluoride gas [Compound 2] (1 L, 40 mmol) was introduced from a balloon filled with the gas. The resulting mixture was stirred overnight. After completion of the reaction as indicated by TLC (petroleum ether:ethyl acetate=10:1, product: $R_f$=0.50), water (100 mL) was added to partition the reaction mixture, which was then extracted with ethyl acetate (100 mL). The combined organic phase was washed with saturated brine (80 mL), dried over anhydrous sodium sulfate, and filtered through a filter paper. The filtrate was concentrated by a rotary evaporator, and then purified by column chromatography (silica gel 300-400 mesh, petroleum ether: ethyl acetate=10:1) to give 2-methyl-1H-benzimidazole-1-sulfonyl fluoride [compound 16] as a white solid (0.89 g, 14%).

White solid, 0.89 g, 14% yield; $^1$H NMR (400 MHz, CDCl$_3$) δ 7.81 (m, 1H), 7.74 (m, 1H), 7.42 (m, 2H), 2.86 (s, 3H); $^{19}$F NMR (376 MHz, CDCl$_3$) δ 58.3 (s).

Under nitrogen atmosphere, methyl tert-butyl ether (50 mL) was added to the 2-methyl-1H-benzimidazole-1-sulfonyl fluoride [compound 16] (0.89 g, 4 mmol) prepared above and cooled to 0° C. in an ice bath, followed by slow addition of methyl trifluoromethanesulfonate (0.443 g, 4 mmol) by a syringe while stirring. After the dropwise addition, the ice bath was removed, and the reaction was allowed to run for 4 hours at room temperature, during which time the reaction was monitored by TLC. The reaction mixture was concentrated by a rotary evaporator, washed with methyl tert-butyl ether (50 mL×3), and then suctioned by an oil pump to remove the residual solvent to give 1-(fluorosulfonyl)-2,3-dimethyl-1H-benzimidazole trifluoromethanesulfonate [Compound 17] as a white solid (1.17 g, 78%) (Scheme 6).

White solid, 1.17 g, 78% yield; $^1$H NMR (400 MHz, CD$_3$CN) δ 8.10 (s, 1H), 7.98 (s, 1H), 7.87 (s, 2H), 4.10 (s, 3H), 3.13 (s, 3H); $^{19}$F NMR (376 MHz, CD$_3$CN) δ 62.8 (s, 1F), −78.1 (s, 3F).

Embodiment 7

Preparation of 2-chloro-1-(fluorosulfonyl)-3-methyl-1H-benzimidazolium trifluoromethanesulfonate Scheme 7 Preparation of 2-chloro-1-(fluorosulfonyl)-3-methyl-1H-benzimidazolium trifluoromethanesulfonate

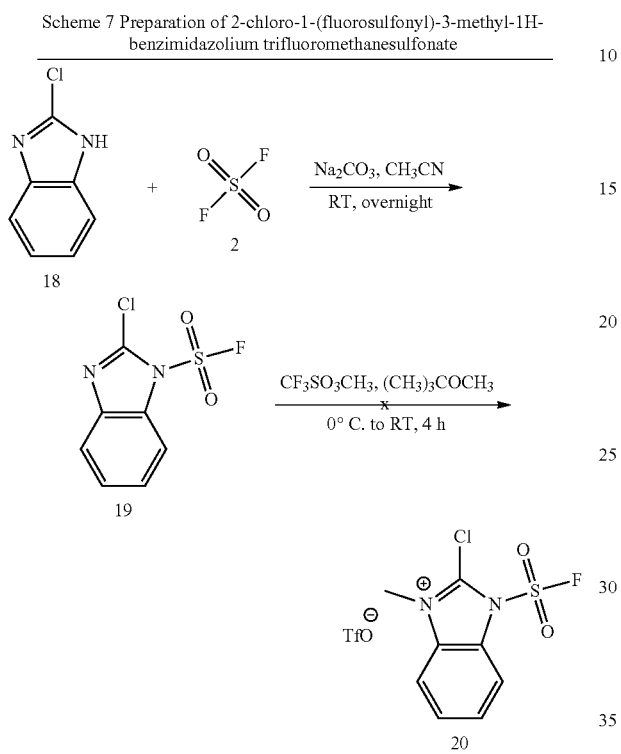

2-Chlorobenzimidazole [Compound 18] (4.2 g, 30 mmol) was added to a suspension of sodium carbonate (6.3 g, 60 mmol) in acetonitrile (50 mL) at room temperature. The reaction system was degassed to generate negative pressure by a water pump, and then sulfinyl fluoride gas [Compound 2] (1 L, 40 mmol) was introduced from a balloon filled with the gas. The resulting mixture was stirred overnight. After completion of the reaction as indicated by TLC (petroleum ether:ethyl acetate=20:1, product: $R_f$=0.64), water (100 mL) was added to partition the reaction mixture, which was then extracted with ethyl acetate (100 mL×3). The combined organic phase was washed with saturated brine (80 mL), dried over anhydrous sodium sulfate, and filtered through a filter paper. The filtrate was concentrated by a rotary evaporator, and then purified by column chromatography (silica gel 300-400 mesh, petroleum ether:ethyl acetate=20:1) to give 2-chloro-1H-benzimidazole-1-sulfonyl fluoride [Compound 19] as a white solid (2.61 g, 39%) (Scheme 7).

White solid, 2.61 g, 39% yield; $^1$H NMR (400 MHz, CDCl$_3$) δ 7.83 (m, 1H), 7.75 (m, 1H), 7.49 (m, 2H); $^{19}$F NMR (376 MHz, CDCl$_3$) δ 60.4 (s, 1F).

Methylation reaction was messy, and 2-chloro-1-(fluorosulfonyl)-3-methyl-1H-benzimidazolium trifluoromethanesulfonate [Compound 20] was not obtained.

Embodiment 8

Preparation of 2-ethyl-1-(fluorosulfonyl)-3,4-dimethyl-1H-imidazolium trifluoromethanesulfonate Scheme 8 Preparation of 2-ethyl-1-(fluorosulfonyl)-3,4-dimethyl-1H-imidazolium trifluoromethanesulfonate

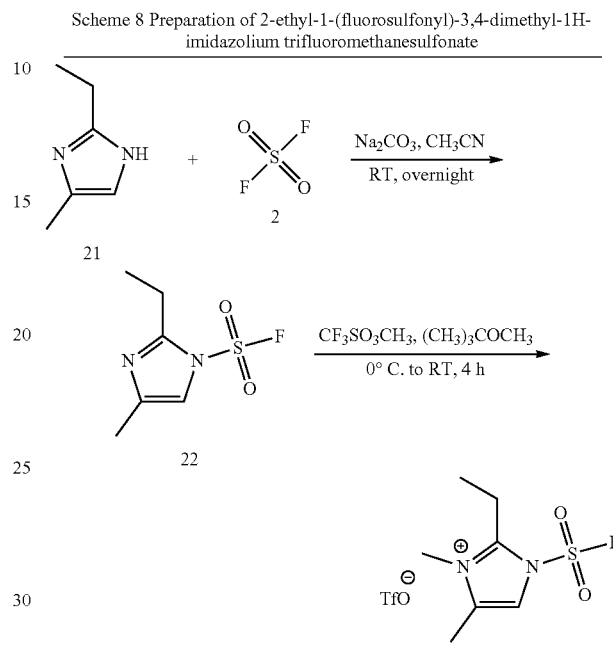

2-Ethyl-4-methylimidazole [Compound 21] (1.1 g, 10 mmol) was added to a suspension of sodium carbonate (2.1 g, 20 mmol) in acetonitrile (50 mL) at room temperature. The reaction system was degassed to generate negative pressure by a water pump, and then sulfuryl fluoride gas [Compound 2] (0.4 L, 16 mmol) was introduced from a balloon filled with the gas. The resulting mixture was stirred overnight. After completion of the reaction as indicated by TLC (petroleum ether:ethyl acetate=10:1, product: $R_f$=0.50), water (100 mL) was added to partition the reaction mixture, which was then extracted with ethyl acetate (80 mL×3). The combined organic phase was washed with saturated brine (60 mL), dried over anhydrous sodium sulfate, and filtered through a filter paper. The filtrate was concentrated by a rotary evaporator, and then purified by column chromatography (silica gel 300-400 mesh, petroleum ether:ethyl acetate=10:1) to give 2-ethyl-4-methyl-1H-imidazole-1-sulfonyl fluoride [compound 22] (1.27 g, 66%) as a white solid. Under nitrogen atmosphere, methyl tert-butyl ether (50 mL) was added to the 2-ethyl-4-methyl-1H-imidazole-1-sulfonyl fluoride [compound 22] (1.27 g, 6.6 mmol) prepared above and cooled to 0° C. in an ice bath, followed by slow addition of methyl trifluoromethanesulfonate (0.73 mL, 6.6 mmol) by a syringe while stirring. After the dropwise addition, the ice bath was removed, and the reaction was allowed to run for 4 hours at room temperature, during which time the reaction was monitored by TLC. The reaction mixture was concentrated by a rotary evaporator, washed with methyl tert-butyl ether (50 mL×3) and then suctioned by an oil pump to remove the residual solvent to give 2-ethyl-1-(fluorosulfonyl)-3,4-dimethyl-1H-imidazolium trifluoromethanesulfonate [Compound 23] as a white solid (2.22 g, 96%) (Scheme 9).

White solid, 2.22 g, 96% yield; $^1$H NMR (400 MHz, CDCl$_3$) δ 7.52 (s, 1H), 3.89 (s, 3H), 3.38 (q, J=7.6 Hz, 2H), 2.42 (s, 3H), 1.41 (t, J=7.6 Hz, 3H); $^{19}$F NMR (376 MHz, CDCl$_3$) δ 62.3 (s, 1F), −78.6 (s, 3F).

Embodiment 9

Preparation of 2,4,5-tribromo-1H-imidazole-1-sulfonyl fluoride

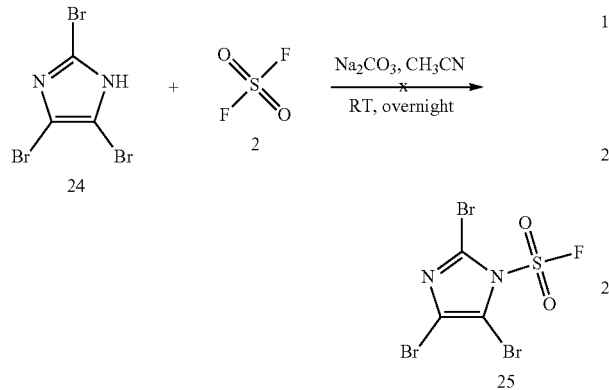

Scheme 9 Preparation of 2,4,5-tribromo-1H-imidazole-1-sulfonyl fluoride 2,4,5-Tribromimidazole [Compound 24] (1.5 g, 5 mmol) was added to a suspension of sodium carbonate (1.06 g, 10 mmol) in acetonitrile (50 mL) at room temperature. The reaction system was degassed to generate negative pressure by a water pump, and then sulfuryl fluoride gas [Compound 2] was introduced from a balloon filled with the gas. The reaction mixture was stirred overnight. No reaction occurred (Scheme 9).

Embodiment 10

Preparation of 2-chloro-5-nitro-1H-imidazole-1-sulfonyl fluoride

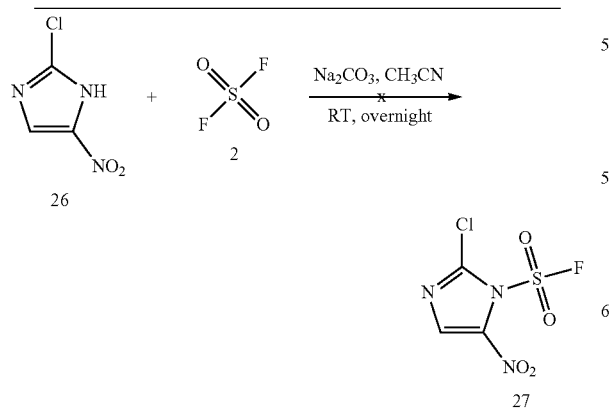

Scheme 10 Preparation of 2-chloro-5-nitro-1H-imidazole-1-sulfonyl fluoride

2-Chloro-4-nitroimidazole [compound 26] (730 mg, 5 mmol) was added to a suspension of sodium carbonate (1.06 g, 10 mmol) in acetonitrile (50 mL) at room temperature. The reaction system was degassed to generate negative pressure by a water pump, and then sulfuryl fluoride gas [compound 2] was introduced from a balloon and the reaction mixture was stirred overnight. No reaction occurred (Scheme 10).

Embodiment 11

Preparation of 2-nitro-1H-imidazole-1-sulfonyl fluoride

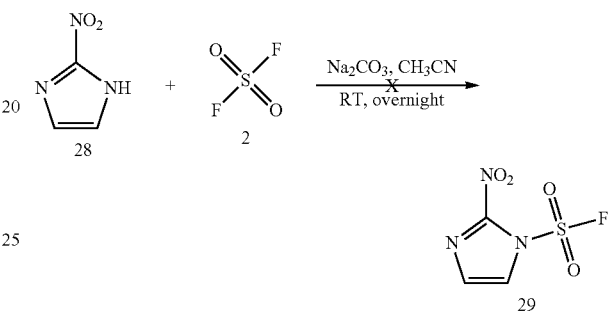

Scheme 11 Preparation of 2-nitro-1H-imidazole-1-sulfonyl fluoride

2-Nitroimidazole [Compound 28] (560 mg, 5 mmol) was added to a suspension of sodium carbonate (1.06 g, 10 mmol) in acetonitrile (50 mL) at room temperature. The reaction system was degassed to generate negative pressure by a water pump, and then sulfuryl fluoride gas [Compound 2] was introduced from a balloon filled with the gas. The reaction mixture was stirred overnight. No reaction occurred (Scheme 11).

Embodiment 12

Preparation of methyl 1-(fluorosulfonyl)-1H-imidazole-2-carboxylate

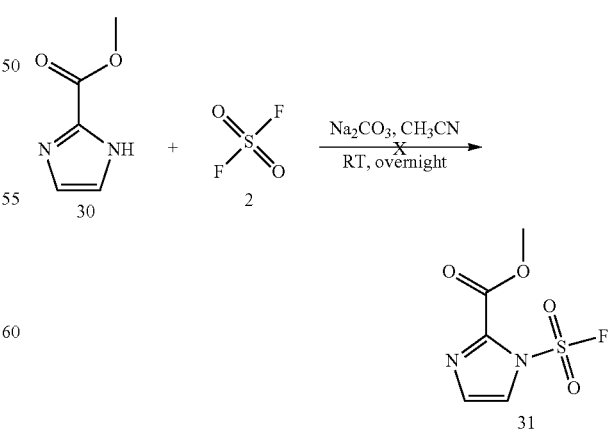

Scheme 12 Preparation of methyl 1-(fluorosulfonyl)-1H-imidazole-2-carboxylate

Methyl 1H-imidazole-2-carboxylate [compound 28] (630 mg, 5 mmol) was added to a suspension of sodium carbonate (1.06 g, 10 mmol) in acetonitrile (50 mL) at room temperature. The reaction system was degassed to generate negative pressure by a water pump, and then sulfuryl fluoride gas [compound 2] was introduced from a balloon filled with the gas. The reaction mixture was stirred overnight. Less than 2% of the raw materials reacted (Scheme 12).

Embodiment 13

Preparation of sulfuryl fluoride gas

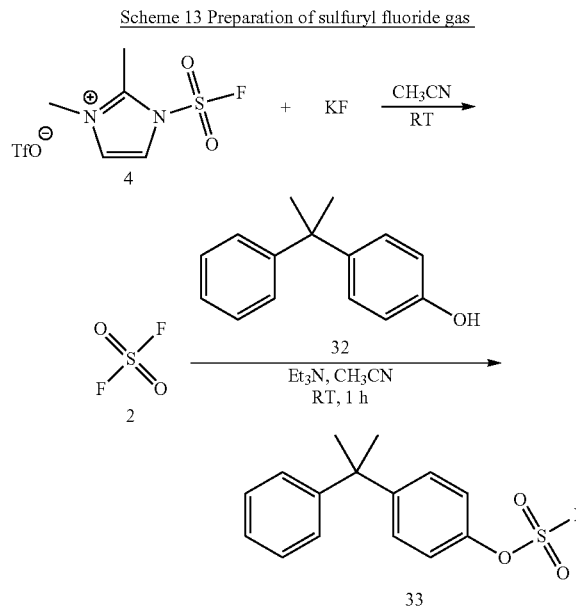

The device for preparing sulfuryl fluoride gas is shown in FIG. 1.

As shown in FIG. 1, potassium fluoride (581 mg, 10 mmol) was added to the reaction bottle A at mom temperature, 4-cumylphenol[compound 32] (212 mg, 1 mmol) was added into the reaction bottle B with a buffer balloon inserted, and the two reaction bottles were connected by an airway tube. The reaction system was degassed to generate negative pressure by a water pump, and a solution of triethylamine (152 mg, 1.5 mmol) in acetonitrile (5 mL) was injected into the reaction bottle B by a syringe, a solution of 1-(fluorosulfonyl)-2,3-dimethyl-1H-imidazolium trifluoromethanesulfonate [Compound 4] (3.283 g, 10 mmol) in acetonitrile (10 mL) was injected into the reaction bottle A. The reaction was allowed to run for 1 hour, during which time the reaction was monitored by TLC (petroleum ether:ethyl acetate=10:1, product: $R_f$=0.61). Fluorine spectrum detected that the reaction mixture in bottle B showed signal of the sulfuryl fluoride gas and 4-(2-phenyl-2-propyl)phenoxysulfonyl fluoride. Column chromatography (silica gel 300-400 mesh, petroleum ether:ethyl acetate=30:1) afforded 4-(2-phenyl-2-propyl)phenoxysulfonyl fluoride [compound 33] as a colorless liquid (288 mg, 97%). (Scheme 13).

Colorless liquid, 288 mg, 97% yield; $^1$H NMR (400 MHz, CDCl$_3$) δ 7.33-7.19 (m, 9H), 1.69 (s, 6H); 13C NMR (100 MHz, CDCl$_3$) δ 151.8, 149.6, 148.1, 128.9, 128.4, 126.8, 126.2, 120.3, 43.0, 30.8; $^{19}$F NMR (376 MHz, CDCl$_3$) δ 36.8 (s, 1F); GC-MS ($t_R$): 18.4 min; EI-MS (m/z): 294 [M]$^+$.

Embodiment 14

Preparation of 4-(2-phenyl-2-propyl)phenoxysulfonyl fluoride

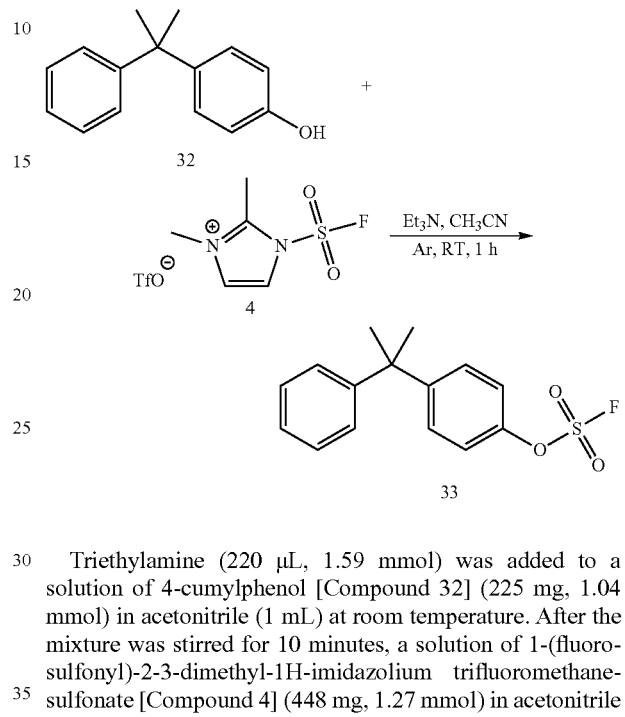

Triethylamine (220 μL, 1.59 mmol) was added to a solution of 4-cumylphenol [Compound 32] (225 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (448 mg, 1.27 mmol) in acetonitrile (1 mL) was added in one portion. The reaction was allowed to run for 1 hour under argon atmosphere, during which time the reaction was monitored by TLC (petroleum ether:ethyl acetate=10:1, product: $R_f$=0.61). After column chromatography purification (silica gel 300-400 mesh, petroleum ether: ethyl acetate=30:1), 4-(2-phenyl-2-propyl)phenoxysulfonyl fluoride [compound 33] was obtained as a colorless liquid (293 mg, 95%) (Scheme 14).

Colorless liquid, 293 mg, 95% yield; $^1$H NMR (400 MHz, CDCl$_3$) δ 7.32-7.20 (m, 9H), 1.69 (s, 6H); 13C NMR (100 MHz, CDCl$_3$) δ 151.8, 149.6, 148.1, 128.9, 128.3, 126.8, 126.2, 120.3, 43.0, 30.7; $^{19}$F NMR (376 MHz, CDCl$_3$) δ 36.8 (s, 1F); GC-MS ($t_R$): 18.4 min; EI-MS (m/z): 294 [M]$^+$.

Embodiment 15

Preparation of 2,2-propylbis(4,1-phenylene)-dioxysulfonyl fluoride

Scheme 15 Preparation of 2,2-propylbis-(4,1-phenylene)-dioxysulfonyl fluoride

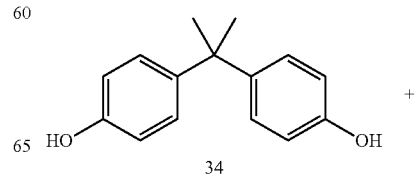

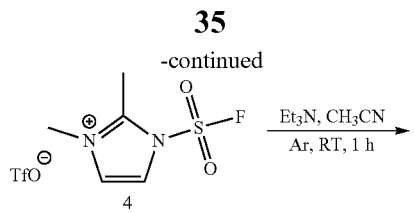

Triethylamine (220 μL, 1.59 mmol) was added to a solution of bisphenol A [Compound 34] (120 mg, 0.52 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (448 mg 1.27 mmol) in acetonitrile (1 mL) was added in one portion. The reaction was allowed to run for 1 hour under argon atmosphere, during which time the reaction was monitored by TLC (petroleum ether:ethyl acetate=10:1, product: $R_f$=0.43). After column chromatography (silica gel 300-400 mesh, petroleum ether:ethyl acetate=30:1), 2,2-propylbis-(4,1-phenylene)-dioxsulfonyl fluoride [compound 35] was obtained as a white solid (169 mg, 82%) (Scheme 5).

White solid, m.p 48.2-49.5° C., 169 mg, 82% yield; $^1$H NMR (400 MHz, CDCl$_3$) δ 7.32-7.25 (m, 8H), 1.70 (s, 6H); 13C NMR (100 MHz, CDCl$_3$) δ 150.6, 148.3, 128.9, 120.7, 43.0, 30.8; $^{19}$F NMR (376 MHz, CDCl$_3$) δ 37.0 (s, 2F); GC-MS ($t_R$): 22.0 min; EI-MS (m/z): 392 [M]$^+$.

Embodiment 16

Preparation of sulfonylbis(4,1-phenylene)dioxysulfonyl fluoride

Scheme 16 Preparation of sulfonylbis(4,1-phenylene)dioxysulfonyl fluoride

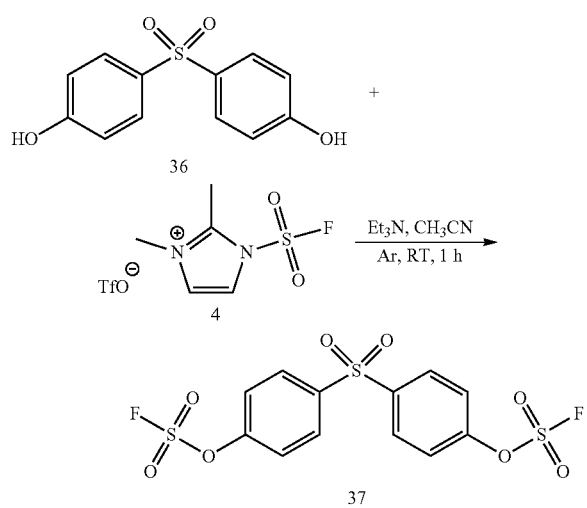

Triethylamine (220 μL, 1.59 mmol) was added to a solution of bisphenol S [Compound 36] (130 mg, 0.52 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (448 mg, 1.27 mmol) in acetonitrile (1 mL) was added in one portion. The reaction was allowed to run for 1 hour under argon atmosphere, during which time the reaction was monitored by TLC (petroleum ether:ethyl acetate=4:1, product: $R_f$=0.38). Column chromatography (silica gel 300-400 mesh, petroleum ether:ethyl acetate=4:1) afforded sulfonylbis(4,1-phenylene)dioxsulfonyl fluoride [compound 37] as a white solid (166 mg, 77%) (Scheme 6).

White solid, m.p 125.0-126.1° C., 166 mg, 77% yield; $^1$H NMR (400 MHz, CDCl$_3$) δ 8.10 (d, J=8.0 Hz, 4H), 7.54 (d, J=8.0 Hz, 4H); 13C NMR (100 MHz, CDCl$_3$) δ 153.0, 141.3, 130.7, 122.5; $^{19}$F NMR (376 MHz, CDCl$_3$) δ 39.0 (s, 2F); GC-MS ($t_R$): 23.6 min; EI-MS (m/z): 414 [M]$^+$.

Embodiment 17

Preparation of (1,1'-biphenyl)-4,4'-disulfonyl fluoride

Scheme 17 Preparation of (1,1'-biphenyl)-4,4'-disulfonyl fluoride

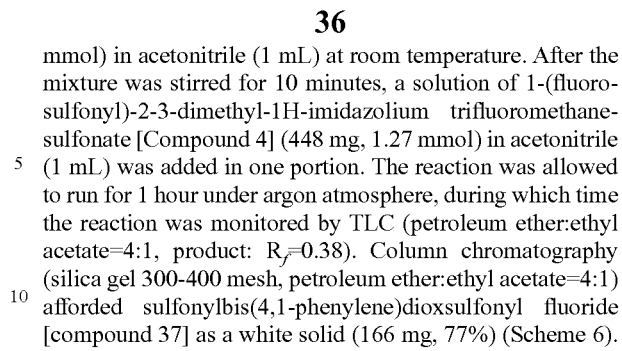

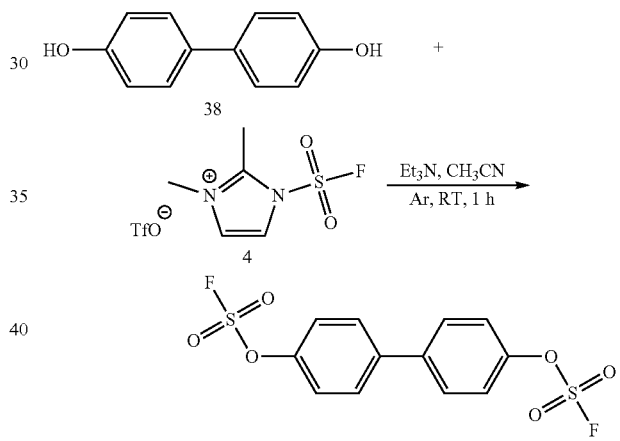

Triethylamine (440 μL, 3.17 mmol) was added to a solution of biphenyl diphenol [Compound 38] (198 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (840 mg, 2.56 mmol) in acetonitrile (1 mL) was added in one portion. The reaction was allowed to run for 1 hour under argon atmosphere, during which time the reaction was monitored by TLC (petroleum ether:ethyl acetate=10:1, product: $R_f$=0.53). Column chromatography (silica gel 300-400 mesh, petroleum ether ethyl acetate=10:1) afforded (1,1'-biphenyl)-4,4'-disulfonyl fluoride [compound 39] as a light green solid (294 mg, 81%) (Scheme 7).

Light green solid, m.p 95.3-96.6° C., 294 mg, 81% yield; $^1$H NMR (400 MHz, CDCl$_3$) δ 7.65 (d, J=8.8 Hz, 4H), 7.45 (d, J=8.8 Hz, 4H); $^{13}$C NMR (100 MHz, CDCl$_3$) δ 150.0, 140.1, 129.3, 121.7; $^{19}$F NMR (376 MHz, CDCl$_3$) δ +37.4 (s, 2F); GC-MS ($t_R$): 20.4 min, EI-MS (m/z): 350 [M]$^+$; HRMS (EI, m/z): calculated for $C_{12}H_8O_6F_2S_2$: 349.9730 [M]$^+$, found: 349.9729.

Embodiment 18

Preparation of 2,7-naphthyl-disulfonyl fluoride

Scheme 18 preparation of 2,7-naphthyl-disulfonyl fluoride

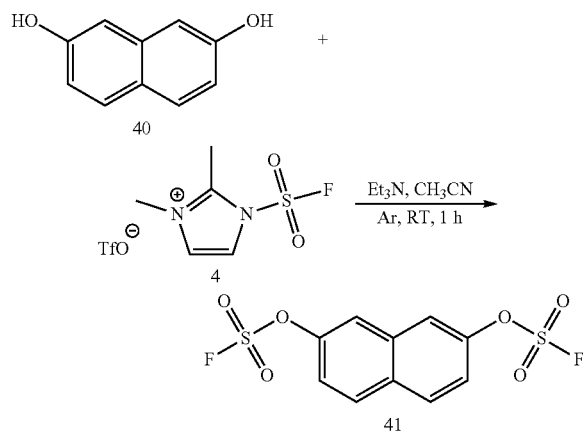

Triethylamine (440 μL, 3.17 mmol) was added to a solution of 2,7-dihydroxynaphthalene [Compound 40] (169 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (840 mg, 2.56 mmol) in acetonitrile (1 mL) was added in one portion. The reaction was allowed to run for 1 hour under argon atmosphere, during which time the reaction was monitored by TLC (petroleum ether:ethyl acetate=10:1, product: $R_f$=0.54). Column chromatography (silica gel 300-400 mesh, petroleum ether:ethyl acetate=10:1) afforded 2,7-naphthyl-disulfonyl fluoride [compound 41] as a white solid (253 mg, 75%) (Scheme 8).

White solid, m.p. 122.7-124.3° C., 253 mg, 75% yield; $^1$H NMR (400 MHz, DMSO-$d_6$) δ 8.40 (d, J=2.0 Hz, 2H), 8.34 (s, 1H), 8.31 (s, 1H), 7.88 (d, J=2.0 Hz, 1H), 7.86 (d, J=2.0 Hz, 1H); $^{13}$C NMR (100 MHz, DMSO-$d_6$) δ 148.3, 133.3, 131.5, 120.9, 119.5; $^{19}$F NMR (376 MHz, DMSO-$d_6$) δ +39.8 (s, 2F); GC-MS ($t_R$): 17.9 min, EI-MS (m/z): 324 [M]$^+$.

Embodiment 19

Preparation of (8R,9S,13S,14S,17R)-17-ethynyl-17-hydroxy-13-methyl-7,8,9,11,12,13,14,15,16,17-decahydro-6H-cyclopenta[a]-3-phenanthroxysulfonyl fluoride Scheme 19 Preparation of (8R,9S,13S,14S,17R)-17-ethynyl-17-hydroxy-13-methyl-7,8,9,11,12,13,14,15,16,17-decahydro-6H-cyclopenta[a]-3-phenanthroxysulfonyl fluoride

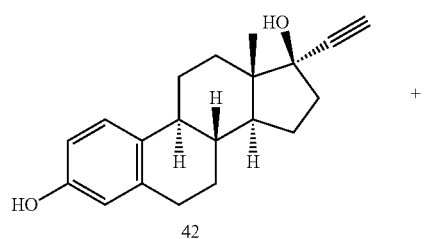

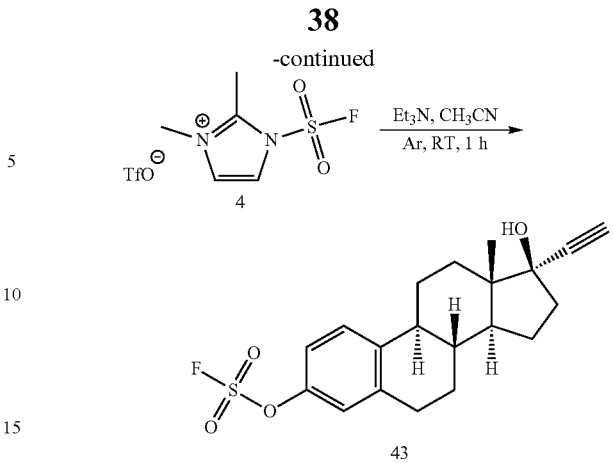

Triethylamine (220 μL, 1.59 mmol) was added to a solution of ethinylestradiol [Compound 42] (315 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (448 mg, 1.27 mmol) in acetonitrile (1 mL) was added in one portion. The reaction was allowed to run for 1 hour under argon atmosphere, during which the reaction was monitored by TLC (petroleum ether:ethyl acetate=4:1, product: $R_f$=0.42). Column chromatography (silica gel 300-400 mesh, petroleum ether:ethyl acetate=4:1) afforded (8R,9S,13S,14S,17R)-17-ethynyl-17-hydroxy-13-methyl-7,8,9,11,12,13,14,15,16,17-decahydro-6H-cyclopenta[a]-3-phenanthroxysulfonyl fluoride [Compound 43] as a white solid (349 mg, 88%) (Scheme 9).

White solid, m.p. 44.9-48.1° C., 349 mg, 88% yield; $^1$H NMR (400 MHz, CDCl$_3$) δ 7.37 (d, J=8.0 Hz, 1H), 7.09 (d, J=8.0 Hz, 1), 7.04 (s, 1H), 2.92-2.89 (m, 2H), 2.61 (s, 1), 2.39-2.25 (m, 3H), 2.06-1.91 (m, 3H), 1.83-1.68 (m, 4H), 1.57-1.34 (m, 4H), 0.89 (s, 3H); $^{13}$C NMR (100 MHz, CDCl$_3$) δ 148.0, 141.0, 139.6, 127.3, 120.6, 117.6, 87.4, 79.7, 74.2, 49.4, 47.0, 43.6, 38.9, 38.7, 32.6, 29.5, 26.7, 26.1, 22.7, 12.7; $^{19}$F NMR (376 MHz, CDCl$_3$) δ 36.8 (s, 1F); GC-MS ($t_R$): 26.6 min; EI-MS (m/z): 378 [M]$^+$.

Embodiment 20

Preparation of (8R,9S,13S,14S)-13-methyl-17-oxo-7,8,9,11,12,13,14,15,16,17-decahydro-6H-cyclopenta[α]-3-phenanthroxysulfonyl fluoride Scheme 20 Preparation of (8R,9S,13S,14S)-13-methyl-17-oxo-7,8,9,11,12,13,14,15,16,17-decahydro-6H-cyclopenta[a]-3-phenanthroxysulfonyl fluoride

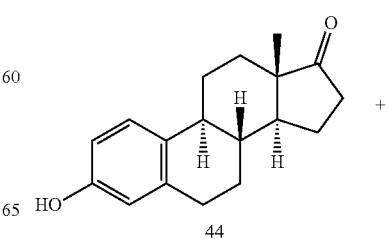

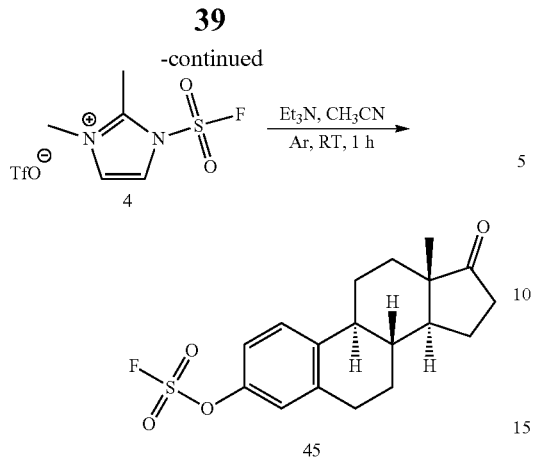

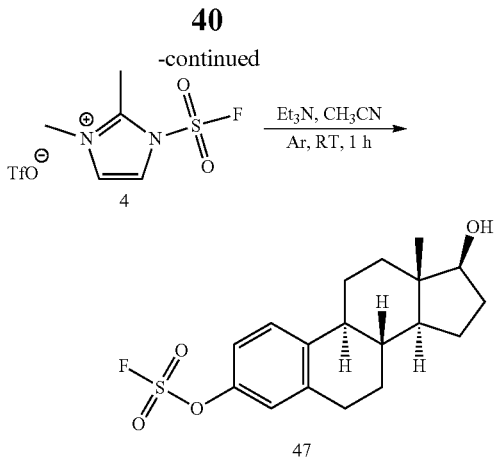

Triethylamine (220 μL, 1.59 mmol) was added to a solution of estrone [Compound 44] (288 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethaesulfonate [Compound 4] (448 mg, 1.27 mmol) in acetonitrile (1 mL) was added in one portion. The reaction was allowed to run for 1 hour under argon atmosphere, dining which the reaction was monitored by TLC (petroleum ether ethyl acetate=4:1, product: $R_f$=0.43). Column chromatography (silica gel 300-400 mesh, petroleum ether:ethyl acetate=4:1) afforded (8R,9S,13S,14S)-13-methyl-17-oxo-7,8,9,11,12,13,14,15,16,17-decahydro-6H-cyclopenta[α]-3-phenanthroxysulfonyl fluoride [Compound 45] as a white solid (295 mg, 80%) (Scheme 0).

White solid, m.p. 108.8-111.3° C. 295 mg, 80% yield; $^1$H NMR (400 MHz, CDCl$_3$) δ 7.37 (d, J=8.0 Hz, 1H), 7.10 (d, J=8.0 Hz, 1H), 7.06 (s, 1H), 2.97-2.94 (m, 2H), 2.56-2.49 (m, 1H), 2.44-2.39 (m, 1), 2.33-2.27 (m, 1H), 2.21-1.98 (m, 4H), 1.69-1.42 (m, 6H), 0.92 (s, 3H); $^{13}$C NMR (100 MHz, CDCl$_3$) δ 220.1, 148.0, 140.5, 139.4, 127.2, 120.5, 117.6, 50.2, 47.7, 43.9, 37.6, 35.6, 31.4, 29.2, 25.9, 25.5, 21.4, 13.6; $^{19}$F NMR (376 MHz, CDCl$_3$) δ 36.9 (s, 1F); GC-MS ($t_R$): 26.1 min; EI-MS (m/z): 352 [M]$^+$; HRMS (EI, m/z): calculated for C$_{18}$H$_{21}$O$_4$FS: 352.1145 [M]$^+$, found: 352.1143;

Triethylamine (220 μL, 1.59 mmol) was added to a solution of β-estradiol[Compound 46] (292 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (448 mg, 1.27 mmol) in acetonitrile (1 mL) was added in one portion. The reaction was allowed to run for 1 hour under argon atmosphere, during which time the reaction was monitored by TLC (petroleum ether:ethyl acetate=4:1, product: $R_f$=0.38). Column chromatography (silica gel 300-400 mesh, petroleum ether:ethyl acetate=4:1) afforded (8R,9S,13S,14S,17S)-17-hydroxy-13-methyl-7,8,9,11,12,13,14,15,16,17-decahydro-6H-cyclopenta[a]-3-phenanthroxysulfonyl fluoride [Compound 47] as a pale yellow solid (305 mg, 82%) (Scheme 1).

Pale yellow solid, m.p. 100.2-104.0° C. 305 mg, 82% yield; $^1$H NMR (400 MHz, CDCl$_3$) δ 7.36 (d, J=8.8 Hz, 1H), 7.08 (d, J=8.0 Hz, 1H), 7.03 (s, 1H), 3.74 (t, J=8.0 Hz, 1H), 2.91-2.88 (m, 2H), 2.34-2.09 (m, 3H), 1.99-1.90 (m, 2H), 1.75-1.68 (m, 1H), 1.57-1.17 (m, 8H), 0.79 (s, 3H); $^{13}$C NMR (100 MHz, CDCl$_3$) δ 147.9, 141.2, 139.7, 127.3, 120.5, 117.5, 81.5, 49.9, 44.0, 43.1, 38.2, 36.5, 30.3, 29.4, 26.7, 26.1, 23.0, 11.0; $^{19}$F NMR (376 MHz, CDCl$_3$) δ 36.8 (s, 1F); GC-MS ($t_R$): 26.0 min; EI-MS (m/z): 354 [M]$^+$; HRMS (EI, m/z): calculated for C$_{18}$H$_{23}$O$_4$FS: 354.1301 [M]$^+$, found: 354.1293.

Embodiment 21

Preparation of (8R,9S,13S,14S,17S)-17-hydroxy-13-methyl-7,8,9,11,12,13,14,15,16,17-decahydro-6H-cyclopenta[a]-3-phenanthroxysulfonyl fluoride Embodiment 22

Preparation of (E)-4-(3,5-dimethoxystyryl)phenoxysulfonyl fluoride

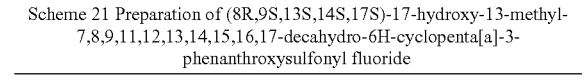

Scheme 21 Preparation of (8R,9S,13S,14S,17S)-17-hydroxy-13-methyl-7,8,9,11,12,13,14,15,16,17-decahydro-6H-cyclopenta[a]-3-phenanthroxysulfonyl fluoride

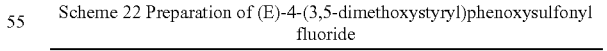

Scheme 22 Preparation of (E)-4-(3,5-dimethoxystyryl)phenoxysulfonyl fluoride

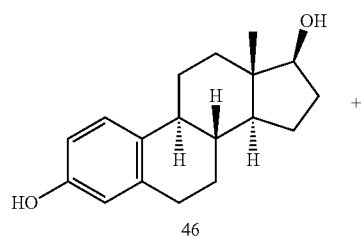

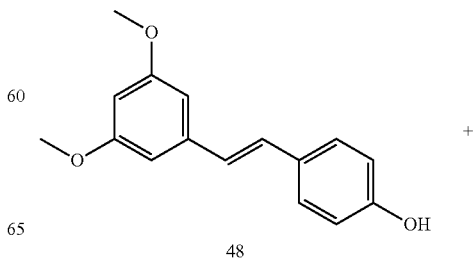

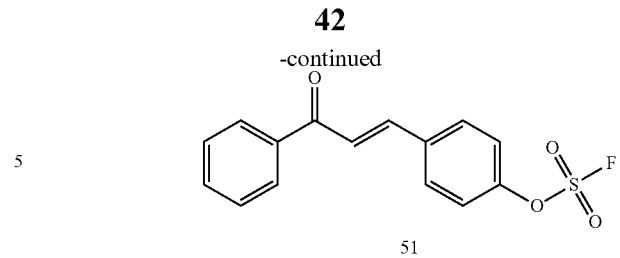

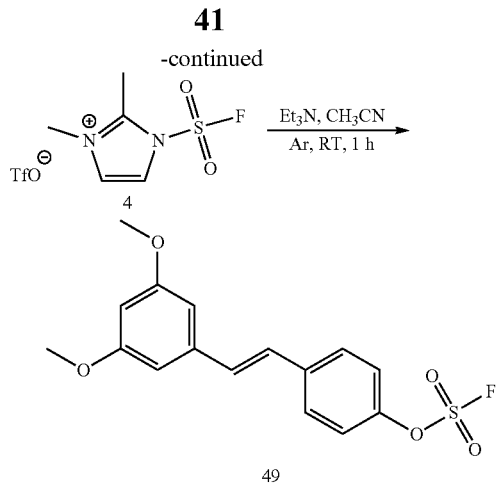

Triethylamine (220 μL, 1.59 mmol) was added to a solution of pterostilbene [Compound 48] (272 mg, 1.04 mmol) in acetonitrile (11 mL) at room temperature. After the mixture was stirred for 10 minutes, a solution of 1-(fluorosulfonyl)-2-3-dimethyl-1H-imidazolium trifluoromethanesulfonate [Compound 4] (448 mg, 1.27 mmol) in acetonitrile (1 mL) was added in one portion. The reaction was allowed to run for 1 hour under argon atmosphere, during which time the reaction was monitored by TLC (petroleum ether:ethyl acetate=4:1, product: $R_f$=0.43). Column chromatography (silica gel 300-400 mesh, petroleum ether:ethyl acetate=4:1, 3:1) afforded (E)-4-(3,5-dimethoxystyryl)phenoxysulfonyl fluoride [compound 49] as a pale yellow solid (309 mg, 87%)(Scheme 2).

Pale yellow solid, m.p. 80.1-81.1° C., 309 mg, 87% yield; $^1$H NMR (400 MHz, CDCl$_3$) δ 7.58 (d, J=8.0 Hz, 2H), 7.33 (d, J=8.0 Hz, 2H), 7.05 (s, 2H), 6.67 (s, 2H), 6.43 (s, 1H), 3.84 (s, 6H); $^{13}$C NMR (100 MHz, CDCl$_3$) δ 161.0, 149.0, 138.5, 137.8, 130.8, 128.1, 126.8, 121.0, 104.8, 100.3, 55.2; $^{19}$F NMR (376 MHz, CDCl$_3$) δ 37.1 (s, 1F); GC-MS (t$_R$): 24.9 min; EI-MS (m/z): 338 [M]$^+$; HRMS (EI, m/z): calculated for C$_{16}$H$_{15}$O$_5$FS: 338.0624 [M]$^+$, found: 338.0619.

Embodiment 23

Preparation of (E)-4-(3-oxo-3-phenylpropenyl)phenylsulfonyl fluoride

Scheme 23 Preparation of (E)-4-(3-oxo-3-phenylpropenyl) phenylsulfonyl fluoride

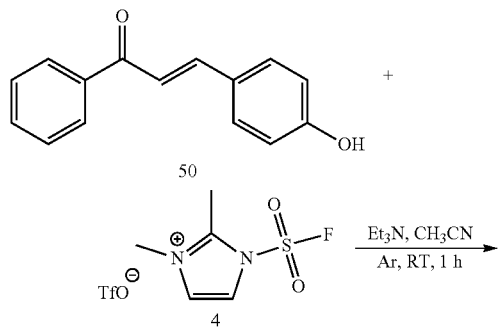

Triethylamine (220 μL, 1.59 mmol) was added to a solution of 4-hydroxychalcone [Compound 50] (241 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (421 mg, 1.28 mmol) in acetonitrile (1 mL) was added in one portion. The reaction was allowed to run for 1 hour under argon atmosphere, during which time the reaction was monitored by TLC (petroleum ether:ethyl acetate=10:1, product: $R_f$=0.42). Column chromatography (silica gel 300-400 mesh, petroleum ether ethyl acetate=10:1) afforded (E)-4-(3-oxo-3-phenylpropenyl)phenylsulfonyl fluoride [compound 51] as a light green solid (262 mg, 82%) (Scheme 3).

Light green solid, m.p. 92.8-94.2° C., 262 mg, 82% yield; $^1$H NMR (400 MHz, CDCl$_3$) δ 8.02 (d, J=8.0 Hz, 2H), 7.81-7.74 (m, 3H), 7.62 (t, J=7.4 Hz, 1H), 7.56-7.51 (m, 3H), 7.41 (d, J=8.0 Hz, 2H); $^{13}$C NMR (100 MHz, CDCl$_3$) δ 150.0, 150.9, 142.2, 137.8, 135.6, 133.3, 130.3, 128.8, 128.6, 124.0, 121.6; $^{19}$F NMR (376 MHz, CDCl$_3$) δ +37.8 (s, 1F); GC-MS (t$_R$): 22.9 mm, EI-MS (m/z): 306 [M]$^+$; HRMS (EI, m/z): calculated for C$_{15}$H$_{11}$O$_4$FS: 306.0362 [M]$^+$, found: 306.0369.

Embodiment 24

Preparation of 5-methyl-3-(-2-pyridyl)-5H-benzo[5,6][1,2]thiazino[3,4-e][1,2,3]oxathiazine-4(3H)-one-2,2,6,6-tetraoxide Scheme 24 Preparation of 5-methyl-3-(-2-pyridyl)-5H-benzo[5,6][1,2]thiazino[3,4-e][1,2,3]oxathiazine-4(3H)-one-2,2,6,6-tetraoxide

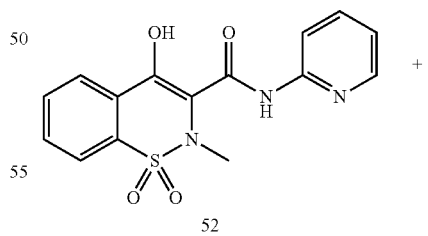

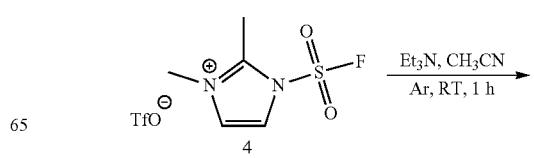

-continued

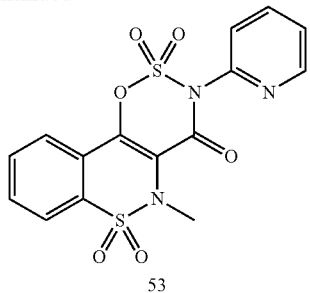

53

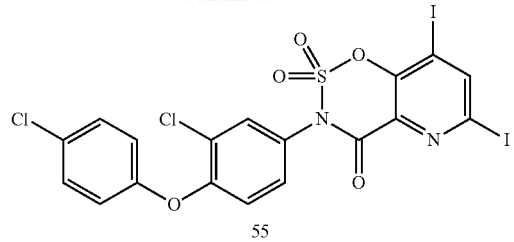

55

Triethylamine (132 µL, 0.95 mmol) was added to a solution of piroxicam [compound 52] (210 mg, 0.62 mmol) in acetonitrile (1 mL) at room temperature. After the mixture was stirred for 10 minutes, a solution of 1-(fluorosulfonyl)-2-3-dimethyl-1H-imidazolium trifluoromethaesulfonate [compound 4] (268 mg, 0.76 mmol) in acetonitrile (1 mL) was added in one portion. The reaction was allowed to run for 1 hour under argon atmosphere, during which time the reaction was monitored by TLC (petroleum ether:ethyl acetate=1:1, product: $R_f$=0.42). Column chromatography (silica gel 300-400 mesh, petroleum ether:ethyl acetate=1:1) afforded 5-methyl-3-(-2-pyridyl)-5H-benzo[5.6][1,2]thiazino[3,4-e][1,2,3]oxathiazine-4(3H)-one-2,2,6,6-tetraoxide [compound 53] as a pale yellow solid (138 mg, 56%) (Scheme 24).

Pale yellow solid, m.p. 197.3-200.9° C., 138 mg, 56% yield; $^1$H NMR (400 MHz, CDCl$_3$) δ 8.69 (s, 1H), 8.03 (t, J=8.0 Hz 2H), 7.96 (t, J=8.0 Hz, 1H), 7.89 (s, 2H), 7.50-7.48 (m, 2H), 3.29 (s, 3H); $^{13}$C NMR (100 MHz, CDCl$_3$) δ 157.1, 149.9, 146.7, 145.5, 139.3, 135.1, 134.2, 133.1, 126.1, 125.2, 124.4, 123.5, 123.5, 120.3, 36.6; $^{19}$F NMR (376 MHz, CDCl$_3$) no signal; LC-MS ($t_R$): 2.7 min; ESI-MS (m/z): 394.03 [MH]$^+$; HRMS (ESI, m/z): calculated for C$_{15}$H$_{12}$O$_6$N$_3$S$_2$: 394.0162 [MH]$^+$, found: 394.0171.

Embodiment 25

Preparation of 3-(3-chloro-4-(4-chlorophenoxy)phenyl)-6-8-diiodobenzo[e][1,2,3]oxathiazine-4(3H)-one-2,2-dioxide Triethylamine (85 µL, 0.61 mmol) was added to a solution of rafoxanide [Compound 54] (256 mg, 0.40 mmol) in acetonitrile (1 mL) at room temperature. After the mixture was stirred for 10 minutes, a solution of 1-(fluorosulfonyl)-2-3-dimethyl-1H-imidazolium trifluoromethaesulfonate [Compound 4] (172 mg, 0.49 mmol) in acetonitrile (1 mL) was added in one portion. The reaction was allowed to run for 1 hour under argon atmosphere, during which time the reaction was monitored by TLC (petroleum ether:ethyl acetate=10:1, product: $R_f$=0.57). Column chromatography (silica gel 300-400 mesh, petroleum ether:ethyl acetate=30:1) afforded 3-(3-chloro-4-(4-chlorophenoxy)phenyl)-6-8-diiodobenzo[e][1,2,3]oxathiazine-4(3H)-one-2,2-dioxide [compound 55] as a white solid (154 mg, 56%) (Scheme 25).

White solid, m.p. 183.0-183.8° C., 154 mg, 56% yield; $^1$H NMR (400 MHz, CDCl$_3$) δ 8.48 (d, J=2.0 Hz, 1H), 8.42 (d, J=2.0 Hz, 1H), 7.55 (d, J=2.8 Hz, 1H), 7.39-7.38 (m, 1H), 7.37-7.35 (m, 1H), 7.27-7.24 (m, 1H), 7.04-6.98 (m, 3H); $^{13}$C NMR (100 MHz, CDCl$_3$) δ 158.7, 155.1, 154.1, 153.6, 150.2, 139.4, 132.0, 130.3, 130.1, 129.2, 126.2, 126.0, 120.8, 119.6, 119.1, 91.6, 86.7; $^{19}$F NMR (376 MHz, CDCl$_3$) no signal; HRMS (DART, m/z): calculated for C$_{19}$H$_{10}$O$_5$NCl$_2$I$_2$S: 687.7741 [MH]$^+$, found: 687.7732.

Embodiment 26

Preparation of (S)-4-ethyl-4-hydroxy-3,14-dioxo-3,4,12,14-tetrahydro-1H-pyrano[3',4': 6,7]indolizino[1,2-b]-9-quinolinylsulfonyl fluoride Scheme 26 Preparation of (S)-4-ethyl-4-hydroxy-3, 14-dioxo-3, 4, 12, 14-tetrahydro-1H-pyrano[3', 4', 6, 7]indolizino[1, 2-b]-9-quinolinylsulfonyl fluoride

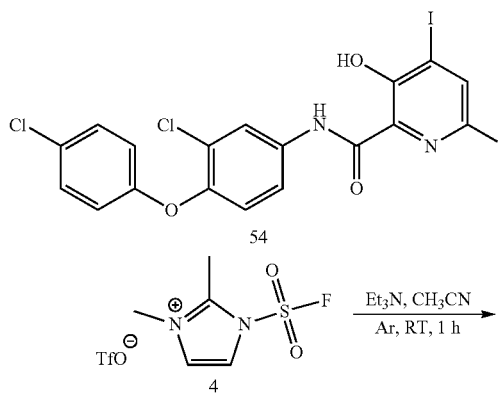

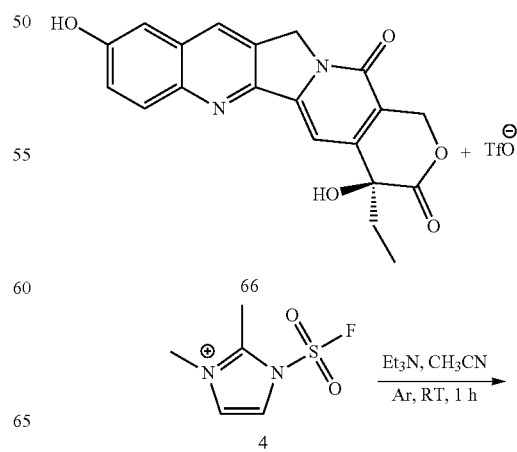

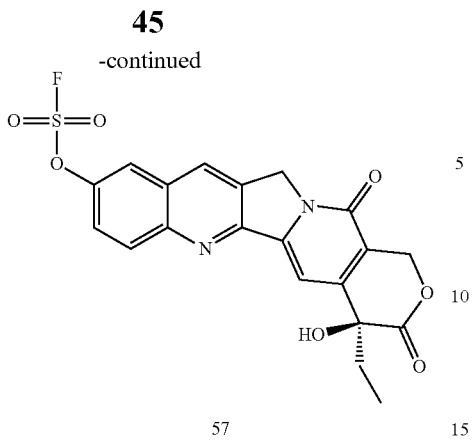

57

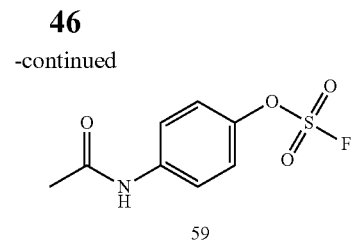

59

Triethylamine (440 μL, 3.17 mmol) was added to a solution of (S)-10-hydroxycamptothecin [Compound 56] (194 mg, 0.52 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (840 mg, 2.56 mmol) in acetonitrile (1 mL) was added in one portion. The reaction was allowed to run for 1 hour under argon atmosphere, during which time the reaction was monitored by TLC (petroleum ether:ethyl acetate=1:1, product: $R_f$=0.11). Column chromatography (silica gel 300-400 mesh, petroleum ether:ethyl acetate=1:1) afforded (S)-4-ethyl-4-hydroxy-3,14-dioxo-3,4,12,14-tetrahydro-1H-pyrano[3',4': 6,7]indolizino[1,2-b]-9-quinolinylsulfonyl fluoride [compound 57] as a light green solid (143 mg, 61%) (Scheme 6).

Light green solid, m.p. 227.6-229.6° C., 143 mg, 61% yield; $^1$H NMR (400 MHz, DMSO-d$_6$) δ 8.80 (s, 1H), 8.48 (d, J=2.4 Hz, 1H), 8.35 (d, J=9.2 Hz, 1H), 8.04 (dd, J=9.2, 2.4 Hz, 1H), 7.38 (s, 1H), 6.55 (s, 1H), 5.43 (s, 2H), 5.32 (s, 2H), 1.92-1.82 (m, 2H), 0.89 (t, J=7.2 Hz, 3H); $^{13}$C NMR (100 MHz, DMSO-d$_6$) δ 172.4, 156.6, 154.1, 149.9, 147.4, 146.8, 144.7, 132.1, 131.9, 131.1, 128.0, 123.5, 120.0, 119.7, 97.2, 72.3, 65.2, 50.2, 30.4, 7.8; $^{19}$F NMR (376 MHz, DMSO-d$_6$) δ +39.7 (s, 1F); LC-MS (t$_R$): 1.4 min; ESI-MS (m/z): 447.17 [MH]$^+$; HRMS (DART, m/z): calculated for C$_2$H$_{16}$O$_7$N$_2$FS: 447.0657 [MH]$^+$, found: 447.0658.

Embodiment 27

Preparation of 4-acetamidophenoxysulfonyl fluoride

Triethylamine (220 μL, 1.59 mmol) was added to a solution of paracetamol [Compound 58] (161 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (420 mg, 1.28 mmol) in acetonitrile (1 mL) was added in one portion. The reaction was allowed to run for 1 hour under argon atmosphere, during which time the reaction was monitored by TLC (petroleum ether:ethyl acetate=1:1, product: $R_f$=0.47). Column chromatography (silica gel 300-400 mesh, petroleum ether:ethyl acetate=1:1) afforded 4-acetamidophenoxysulfonyl fluoride [compound 59] as a pale yellow solid (238 mg, 98%) (Scheme 7).

Pale yellow solid, m.p. 150.3-152.0° C. 238 mg, 98% yield; $^1$H NMR (400 MHz, DMSO-d$_6$) δ 10.24 (s, 1H), 7.75 (d, J=9.2 Hz, 2H), 7.51 (d, J=9.2 Hz, 2H), 2.06 (s, 3H); $^{13}$C NMR (100 MHz, DMSO-d$_6$) δ 168.7, 144.5, 139.9, 121.5, 120.4, 24.0; $^{19}$F NMR (376 MHz, DMSO-d$_6$) δ +38.3 (s, 1F); LC-MS (t$_R$): 1.36 min; ESI-MS (m/z): 234.11 [MH]$^+$; HRMS (DART, m/z): calculated for C$_8$H$_9$O$_4$NFS: 234.0231 [MH]$^+$, found: 234.0230.

Embodiment 28

Preparation of (E)-2-((2-fluorosulfonyloxy)phenyl)azo)phenoxysulfonyl fluoride

Scheme 8 Preparation of(E)-2-((2-fluorosulfonyloxy)phenyl)azo)phenoxysulfnoyl fluoride

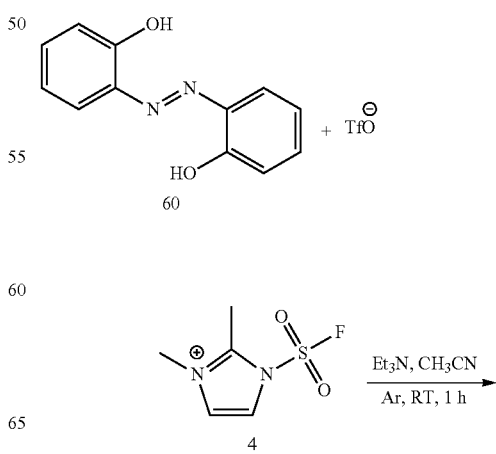

Scheme 27 Preparation of 4-acetamidophenoxysulfonyl fluoride

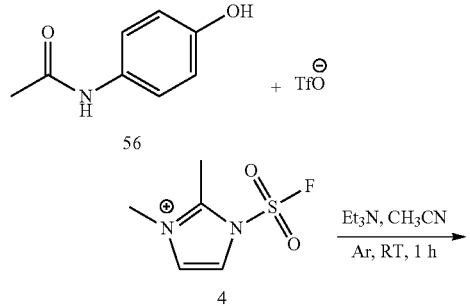

-continued

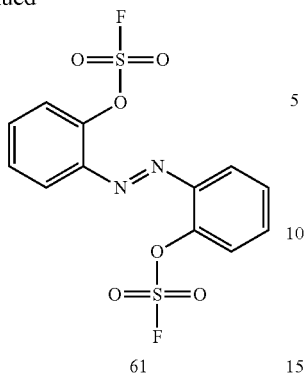

61

-continued

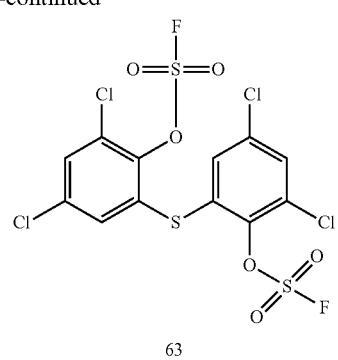

63

Triethylamine (660 μL, 4.76 mmol) was added to a solution of 2,2-dihydroxyazobenzene [Compound 60] (114 mg, 0.52 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (1.267 g, 3.86 mmol) in acetonitrile (1 mL) was added in one portion. The reaction was allowed to run for 1 hour under argon atmosphere, during which time the reaction was monitored by TLC (petroleum ether:ethyl acetate=10:1, product: $R_f$=0.54). Column chromatography (silica gel 300-400 mesh, petroleum ether:ethyl acetate=10:1) afforded (E)-2-((2-fluorosulfonyloxy)phenyl)azo)phenoxysulfonyl fluoride [compound 61] as a red solid (168 mg, 85%) (Scheme 8).

Red solid, m.p. 116.5-118.3° C., 168 mg, 85% yield; $^1$H NMR (400 MHz, CDCl$_3$) δ 7.94 (dd, J=8.4, 1.6 Hz, 2H), 7.68-7.64 (m, 2H), 7.58-7.54 (m, 4); $^{13}$C NMR (100 MHz, CDCl$_3$) δ 148.7, 143.8, 133.8, 129.7, 122.8, 118.1; $^{19}$F NMR (376 MHz, CDCl$_3$) δ +39.6 (s, 1F); LC-MS ($t_R$): 1.79 min; ESI-MS (m/z): 379.09 [MH]$^+$; HRMS (DART, m/z): calculated for C$_{12}$H$_9$O$_6$N$_2$F$_2$S$_2$: 378.9865 [MH]$^+$, found: 378.9862.

Embodiment 29

Preparation of thiobis(4,6-dichloro-2,1-phenyl)dioxysulfonyl fluoride

Scheme 29 Preparation of thiobis(4, 6-dichloro-2, 1-phenyl) dioxysulfonyl fluoride

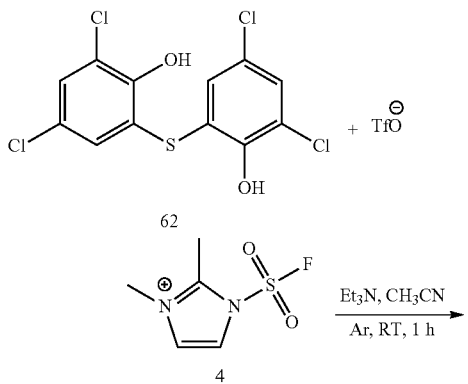

Triethylamine (440 μL, 3.17 mmol) was added to a solution of bithionol [Compound 62] (382 mg, 1.04 mmol) at room temperature. After the mixture was stirred for 10 minutes, a solution of 1-(fluorosulfonyl)-2-3-dimethyl-1H-imidazolium trifluoromethanesulfonate [Compound 4] (840 mg, 2.56 mmol) in acetonitrile (1 mL) was added in one portion. The reaction was allowed to run for 1 hour under argon atmosphere, during which time the reaction was monitored by TLC (petroleum ether:ethyl acetate=10:1, product: $R_f$=0.62). Column chromatography (silica gel 300-400 mesh, petroleum ether:ethyl acetate=10:1) afforded thiobis(4,6-dichloro-2,1-phenyl)dioxysulfonyl fluoride [compound 63] as a light green jelly (507 mg, 94%) (Scheme 29).

Light green jelly, 507 mg, 94% yield; $^1$H NMR (400 MHz, CDCl$_3$) δ 7.55 (d, J=2.4 Hz, 2H), 7.24 (d, J=2.4 Hz, 2H); $^{13}$C NMR (100 MHz, CDCl$_3$) δ 144.6, 135.7, 132.2, 131.8, 130.9, 130.1; $^{19}$F NMR (376 MHz, CDCl$_3$) δ +48.6 (s, 2F); HRMS (DART, m/z): calculated for C$_{12}$H$_4$O$_6$Cl$_4$F$_2$S$_3$: 517.7887 [M]$^+$, found: 517.7881.

Embodiment 30

Preparation of 8-acetyl-4-methyl-2-oxo-2H-benzopyran-7-oxysulfonyl fluoride

Scheme 30 Preparation of 8-acetyl-4-methyl-2-oxo-2H-benzopyran-7-oxysulfonyl fluoride

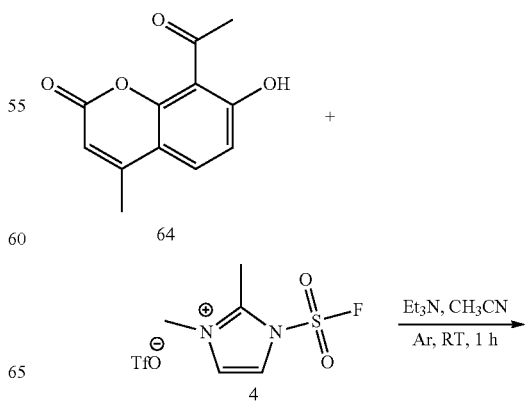

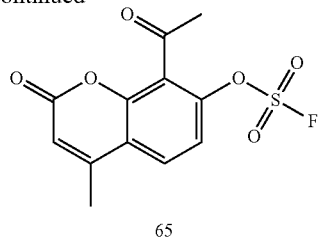

Triethylamine (220 μL, 1.59 mmol) was added to a solution of 8-acetyl-7-hydroxy-4-methylcoumarin [compound 64] (232 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [compound 4] (420 mg, 1.28 mmol) in acetonitrile (1 mL) was added in one portion. The reaction was allowed to run for 1 hour under argon atmosphere, during which time the reaction was monitored by TLC (petroleum ether:ethyl acetate=4:1, product: $R_f$=0.16). Column chromatography (silica gel 300-400 mesh, petroleum ether:ethyl acetate=4:1) afforded 8-acetyl-4-methyl-2-oxo-2H-benzopyran-7-oxysulfonyl fluoride [compound 65] as a white solid (253 mg, 81%) (Scheme 30).

White solid, m.p. 163.8-165.2° C., 253 mg, 81% yield; $^1$H NMR (400 MHz, CDCl$_3$) δ 7.77 (d, J=8.8 Hz, 1H), 7.37 (dd, J=8.8, 1.2 Hz, 1H), 6.39 (d, J=0.8 Hz, 1H), 2.73 (s, 3H), 2.48 (s, 3H); $^{13}$C NMR (100 MHz, CDCl$_3$) δ 195.5, 158.2, 151.4, 151.1, 147.0, 127.4, 123.9, 120.6, 117.4, 116.3, 32.4, 19.0; $^{19}$F NMR (376 MHz, CDCl$_3$) δ +40.6 (s, 1F); GC-MS ($t_R$): 20.9 min, EI-MS (m/z): 300 [M]$^+$; HRMS (EI, m/z): calculated for C$_2$H$_9$O$_6$FS: 300.0104 [M]$^+$, found: 300.0100.

Embodiment 31

Preparation of 2-oxo-2H-6-benzopyranyloxysulfonyl fluoride

Scheme 31 Preparation of 2-oxo-2H-6-benzopyranyloxysulfonyl fluoride

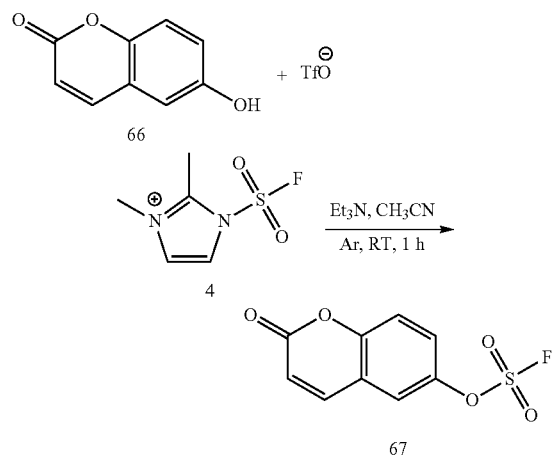

Triethylamine (220 μL, 1.59 mmol) was added to a solution of 6-hydroxycoumarin [Compound 66] (173 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (448 mg, 1.27 mmol) in acetonitrile (1 mL) was added in one portion. The reaction was allowed to run for 1 hour under argon atmosphere, during which time the reaction was monitored by TLC (petroleum ether:ethyl acetate=1:1, product: $R_f$=0.53). Column chromatography (silica gel 300-400 mesh, petroleum ether ethyl acetate=1:1) afforded 2-oxo-2H-6-benzopyranyloxysulfonyl fluoride [compound 67] as a yellow solid (229 mg, 90%) (Scheme 29).

Yellow solid, m.p. 85.3-87.9° C., 229 mg, 90% yield; $^1$H NMR (400 MHz, CDCl$_3$) δ 7.72 (d, J=9.6 Hz, 1H), 7.51 (s, 2H), 7.45 (d, J 10.0 Hz, 1H), 6.56 (d, J=10.0 Hz, 1H); $^{13}$C NMR (100 MHz, CDCl$_3$) δ 159.4, 153.0, 145.4, 142.1, 124.1, 120.0, 119.8, 118.9, 118.4; $^{19}$F NMR (376 MHz, CDCl$_3$) δ 37.2 (s, 1F); GC-MS ($t_R$): 16.8 min; EI-MS (m/z): 244 [M]$^+$; HRMS (EI, m/z): calculated for C$_9$H$_5$O$_5$FS: 243.9842 [M]$^+$, found: 243.9839.

Embodiment 32

Preparation of 1,3,5-phenyltrioxysulfonyl fluoride

Sheme 32 Preparation of 1, 3, 5-phenyltrioxysulfonyl fluoride

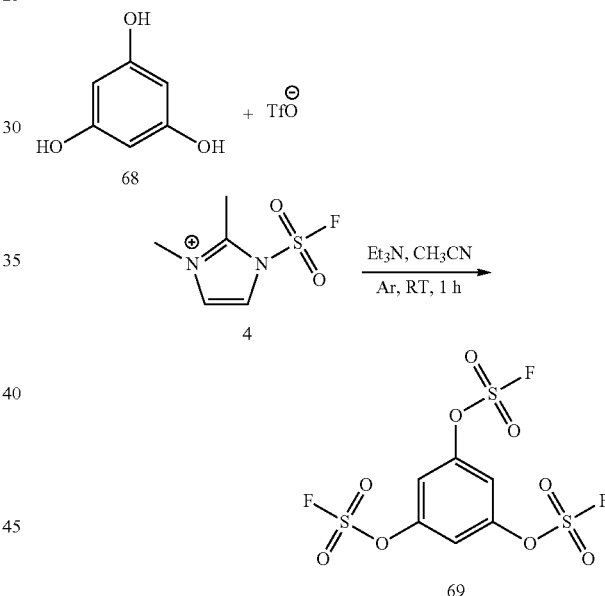

Triethylamine (660 μL, 4.76 mmol) was added to a solution of phloroglucinol [compound 68] (133 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [compound 4] (1.344 g, 3.81 mmol) in acetonitrile (1 mL) was added in one portion. The reaction was allowed to run for 1 hour under argon atmosphere, during which time the reaction was monitored by TLC (petroleum ether:ethyl acetate=10:1, product: $R_f$=0.45). Column chromatography (silica gel 300-400 mesh, petroleum ether:ethyl acetate=30:1) afforded 1,3,5-phenyltrioxysulfonylfluoride [compound 69] (223 mg, 57%) as a white solid (Scheme 2).

White solid, m.p. 95.7-97.2° C., 223 mg, 57% yield; $^1$H NMR (400 MHz, CDCl$_3$) δ 7.53 (s, 3H); $^{13}$C NMR (100 MHz, CDCl$_3$) δ 150.3, 115.7; $^{19}$F NMR (376 MHz, CDCl$_3$) δ 39.6 (s, 3F); GC-MS ($t_R$): 12.3 min; EI-MS (m/z): 372 [M]$^+$.

Embodiment 33

Preparation of methyl 2-(fluorosulfonyloxy)benzoate

Scheme 33 Preparation of 2-(fluorosulfonyloxy)methyl benzoate

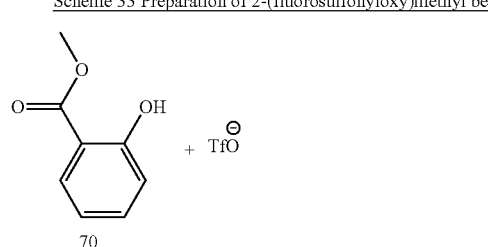

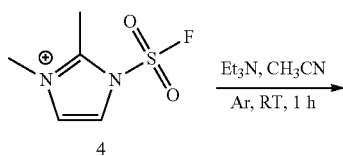

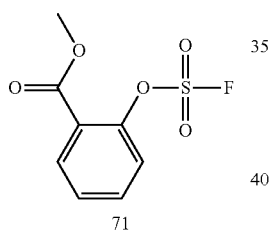

Triethylamine (220 μL, 1.59 mmol) was added to a solution of methyl salicylate [Compound 70] (135 μL, 1.03 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (448 mg, 1.27 mmol) in acetonitrile (1 mL) was added in one portion. The reaction was allowed to run for 1 hour under argon atmosphere, during which time the reaction was monitored by TLC (petroleum ether:ethyl acetate=10:1, product: $R_f$=0.38). Column chromatography (silica gel 300-400 mesh, petroleum ether:ethyl acetate=30:1, 20:1) afforded methyl 2-(fluorosulfonyloxy)benzoate [compound 71] as a colorless liquid (196 mg, 81%) (Scheme 3).

Colorless liquid, 196 mg, 81% yield; $^1$H NMR (400 MHz, CDCl$_3$) δ 8.12 (d, J=8.0 Hz, 1H), 7.67 (t, J=8.0 Hz, 1H), 7.52 (t, J=8.0 Hz, 1H), 7.42 (d, J=8.0 Hz, 1H), 3.98 (s, 3H); $^{13}$C NMR (100 MHz, CDCl$_3$) δ 163.8, 148.5, 134.5, 132.9, 128.9, 123.8, 122.5, 52.7; $^{19}$F NMR (376 MHz, CDCl$_3$) δ 41.2 (s, 1F); GC-MS (t$_R$): 11.8 min; EI-MS (m/z): 234 [M]$^+$; HRMS (EI, m/z): calculated for C$_8$H$_7$O$_5$FS: 233.9998 [M]$^+$, found: 233.9995.

Embodiment 34

Preparation of 5,7-dichloro-2-methyl-quinoline-8-oxysulfonyl fluoride

Scheme 34 Preparation of 5, 7-dichloro-2-methyl-quinoline-8-oxysulfonyl fluoride

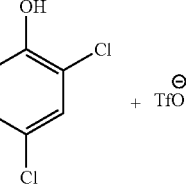

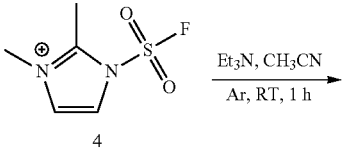

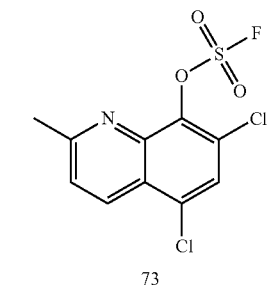

Triethylamine (220 μL, 1.59 mmol) was added to a solution of 5,7-dichloro-8-hydroxyquinaldine [compound 72] (243 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [compound 4] (420 mg, 1.28 mmol) in acetonitrile (1 mL) was added in one portion. The reaction was allowed to run for 1 hour under argon atmosphere, during which time the reaction was monitored by TLC (petroleum ether:ethyl acetate=10:1, product: $R_f$=0.64). Column chromatography (silica gel 300-400 mesh, petroleum ether ethyl acetate=10:1) afforded 5,7-dichloro-2-methyl-quinoline-8-oxysulfonyl fluoride [compound 73] as a light green solid (314 mg, 97%) (Scheme 34).

Light green solid, m.p. 64.6-66.2° C., 314 mg, 97% yield; $^1$H NMR (400 MHz, CDCl$_3$) δ 8.41 (d, J=8.8 Hz, 1H), 7.65 (s, 1H), 7.49 (d, J=8.8 Hz, 1H), 2.81 (s, 3H); $^{13}$C NMR (100 MHz, CDCl$_3$) δ 162.8, 141.4, 133.2, 131.9, 127.6, 126.4, 124.7, 124.4, 25.6; $^{19}$F NMR (376 MHz, CDCl$_3$) δ +47.2 (s, 1F); LC-MS (t$_R$): 1.8 min; ESI-MS (m/z): 309.92 [MH]$^+$; HRMS (DART, m/z): calculated for C$_{10}$H$_7$O$_3$NCl$_2$FS: 309.9502 [MH]$^+$, found: 309.9502.

Embodiment 35

Preparation of 5-nitro-quinoline-8-oxysulfonyl fluoride

Scheme 35 Preparation of 5-nitro-quinoline-8-oxulfonyl fluoride

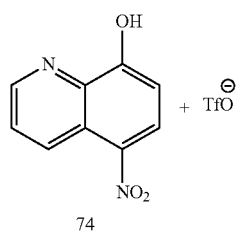

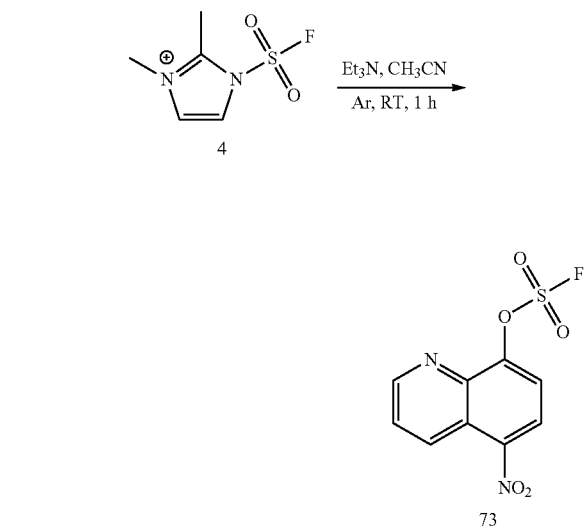

Triethylamine (220 µL, 1.59 mmol) was added to a solution of 5-nitro-8-hydroxyquinoline [Compound 74] (207 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (420 mg, 1.28 mmol) in acetonitrile (1 mL) was added in one portion. The reaction was allowed to run for 1 hour under argon atmosphere, during which time the reaction was monitored by TLC (petroleum ether:ethyl acetate=1:1, product: $R_f$=0.70). Column chromatography (silica gel 300-400 mesh, petroleum ether:ethyl acetate=1:1) afforded 5-nitro-quinoline-8-oxysulfonyl fluoride [compound 75] as a light green solid (281 mg, 99%) (Scheme 35).

Light green solid, m.p. 86.9-87.9° C., 281 mg, 99% yield; $^1$HNMR (400 MHz, CDCl$_3$) δ 9.18 (dd, J=4.2, 1.4 Hz, 1H), 9.06 (dd, J=8.9, 1.4 Hz, 1H), 8.46 (d, J=8.4 Hz, 1H), 7.87 (d, J=8.4 Hz, 1H), 7.81 (dd, J=8.9, 4.2 Hz, 1H); $^{13}$C NMR (100 MHz, CDCl$_3$) δ 152.9, 149.5, 145.0, 140.6, 132.4, 125.5, 124.5, 123.1, 120.0; $^{19}$F NMR (376 MHz, CDCl$_3$) δ +42.1 (s, 1F); LC-MS ($t_R$): 1.5 min; ESI-MS (m/z): 273.01 [MH]$^+$; HRMS (DART, m/z): calculated for C$_9$H$_6$O$_5$N$_2$FS: 272.9976 [MH]$^+$, found: 272.9975.

Embodiment 36

Preparation of 4-allyl-2-methoxyphenoxysulfonyl fluoride

Scheme 36 Preparation of 4-allyl-2-methoxyphenoxysulfonyl fluoride

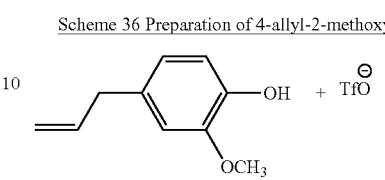

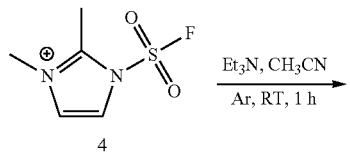

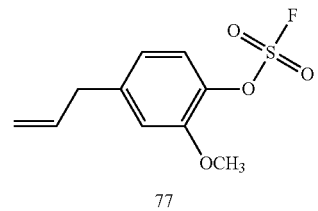

Triethylamine (220 µL, 1.59 mmol) was added to a solution of eugenol [Compound 76] (163 µL, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (448 mg, 1.27 mmol) in acetonitrile (1 mL) was added in one portion. The reaction was allowed to run for 1 hour under argon atmosphere, during which time the reaction was monitored by TLC (petroleum ether ethyl acetate=10:1, product: $R_f$=0.66). Column chromatography (silica gel 300-400 mesh, petroleum ether:ethyl acetate=30:1) afforded 4-allyl-2-methoxyphenoxysulfonyl fluoride [compound 77] as a colorless liquid (247 mg, 96%) (Scheme 36).

Colorless liquid, 247 ng, 96% yield; $^1$H NMR (400 MHz, CDCl$_3$) δ 7.22 (d, J=8.0 Hz, 1H), 6.86 (s, 1H), 6.81 (d, J=8.0 Hz, 1H), 5.99-5.89 (m, 1H), 5.14 (s, 1H), 5.11 (d, J=8.0 Hz, 1H), 3.90 (s, 3H), 3.40 (d, J=8.0 Hz, 2H); $^{13}$C NMR (100 MHz, CDCl$_3$) δ 151.0, 142.4, 137.3, 136.3, 122.1, 120.8, 116.8, 113.7, 56.1, 40.0; $^{19}$F NMR (376 MHz, CDCl$_3$) δ 38.9 (s, 1F); GC-MS ($t_R$): 13.7 mm; EI-MS (m/z): 246 [M]$^+$.

Embodiment 37

Preparation of 4-formyl-2-methoxyphenoxysulfonyl fluoride

Scheme 37 Preparation of 4-formyl-2-methoxyphenoxysulfonyl fluoride

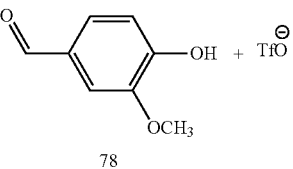

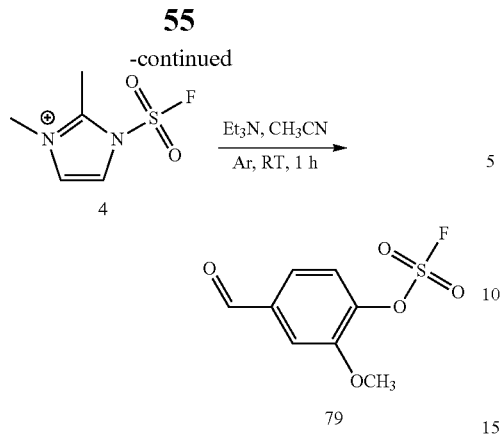

Triethylamine (220 μL, 1.59 mmol) was added to a solution of vanillin [Compound 78](162 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (448 mg, 1.27 mmol) in acetonitrile (1 mL) was added in one portion. The reaction was allowed to run for 1 hour under argon atmosphere, during which time the reaction was monitored by TLC (petroleum ether ethyl acetate=10:1, product: $R_f$=0.26). Column chromatography (silica gel 300-400 mesh, petroleum ether ethyl acetate=20:1, 10:1) afforded 4-formyl-2-methoxyphenoxysulfonyl fluoride [compound 79] as a pale yellow solid (230 mg, 94%) (Scheme 37).

Pale yellow solid, m.p. 50.8-51.8° C., 230 mg, 94% yield; $^1$H NMR (400 MHz, CDCl$_3$) δ 10.00 (s, 1H), 7.58 (s, 1H), 7.52 (t, J=10.0 Hz, 2H), 4.01 (s, 3H); $^{13}$C NMR (100 MHz, CDCl$_3$) δ 190.4, 152.0, 142.7, 137.1, 123.8, 123.1, 112.2, 56.5; $^{19}$F NMR (376 MHz, CDCl$_3$) δ 40.5 (s, 1F); GC-MS ($t_R$): 13.4 min; EI-MS (m/z): 234 [M]$^+$.

Embodiment 38

Preparation of methyl 4-fluorosulfonyloxybenzoate

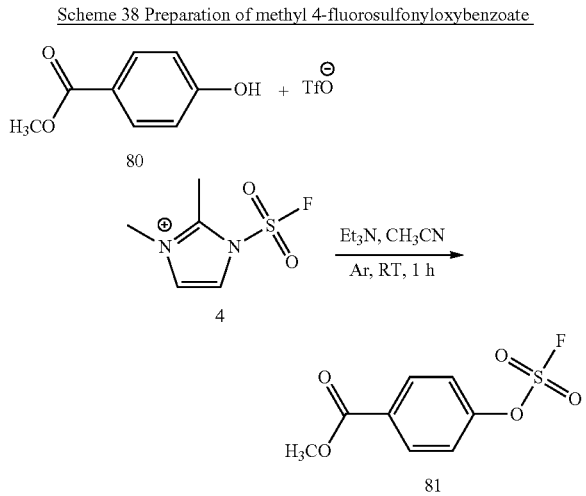

Triethylamine (220 μL, 1.59 mmol) was added to a solution of methyl 4-hydroxybenzoate [Compound 80] (160 mg, 1.04 mmol) in acetonitrile (11 mL) at room temperature. After the mixture was stirred for 10 minutes, a solution of 1-(fluorosulfonyl)-2-3-dimethyl-1H-imidazolium trifluoromethanesulfonate [Compound 4] (448 mg, 1.27 mmol) in acetonitrile (1 mL) was added in one portion. The reaction was allowed to run for 1 hour under argon atmosphere, during which time the reaction was monitored by TLC (petroleum ether:ethyl acetate=10:1, product: $R_f$=0.43). Column chromatography (silica gel 300-400 mesh, petroleum ether ethyl acetate=30:1) afforded methyl 4-fluorosulfonyloxybenzoate [compound 81] as a colorless liquid (201 mg, 82%) (Scheme 38).

Colorless liquid, 201 mg, 82% yield; $^1$H NMR (400 MHz, CDCl$_3$) δ 8.17 (d, J=8.0 Hz, 2H), 7.42 (d, J=8.0 Hz, 2H), 3.95 (s, 3H); $^{13}$C NMR (100 MHz, CDCl$_3$) δ 165.4, 152.9, 132.1, 130.7, 121.0, 52.6; $^{19}$F NMR (376 MHz, CDCl$_3$) δ 38.2 (s, 1F); GC-MS ($t_R$): 12.2 min; EI-MS (m/z): 234 [M]$^+$; HRMS (EI, m/z): calculated for C$_8$H$_7$O$_5$FS: 233.9998 [M]$^+$, found: 233.9997.

Embodiment 39

Preparation of 2-ethyl-6-methylpyridine-3-oxysulfonyl fluoride

Scheme 39 Preparation of 2-ethyl-6-methylpyridine-3-oxysulfonyl fluoride

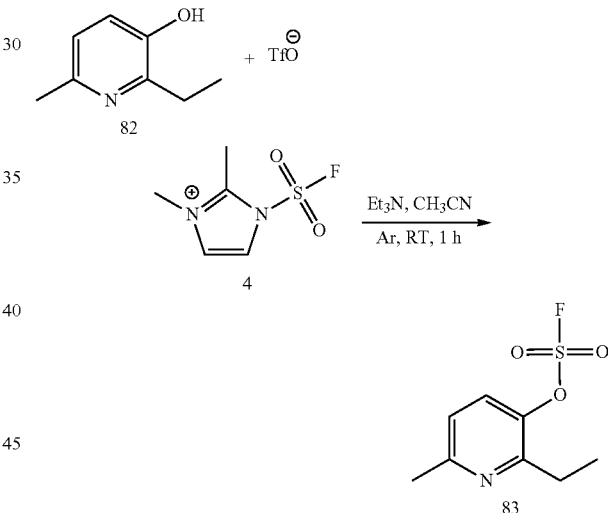

Triethylamine (220 μL, 1.59 mmol) was added to a solution of 2-ethyl-6-methyl-3-hydroxy-pyridine [compound 82] (146 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [compound 4] (448 mg, 1.27 mmol) in acetonitrile (1 mL) was added in one portion. The reaction was allowed to run for 1 hour under argon atmosphere, during which time the reaction was monitored by TLC (petroleum ether:ethyl acetate=10:1, product: $R_f$=0.59). Column chromatography (silica gel 300-400 mesh, petroleum ether:ethyl acetate=30:1) afforded 2-ethyl-6-methylpyridine-3-oxysulfonyl fluoride [compound 83] as a colorless liquid (154 mg, 67%) (Scheme 39).

Colorless liquid, 154 mg, 67% yield; $^1$H NMR (400 MHz, CDCl$_3$) δ 7.51 (d, J=8.0 Hz, 1H), 7.09 (d, J=8.0 Hz, 1H), 2.88 (q, J=14.0 Hz, 2H), 2.57 (s, 3H), 1.31 (t, J=8.0 Hz, 3H); $^{13}$C NMR (100 MHz, CDCl$_3$) δ 158.6, 154.9, 143.6, 128.7, 122.1, 25.6, 24.1, 12.7; $^{19}$F NMR (376 MHz, CDCl$_3$) δ 39.1 (s); GC-MS (t$_R$): 9.3 min: EI-MS (m/z): 219 [M]$^+$; HRMS (EI, m/z): calculated for C$_8$H$_{10}$NO$_3$FS: 219.0365 [M]$^+$, found: 219.0371.

Embodiment 40

Preparation of 2-isopropyl-5-methylphenoxysulfonyl fluoride

Scheme 40 Preparation of 2-isopropyl-5-methylphenoxysulfonyl fluoride

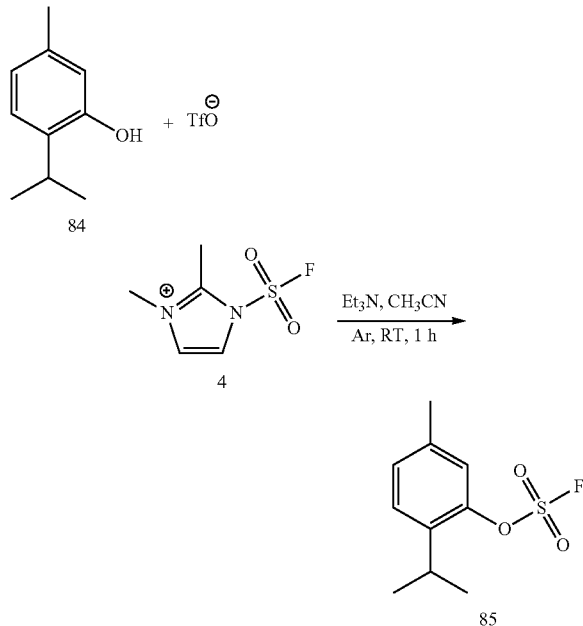

Triethylamine (220 μL, 1.59 mmol) was added to a solution of thymol [compound 84](158 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [compound 4] (448 mg, 1.27 mmol) in acetonitrile (1 mL) was added in one portion. The reaction was allowed to run for 1 hour under argon atmosphere, during which time the reaction was monitored by TLC (petroleum ether:ethyl acetate=10:1, product: R$_f$=0.76). Column chromatography (silica gel 300-400 mesh, petroleum ether:ethyl acetate=30:1) afforded 2-isopropyl-5-methylphenoxysulfonyl fluoride [compound 85] as a colorless liquid (182 mg, 75%) (Scheme 40).

Colorless liquid, 182 mg, 75% yield; $^1$H NMR (400 MHz, CDCl$_3$) δ 7.28 (d, J=8.0 Hz, 1H), 7.17 (d, J=8.0 Hz, 1H), 7.11 (s, 1H), 3.25 (sept, J=6.6 Hz, 1H), 2.36 (s, 3H), 1.24 (d, J=8.0 Hz, 6H); $^{13}$C NMR (100 MHz, CDCl$_3$) δ 147.9, 137.9, 137.6, 129.8, 127.7, 121.1, 26.8, 23.2, 20.8; $^{19}$F NMR (376 MHz, CDCl$_3$) δ 38.9 (s, 1F); GC-MS (t$_R$): 10.7 min; EI-MS (m/z): 232 [M]$^+$.

Embodiment 41

Preparation of 3-nitrophenoxysulfonyl fluoride

Scheme 41 Preparation of 3-nitrophenoxysulfonyl fluoride

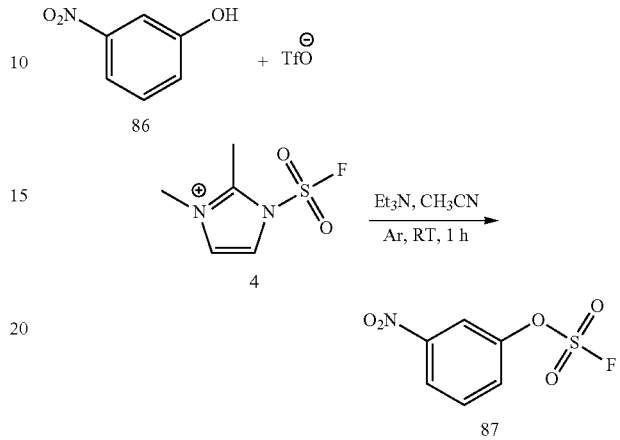

Triethylamine (220 μL, 1.59 mmol) was added to a solution of m-nitrophenol [Compound 86] (148 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (420 mg, 1.28 mmol) in acetonitrile (1 mL) was added in one portion. The reaction was allowed to run for 1 hour under argon atmosphere, during which time the reaction was monitored by TLC (petroleum ether:ethyl acetate=10:1, product: R$_f$=0.42). Column chromatography (silica gel 300-400 mesh, petroleum ether:ethyl acetate=10:1) afforded 3-nitrophenoxysulfonyl fluoride [compound 87] as a green liquid (196 mg, 85%) (Scheme 41).

Green liquid, 196 mg, 85% yield; $^1$H NMR (400 MHz, CDCl$_3$) δ 8.36-8.31 (m, 1H), 8.25 (s, 1H), 7.76-7.73 (m, 2H); $^{13}$C NMR (100 MHz, CDCl$_3$) 149.8, 149.2, 131.6, 127.3, 123.8, 117.1; $^{19}$F NMR (376 MHz, CDCl$_3$) δ +38.6 (s, 1F); GC-MS (t$_R$): 11.6 min. EI-MS (m/z): 221 [M]$^+$; HRMS (EI, m/z): calculated for C$_6$H$_4$NO$_5$FS: 220.9794 [M]$^+$, found: 220.9800.

Embodiment 42

Preparation of 1-naphthyloxysulfonyl fluoride

Scheme 42 Preparation of 1-naphthyloxysulfonyl fluoride

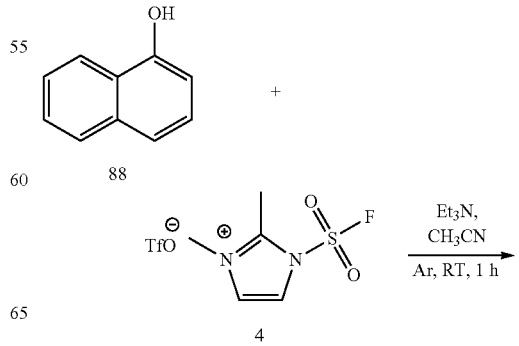

-continued

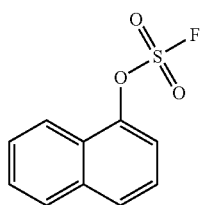

89

Triethylamine (220 µL, 1.59 mmol) was added to a solution of 1-naphthol [compound 88] (150 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [compound 4] (421 mg, 1.28 mmol) in acetonitrile (1 mL) was added in one portion. The reaction was allowed to run for 1 hour under argon atmosphere, during which time the reaction was monitored by TLC (petroleum ether:ethyl acetate=10:1, product: $R_f$=0.64). Column chromatography (silica gel 300-400 mesh, petroleum ether:ethyl acetate=10:1) afforded 1-naphthoxysulfonyl fluoride [compound 89] (178 mg, 76%) as a light green liquid (Scheme 2).

Light green liquid, 178 mg, 76% yield; $^1$H NMR (400 MHz, CDCl$_3$) δ 8.10 (d, J=8.0 Hz, 1H), 7.92 (dd, J=12.4, 7.6 Hz, 2H), 7.69-7.60 (m, 2H), 7.56-7.49 (m, 2H); $^{13}$C NMR (100 MHz, CDCl$_3$) δ 146.3, 135.1, 128.9, 128.2, 128.0, 127.6, 125.9, 125.2, 120.7, 117.7; $^{19}$F NMR (376 MHz, CDCl$_3$) δ +38.5 (s, 1F); GC-MS ($t_R$): 13.7 min, EI-MS (m/z): 226 [M]$^+$.

Embodiment 43

Preparation of 1-naphtho[2,3-d][1,3,2]dioxa-2,2-dioxothiophene

Scheme 43 Preparation of 1-naphtho[2,3-d][1,3,2]dioxa-2,2-dioxothiophene

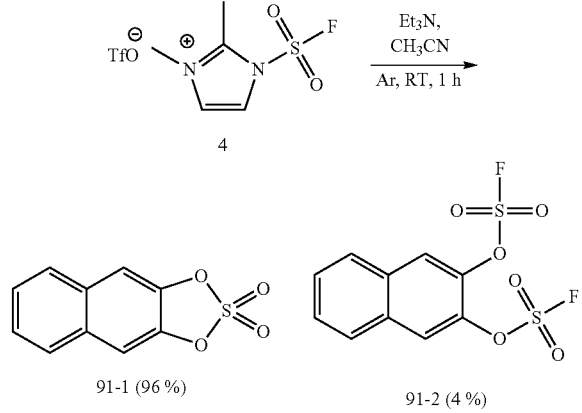

Triethylamine (440 µL, 3.17 mmol) was added to a solution of 2,3-dihydroxynaphthalene [Compound 90] (169 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [Compound 4] (421 g, 1.28 mmol) in acetonitrile (1 mL) was added in one portion. The reaction was allowed to run for 1 hour under argon atmosphere, during which time the reaction was monitored by TLC (petroleum ether:ethyl acetate=10:1, product: $R_f$=0.56). Column chromatography (silica gel 300-400 mesh, petroleum ether:ethyl acetate=10:1) afforded 1-naphtho[2,3-d][1,3,2] dioxa-2,2-dioxothiophene [compound 91-1] as a white solid (132 mg, 57%) (Scheme 43).

White solid, m.p. 112.8-121.1° C., 132 mg, 57% yield; $^1$H NMR (400 MHz, CDCl$_3$) δ 7.83 (dd, J=5.4, 2.4 Hz, 2H), 7.57-7.54 (m, 4H); $^{13}$C NMR (100 MHz, CDCl$_3$) δ 141.5, 130.4, 128.1, 127.1, 108.7; $^{19}$F NMR (376 MHz, CDCl$_3$) δ +40.0 (a, 2F); GC-MS ($t_R$): 16.9 min, EI-MS (m/z): 222 [M]$^+$; HRMS (EI, m/z): calculated for C$_{10}$H$_6$O$_4$S: 221.9987 [M]$^+$, found 221.9993.

Embodiment 44

Preparation of benzo[d][1,3,2]dioxa-2,2-dioxothiophene

Scheme 44 Preparation of benzo[d][1,3,2]dioxa-2,2-dioxothiophene

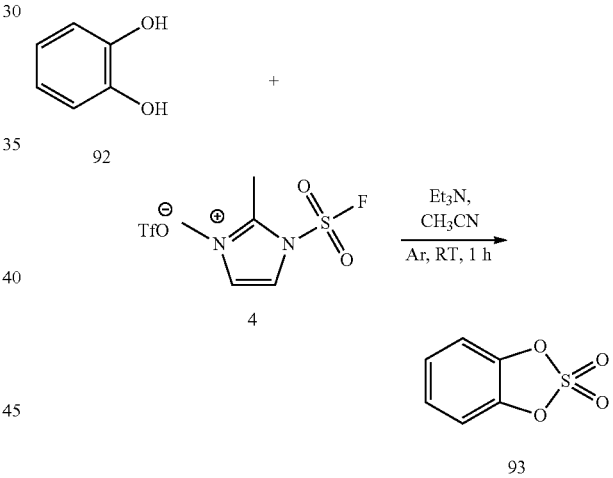

Triethylamine (220 µL, 1.59 mmol) was added to a solution of catechol [compound 92] (117 mg, 1.05 mmol) in acetonitrile (1 mL) at room temperature. After the mixture was stirred for 10 minutes, a solution of 1-(fluorosulfonyl)-2-3-dimethyl-1H-imidazolium trifluoromethaesulfonate [compound 4] (448 mg, 1.27 mmol) in acetonitrile (1 mL) was added in one portion. The reaction was allowed to run for 1 hour under argon atmosphere, during which time the reaction was monitored by TLC (petroleum ether:ethyl acetate=10:1, product: $R_f$=0.47). Column chromatography (silica gel 300-400 mesh, petroleum ether:ethyl acetate=10:1) afforded benzo[d][1,3,2]dioxa-2,2-dioxothiophene [compound 93] as a white solid (74 mg, 40%) (Scheme 44).

White solid, m.p. 33.4-35.4° C., 74 mg, 40% yield; $^1$H NMR (400 MHz, CDCl$_3$) δ 7.22 (s, 4H); $^{13}$C NMR (100 MHz, CDCl$_3$) δ 142.7, 125.5, 111.9; $^{19}$F NMR (376 MHz, CDCl$_3$) no signal; GC-MS ($t_R$): 9.0 min; EI-MS (m/z): 172 [M]$^+$.

Embodiment 45

Preparation of 2,6-diisopropylphenoxysulfonyl fluoride

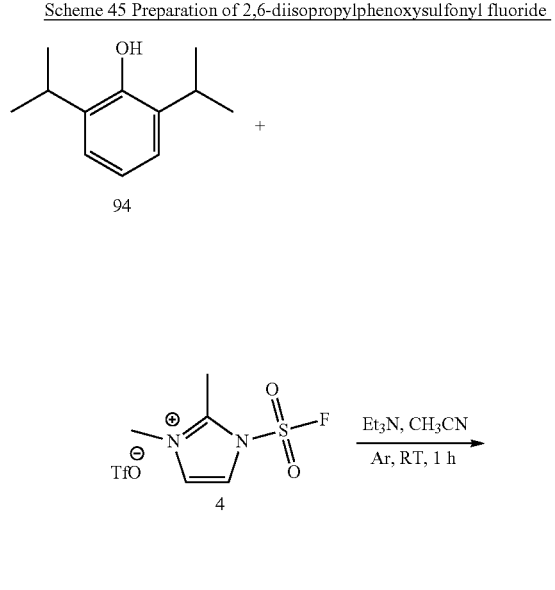

Triethylamine (220 µL, 1.59 mmol) was added to a solution of propofol [compound 94] (190 mg, 1.04 mmol) in acetonitrile (1 mL) at room temperature. After the mixture was stirred for 10 minutes, a solution of 1-(fluorosulfonyl)-2-3-dimethyl-1H-imidazolium trifluoromethanesulfonate [compound 4] (420 mg, 1.28 mmol) in acetonitrile (1 mL) was added in one portion. The reaction was allowed to run for 1 hour under argon atmosphere, during which time the reaction was monitored by TLC (petroleum ether:ethyl acetate=10:1, product: $R_f$=0.74). Column chromatography (silica gel 300-400 mesh, petroleum ether:ethyl acetate=20:1) afforded 2,6-diisopropylphenoxysulfonyl fluoride [compound 95] as a colorless liquid (193 mg, 71%) (Scheme 45).

Colorless liquid, 193 mg, 71% yield; $^1$H NMR (400 MHz, CDCl$_3$) δ 7.35-7.31 (m, 1H), 7.23 (d, J=7.6 Hz, 2H), 3.30 (sept, J=6.8 Hz, 2H), 1.26 (d, J=6.8 Hz, 12H); $^{13}$C NMR (100 MHz, CDCl$_3$) δ146.4, 141.4, 129.0, 125.4, 27.4 (d, J=1.5 Hz), 23.6; $^{19}$F NMR (376 MHz, CDCl$_3$) δ +41.3 (s, 1F); GC-MS ($t_R$): 11.8 min, EI-MS (m/z): 260 [M]$^+$; HRMS (EI, m/z): calculated for C$_{12}$H$_{17}$O$_3$FS: 260.0882 [M]$^+$, found: 260.0886.

Embodiment 46

Preparation of 1,3-dioxoisoindole-2-sulfonyl fluoride

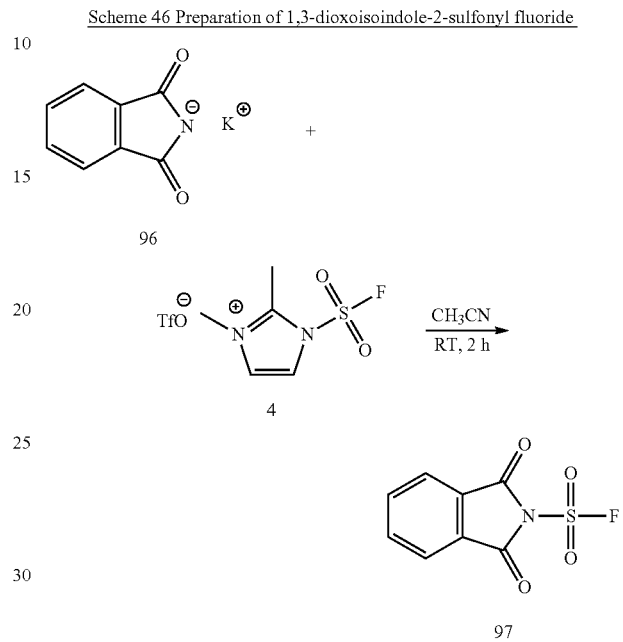

Potassium phthalimide salt [compound 96] (93 mg, 0.5 mmol) was dissolved in acetonitrile (2 mL) at room temperature, followed by addition of 1-(fluorosulfonyl)-2,3-dimethyl-1H-imidazolium trifluoromethanesulfonate [compound 4] (164 mg, 0.5 mmol). The reaction was allowed to run for 2 hours, during which time GC-MS detected the formation of the product 1,3-dioxoisoindole-2-sulfonyl fluoride [compound 97], but the signal disappeared upon detection after extraction (Scheme 46).

GC-MS ($t_R$): 9.8 min; EI-MS (m/z): 229 [M]$^+$.

Embodiment 47

Preparation of 3-oxobenzo[d]isothiazole-2(3H)-sulfonyl fluoride-1,1-dioxide

Scheme 47 Preparation of 3-oxobenzo[d]isothiazole-2(3H)-sulfonyl fluoride-1,1-dioxide

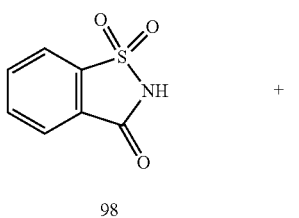

98

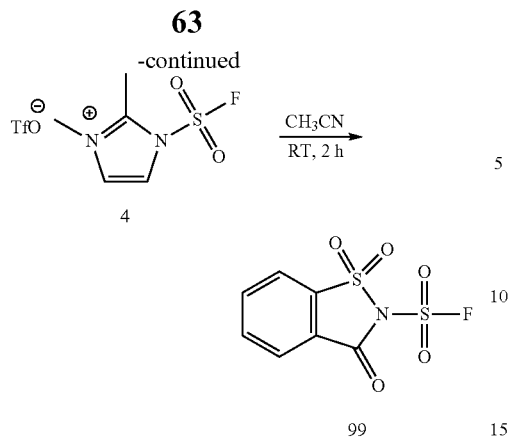

Saccharin [Compound 98] (93 mg, 0.5 mmol) was dissolved in acetonitrile (2 mL) at room temperature, and 1-(fluorosulfonyl)-2,3-dimethyl-1H-imidazolium trifluoromethanesulfonate [Compound 4] (164 mg, 0.5 mmol) was added thereto. The reaction was allowed to run for 2 hours, during which time GC-MS detected the formation of part of the product 3-oxobenzo[d]isothiazole-2(3H)-sulfonyl fluorine-1,1-dioxide [Compound 99], but the signal disappeared upon detection after extraction (Scheme 47).

GC-MS ($t_R$): 14.3 min: EI-MS (m/z): 265 [M]$^+$.

Embodiment 48

Preparation of 4-benzylpiperazine-1-sulfonyl fluoride

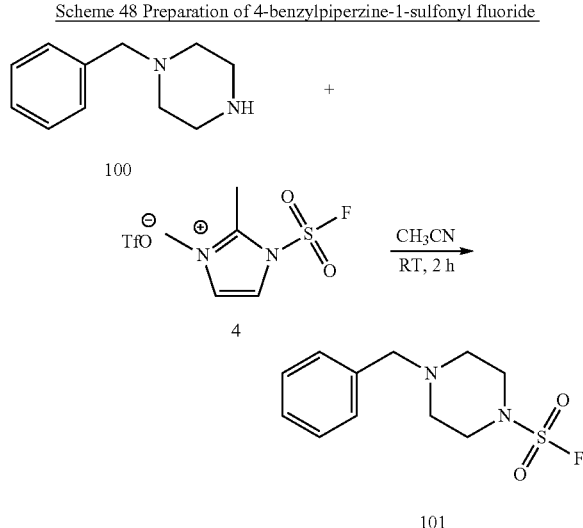

1-Benzylpiperazine [compound 100] (176 mg, 1 mmol) was dissolved in acetonitrile (3 mL) at room temperature, followed by addition of 1-(fluorosulfonyl)-2,3-dimethyl-1H-imidazolium trifluoromethanesulfonate [compound 4] (328 mg, 1 mmol). The reaction was allowed to run for 2 hours. After completion of the reaction as indicated by GC-MS, water (30 mL) was added into the reaction mixture, which was then extracted with ethyl acetate (20 mL×3). The combined organic phase was washed with water (20 mL) and saturated brine (20 mL), dried over anhydrous sodium sulfate, and filtered through a filter paper. The filtrate was concentrated by a rotary evaporator and then suctioned by an oil pump to remove the residual solvent to give 4-benzylpiperazine-1-sulfonyl fluoride [Compound 101] as a yellow oil (219 mg, 85%) (Scheme 48).

Yellow oil, 219 mg, 85% yield; $^1$H NMR (400 MHz CDCl$_3$) δ 7.32 (m, 5H), 3.56 (s, 2H), 3.47 (s, 4H), 2.57 (s, 4H); $^{13}$C NMR (100 MHz, CDCl$_3$) δ 137.3, 129.1, 128.6, 127.6, 62.6, 51.6, 47.2; $^{19}$F NMR (376 MHz, CDCl$_3$) δ 38.2 (s, 1F); GC-MS ($t_R$): 10.4 min; EI-MS (m/z): 258 [M]$^+$; HRMS (EI, m/z): calculated for C$_{11}$H$_{15}$N$_2$O$_2$FS: 258.0838 [M]$^+$, found: 258.0842.

Embodiment 49

Preparation of 2-(m-tolyl)pyrrolidine-1-sulfonyl fluoride

Scheme 49 Preparation of 2-(3-tolyl)-pyrrolidine-1-sulfonyl fluoride

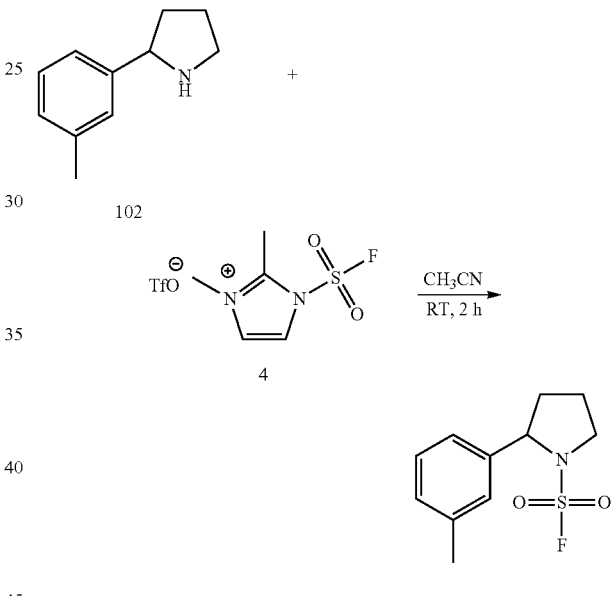

2-(3-Tolyl)-pyrrolidine [compound 102] (161 mg, 1 mmol) was dissolved in acetonitrile (3 mL) at room temperature, followed by addition of 1-(fluorosulfonyl)-2,3-dimethyl-1H-imidazolium trifluoromethanesulfonate [compound 4] (328 mg, 1 mmol). The reaction was allowed to run for 2 hours. After completion of the reaction as indicated by GC-MS, water (30 mL) was added to the reaction mixture, which was then extracted with ethyl acetate (20 mL×3). The combined organic phase was washed with water (20 mL) and saturated brine (20 mL), dried over anhydrous sodium sulfate, and filtered through a filter paper. The filtrate was concentrated by a rotary evaporator and then suctioned by an oil pump to remove the residual solvent to give 2-(3-tolyl)-pyrrolidine-1-sulfonyl fluoride [Compound 103] as a yellow oil (198 mg, 81%) (Scheme 49).

Yellow oil, 198 mg, 81% yield; $^1$H NMR (400 MHz, CDCl$_3$) δ 7.28-7.08 (m, 4H), 4.98 (m, 1H), 3.75 (m, 2H), 2.44 (m, 1H), 2.37 (s, 3H), 2.05 (m, 3H); $^{13}$C NMR (100 MHz, CDCl$_3$) δ 140.9, 138.3, 128.5, 126.5, 122.9, 65.0, 50.9, 36.0, 24.2, 21.5; $^{19}$F NMR (376 MHz, CDCl$_3$) δ 39.1

(s, 1F); GC-MS ($t_R$): 9.8 min; EI-MS (m/z): 243 [M]$^+$; HRMS (EI, m/z): calculated for $C_{11}H_{14}NO_2FS$: 243.0729 [M]$^+$, found: 243.0735.

Embodiment 50

Preparation of N-methylaniline sulfonyl fluoride

Scheme 50 Preparation of N-methylaniline sulfonyl fluoride

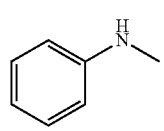

104

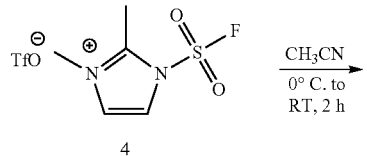

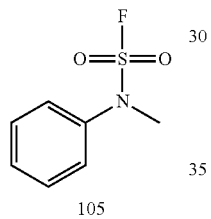

105

Embodiment 51

Preparation of 2-(p-tolyl)pyrolidine-1-sulfonyl fluoride

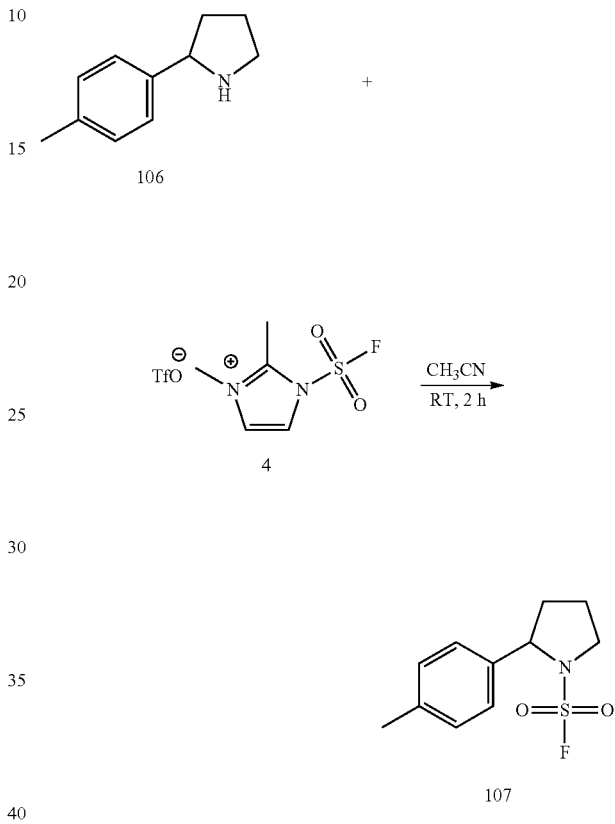

N-Methylaniline [compound 104] (1.07 g, 10 mmol) was dissolved in acetonitrile (10 mL). The mixture was cooled in an ice bath and then 1-(fluorosulfonyl)-2,3-dimethyl-1H-imidazolium trifluoromethanesulfonate [compound 4] (3.28 g, 10 mmol) was added thereto. After completion of the addition, the ice bath was removed, and the reaction was allowed to run for 2 hours at room temperature. After completion of the reaction as indicated by GC-MS, water (50 mL) was added to the reaction mixture, which was then extracted with ethyl acetate (30 mL×3). The combined organic phase was washed with water (30 mL) and saturated brine (30 mL), dried over anhydrous sodium sulfate, and filtered through a filter paper. The filtrate was concentrated by a rotary evaporator and then suctioned by an oil pump to remove the residual solvent to give N-methylaniline sulfonyl fluoride [Compound 105] as a yellow oil (1.56 g, 83%) (Scheme 50).

Yellow oil, 1.56 g, 83% yield; $^1$H NMR (400 MHz, CDCl$_3$) δ 7.43 (m, 5H), 3.44 (d, J=2.4 Hz, 3H); $^{13}$C NMR (100 MHz, CDCl$_3$) δ 139.9 (d, J=2.8 Hz), 139.9, 129.1, 126.7 (d, J=2.1 Hz), 40.7 (d, J=1.5 Hz); $^{19}$F NMR (376 MHz, CDCl$_3$) δ 41.8 (s, 1F); GC-MS ($t_R$): 6.9 min; EI-MS (m/z): 189 [M]$^+$; HRMS (EI, m/z): calculated for $C_7H_8NO_2FS$: 189.0260 [M]$^+$, found: 189.0257.

2-(4-Tolyl)-pyrrolidine [compound 106] (161 mg, 1 mmol) was dissolved in acetonitrile (3 mL) at room temperature, followed by addition of 1-(fluorosulfonyl)-2,3-dimethyl-1H-imidazolium trifluoromethanesulfonate [compound 4] (328 mg, 1 mmol). The reaction was allowed to run for 2 hours. After completion of the reaction as indicated by GC-MS, water (30 mL) was added to the reaction mixture, which was then extracted with ethyl acetate (20 mL×3). The combined organic phase was washed with water (20 mL) and saturated brine (20 mL), dried over anhydrous sodium sulfate, and filtered through a filter paper. The filtrate was concentrated by a rotary evaporator and then suctioned by an oil pump to remove the residual solvent to give 2-(4-tolyl)-pyrrolidine-1-sulfonyl fluoride [Compound 107] as a pale yellow solid (181 mg, 74%) (Scheme 51).

Pale yellow solid, m.p. 53-57° C., 181 mg, 74% yield; $^1$H NMR (400 MHz, CDCl$_3$) δ 7.17 (m, 4H), 4.97 (m, 1H), 3.74 (m, 2H), 2.44 (m, 1H), 2.34 (s, 3H), 2.03 (m, 3H); $^{13}$C NMR (100 MHz, CDCl$_3$) δ 138.0, 137.5, 129.3, 125.8, 64.9, 50.8, 36.0, 24.2, 21.1; $^{19}$F NMR (376 MHz, CDCl$_3$) δ 39.3 (s, 1F); GC-MS ($t_R$): 9.9 min: EI-MS (m/z): 243 [M]$^+$; HRMS (EI, m/z): calculated for $C_{11}H_4NO_2FS$: 243.0729 [M]$^+$. found: 243.0731.

Embodiment 52

Preparation of N-isopropylbenzylamine sulfonyl fluoride

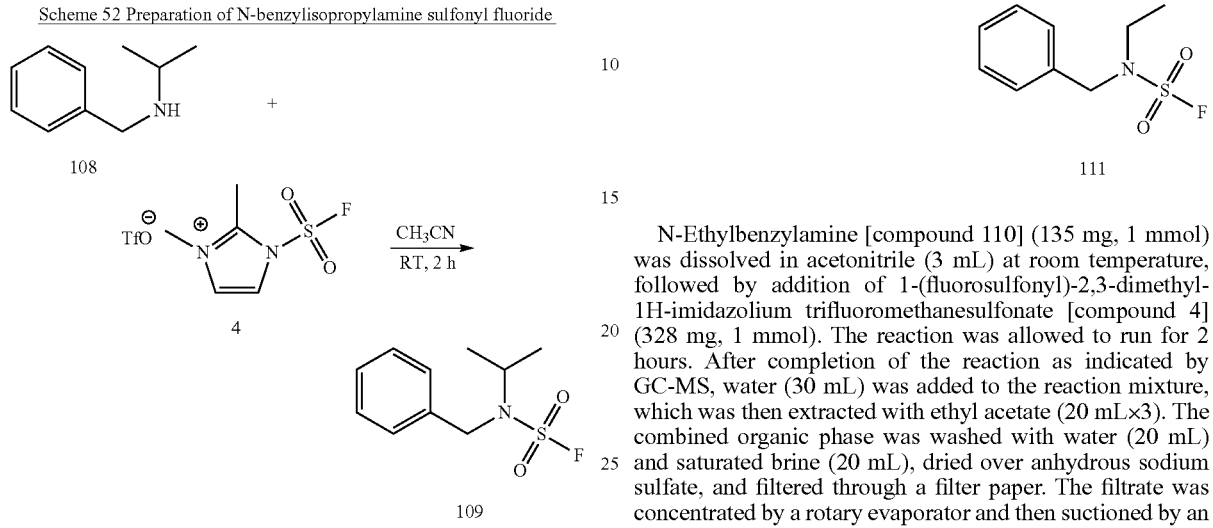

N-Benzylisopropylamine [compound 108] (149 mg, 1 mmol) was dissolved in acetonitrile (3 mL) at room temperature, followed by addition of 1-(fluorosulfonyl)-2,3-dimethyl-1H-imidazolium trifluoromethanesulfonate [compound 4] (328 mg, 1 mmol). The reaction was allowed to run for 2 hours. After completion of the reaction as indicated by GC-MS, water (30 mL) was added to the reaction mixture, which was then extracted with ethyl acetate (20 mL×3). The combined organic phase was washed with water (20 mL) and saturated brine (20 mL), dried over anhydrous sodium sulfate, and filtered through a filter paper. The filtrate was concentrated by a rotary evaporator and then suctioned by an oil pump to remove the residual solvent to give N-benzylisopropylamine sulfonyl fluoride [Compound 109] as a yellow oil (176 mg, 76%) (Scheme 52).

Yellow oil, 176 mg, 76% yield; $^1$H NMR (400 MHz, CDCl$_3$) δ 7.34 (m, 5H), 4.49 (s, 2H), 4.07 (sept. J=6.8 Hz, 1H), 1.23 (d, J=6.8 Hz, 6H); $^{13}$C NMR (100 MHz, CDCl$_3$) δ 136.3 (d, J=2.2 Hz), 128.8, 128.1, 127.6, 53.5 (d, J=2.4 Hz), 49.7 (d, J=1.9 Hz), 20.5 (d, J=2.1 Hz); $^{19}$F NMR (376 MHz, CDCl$_3$) δ 50.6 (s, 1F); GC-MS (t$_R$): 8.4 min; EI-MS (m/z): 231 [M]$^+$; HRMS (EI, m/z): calculated for C$_{10}$H$_{14}$NO$_2$FS: 231.0729 [M]$^+$, found: 231.0740.

Embodiment 53

Preparation of N-ethylbenzylamine sulfonyl fluoride

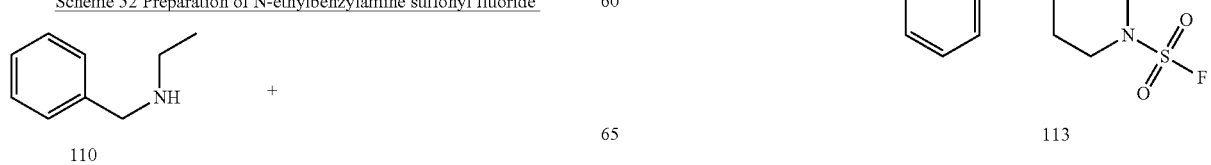

N-Ethylbenzylamine [compound 110] (135 mg, 1 mmol) was dissolved in acetonitrile (3 mL) at room temperature, followed by addition of 1-(fluorosulfonyl)-2,3-dimethyl-1H-imidazolium trifluoromethanesulfonate [compound 4] (328 mg, 1 mmol). The reaction was allowed to run for 2 hours. After completion of the reaction as indicated by GC-MS, water (30 mL) was added to the reaction mixture, which was then extracted with ethyl acetate (20 mL×3). The combined organic phase was washed with water (20 mL) and saturated brine (20 mL), dried over anhydrous sodium sulfate, and filtered through a filter paper. The filtrate was concentrated by a rotary evaporator and then suctioned by an oil pump to remove the residual solvent to give N-ethylbenzylamine sulfonyl fluoride [Compound 111] as a yellow oil (177 mg, 82%) (Scheme 53).

Yellow oil, 177 mg, 82% yield; $^1$H NMR (400 MHz, CDCl$_3$, TMS) δ 7.37 (m, 5H), 4.51 (s, 2H), 3.34 (dq, J=2.4 Hz, J=7.2 Hz, 2H), 1.19 (t, J=7.2 Hz, 3H); $^{13}$C NMR (100 MHz, CDCl$_3$) δ 134.3 (d, J=2.1 Hz), 129.0, 128.6, 128.4, 51.7 (d, J=1.8 Hz), 43.5 (d, J=2.3 Hz), 12.2; $^{19}$F NMR (376 MHz, CDCl$_3$) δ 49.8 (s, 1F); GC-MS (tat): 7.9 min; EI-MS (m/z): 217 [M]$^+$; HRMS (EI, m/z): calculated for C$_9$H$_{12}$NO$_2$FS: 217.0537 [M]$^+$, found: 217.0576.

Embodiment 54

Preparation of 4-benzylpiperidine-1-sulfonyl fluoride

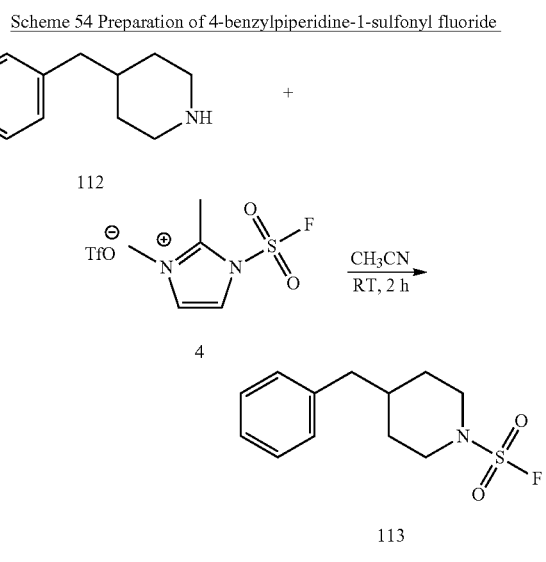

4-Benzylpiperidine [Compound 112] (175 mg, 1 mmol) was dissolved in acetonitrile (3 mL) at room temperature, followed by addition of 1-(fluorosulfonyl)-2,3-dimethyl-1H-imidazolium trifluoromethanesulfonate [Compound 4] (328 mg, 1 mmol). The reaction was allowed to run for 2 hours. After completion of the reaction as indicated by GC-MS, water (30 mL) was added to the reaction mixture, which was then extracted with ethyl acetate (20 mL×3). The combined organic phase was washed with water (20 mL) and saturated brine (20 mL), dried over anhydrous sodium sulfate, and filtered through a filter paper. The filtrate was concentrated by a rotary evaporator and then suctioned by an oil pump to remove the residual solvent to give 4-benzylpiperidine-1-sulfonyl fluoride [compound 113] as a pale yellow solid (190 mg, 74%) (Scheme 39).

Pale yellow solid, m.p. 54-58° C. 190 mg, 74% yield; $^1$H NMR (400 MHz, CDCl$_3$) δ 7.32-7.13 (m, 5H), 3.91 (d, J=12.8 Hz, 2H), 2.93 (t, J=12.8 Hz, 2H), 2.58 (d, J=6.8 Hz, 2H), 1.76 (d, J=14 Hz, 2H), 1.68 (m, 1H), 1.38 (dq, J=4 Hz, J=11.6 Hz, 2H); $^{13}$C NMR (100 MHz, CDCl$_3$) δ 139.4, 129.1, 128.4, 126.3, 47.5, 42.5, 37.0, 30.7; $^{19}$F NMR (376 MHz, CDCl$_3$) δ 39.6 (s, 1F); GC-MS (t$_R$): 10.8 min; EI-MS (m/z): 257 [M]$^+$; HRMS (EI, m/z): calculated for C$_{12}$H$_{16}$NO$_2$FS: 257.0886 [M]$^+$, found: 257.0887.

Embodiment 55

Preparation of 4-phenylpiperidine-1-sulfonyl fluoride

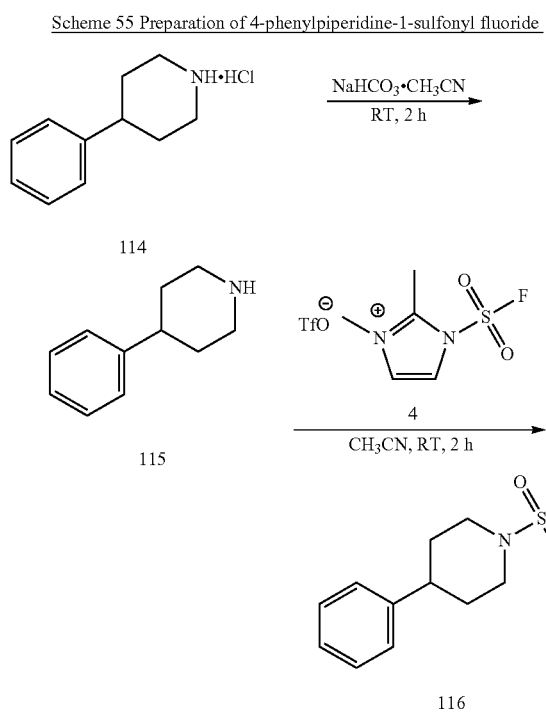

4-Phenylpiperidine hydrochloride [compound 114] (197 mg, 1 mmol) was dissolved in acetonitrile (10 mL) at room temperature, followed by addition of sodium bicarbonate (168 mg, 2 mmol). The reaction was allowed to run for 2 hours. The mixture was filtered to remove the solid, and then 1-(fluorosulfonyl)-2,3-dimethyl-1H-imidazolium trifluoromethanesulfonate [compound 4] (328 mg, 1 mmol) was added and the reaction was allowed to run for 2 hours. After completion of the reaction as indicated by GC-MS, water (30 mL) was added to the reaction mixture, which was then extracted with ethyl acetate (20 mL×3). The combined organic phase was washed with water (20 mL) and saturated brine (20 mL), dried over anhydrous sodium sulfate, and filtered through a filter paper. The filtrate was concentrated by a rotary evaporator and then suctioned by an oil pump to remove the residual solvent to give 4-phenylpiperidine-1-sulfonyl fluoride [compound 116] as a white solid (168 mg, 70%) (Scheme 55).

White solid, m.p. 83-84° C., 168 mg, 69% yield; $^1$H NMR (400 MHz, CDCl$_3$) δ 7.36-7.20 (m, 5H), 4.06 (d, J=12.8 Hz, 2H), 3.12 (t, J=12.4 Hz, 2H), 2.68 (t, J=12.4 Hz, 1H), 1.97 (d, J=12.8 Hz, 2H), 1.87 (dq, J=4 Hz, J=12.8 Hz, 2H); $^{13}$C NMR (100 MHz, CDCl$_3$) δ 144.2, 128.8, 126.9, 126.7, 47.9, 41.4, 32.0; $^{19}$F NMR (376 MHz, CDCl$_3$) δ 39.8 (s, 1F); GC-MS (t$_R$): 10.1 min; EI-MS (m/z): 243 [M]$^+$; HRMS (EI, m/z): calculated for C$_{11}$H$_{14}$NO$_2$FS: 243.0729 [M]$^+$, found: 243.0733.

Embodiment 56

Preparation of 3-(benzyloxy)azetidine-1-sulfonyl fluoride

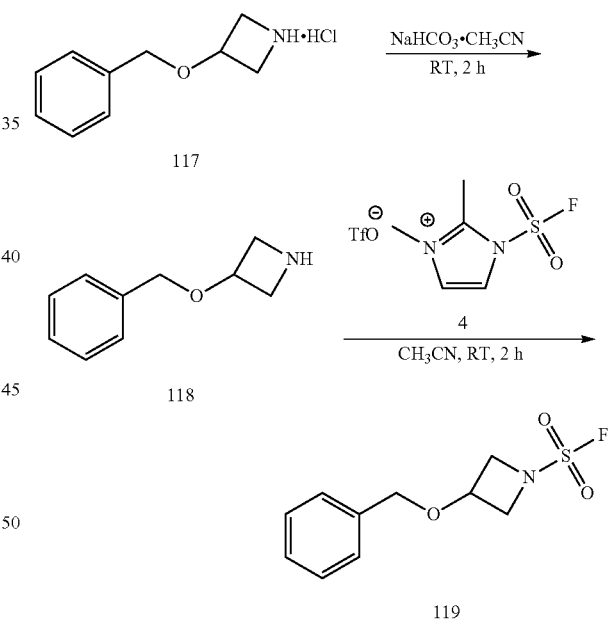

3-(Benzyloxy)azetidine hydrochloride [compound 117] (199 Mg, 1 mmol) was dissolved in acetonitrile (10 mL) at room temperature, followed by addition of sodium bicarbonate (168 mg, 2 mmol). The reaction was allowed to run for 2 hours, after which time the mixture was filtered to remove the solid. Then 1-(fluorosulfonyl)-2,3-dimethyl-1H-imidazolium trifluoromethanesulfonate [compound 4] (328 mg, 1 mmol) was added, and the reaction was allowed to run for 2 hours. After completion of the reaction as indicated by GC-MS, water (30 mL) was added to the reaction mixture, which was then extracted with ethyl acetate (20 mL×3). The combined organic phase was washed with water (20 mL)

and saturated brine (20 mL), dried over anhydrous sodium sulfate, and filtered through a filter paper. The filtrate was concentrated by a rotary evaporator and then suctioned by an oil pump to remove the residual solvent to give 3-(benzyloxy)azetidine-1-sulfonyl fluoride [compound 119] as a yellow oil (232 mg, 95%) (Scheme 56).

Yellow oil, 232 mg, 95% yield; $^1$H NMR (400 MHz, CDCl$_3$) δ7.35 (m, 5H), 4.49 (s, 2H), 4.41 (quin, J=6 Hz, 1H), 4.20 (t, J=7.6 Hz, 2H), 4.07 (m, 2H); $^{13}$C NMR (100 MHz, CDCl$_3$) δ 136.5, 128.7, 128.5, 128.1, 71.8, 66.2, 60.3; F NMR (376 MHz, CDCl$_3$) δ 29.0 (s, 1F); GC-MS (t$_R$): 10.0 min; EI-MS (m/z): 245 [M]$^+$; HRMS (EI, m/z): calculated for C$_{10}$H$_{12}$NO$_3$FS: 245.0522 [M]$^+$, found: 245.0530.

Embodiment 57

Preparation of 3-[3-(trifluoromethyl)phenoxy]-azetidine-1-sulfonyl fluoride

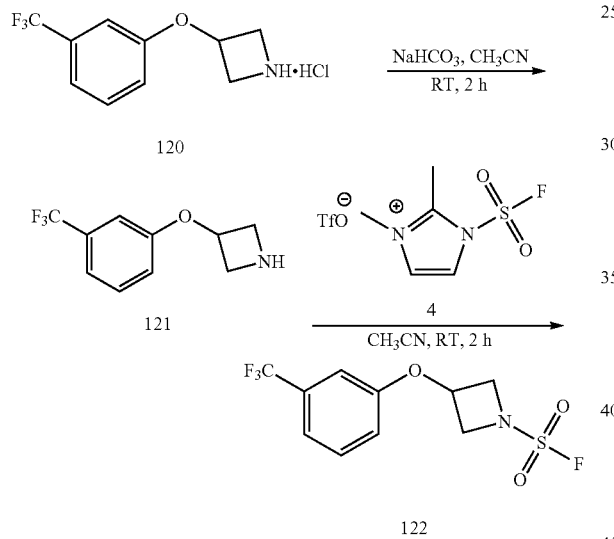

3-[3-(Trifluoromethyl)phenoxy]-azetidine hydrochloride [compound 120] (253 mg, 1 mmol) was dissolved in acetonitrile (10 mL) at room temperature, followed by addition of sodium bicarbonate (168 mg, 2 mmol). The reaction was allowed to run for 2 hours, after which time the mixture was filtered to remove the solid. Then 1-(fluorosulfonyl)-2,3-dimethyl-1H-imidazolium trifluoromethanesulfonate [Compound 4] (328 mg, 1 mmol) was added and the reaction was allowed to run for 2 hours. After completion of the reaction as indicated by GC-MS, water (30 mL) was added to the reaction mixture, which was then extracted with ethyl acetate (20 mL×3). The combined organic phase was washed with water (20 mL) and saturated brine (20 mL), dried over anhydrous sodium sulfate, and filtered through a filter paper. The filtrate was concentrated by a rotary evaporator and then suctioned by an oil pump to remove the residual solvent to give 3-[3-(trifluoromethyl)phenoxy]-azetidine-1-sulfonyl fluoride [compound 112] as a yellow oil (252 mg, 84%) (Scheme 58).

Yellow oil, 252 mg, 84% yield; $^1$H NMR (400 MHz, CDCl$_3$) δ 7.44 (t, J=8 Hz, 1H), 7.31 (d, J=7.6 Hz, 1H), 6.98 (s, 1H), 6.93 (d, J=8.4 Hz, 1H), 5.06 (quin, J=5.6 Hz, 1H), 4.55 (t, J=8 Hz, 2H), 4.29 (m, 2H); $^{13}$C NMR (100 MHz, CDCl$_3$) δ 156.0, 132.3 (q, J=32.4 Hz), 130.7, 123.8 (q, J=270.8 Hz), 119.1 (q, J=3.7 Hz), 117.9, 111.8 (q, J=3.9 Hz), 64.9, 59.6; $^{19}$F NMR (376 MHz, CDCl$_3$) δ 29.6 (s, 1F), −62.3 (s, 3F); GC-MS (t$_R$): 9.7 min; EI-MS (m/z): 299 [M]$^+$; HRMS (EI, m/z): calculated for C$_{10}$H$_9$NO$_3$F$_4$S: 299.0239 [M]$^+$, found-299.0244.

Embodiment 58

Preparation of 4-benzamidopiperidine-1-sulfonyl fluoride

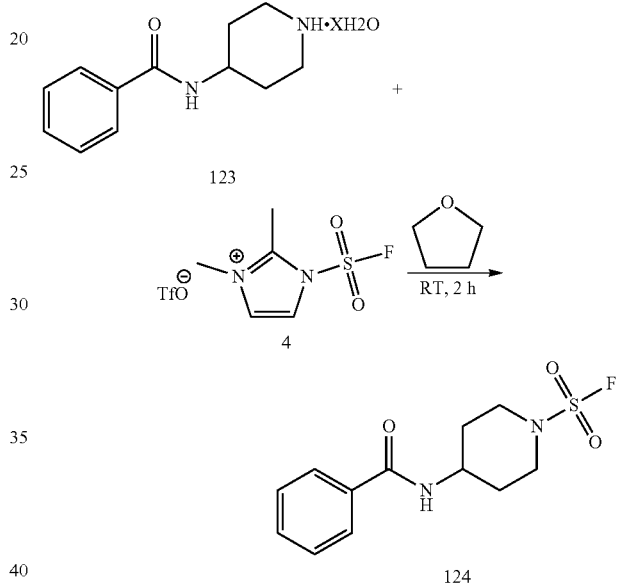

4-Benzamidopiperidine hydrate [compound 123] (204 mg, 1 mmol) was dissolved in tetrahydrofuran (5 mL) at room temperature, followed by addition of 1-(fluorosulfonyl)-2,3-dimethyl-1H-imidazolium trifluoromethanesulfonate [compound 4] (328 mg, 1 mmol). The reaction was allowed to run for 2 hours. After completion of the reaction as indicated by LC-MS, water (30 mL) was added to the reaction mixture, which was then extracted with ethyl acetate (20 mL×3). The combined organic phase was washed with water (20 mL) and saturated brine (20 mL), dried over anhydrous sodium sulfate, and filtered through a filter paper. The filtrate was concentrated by a rotary evaporator, and purified by column chromatography (silica gel 300-400 mesh, petroleum ether:ethyl acetate=2:1) to give 4-benzamidopiperidine-1-sulfonyl fluoride [compound 124] as a white solid (200 mg, 70%) (Scheme 58).

White solid, m.p. 205-207° C., 200 mg, 70% yield; $^1$H NMR (400 MHz, DMSO-d$_6$) δ 8.40 (d, J=7.6 Hz, 1H), 7.84 (d, J=7.2 Hz, 2H), 7.53 (t, J=7.2 Hz, 1H), 7.47 (t, J=7.6 Hz, 2H), 4.06 (m, 1H), 3.82 (d, J=13.2 Hz, 2H), 3.33 (dt, J=4.4 Hz, J=15.2 Hz, 2H), 1.95 (dd, J=2.4 Hz, J=13.2 Hz, 2H), 1.67 (dq, J=4 Hz, J=12 Hz, 2H); $^{13}$C NMR (100 MHz, DMSO-d$_6$) δ 165.9, 134.5, 131.2, 128.2, 127.4, 46.2, 45.1, 30.0; $^{19}$F NMR (MHz, DMSO-d$_6$) δ 43.8 (s, 1F); LC-MS ($t_R$): 1.4 min; ESI-MS (m/z): 287 [MH]+; HRMS (DART, m/z): calculated for $C_{12}H_{16}N_2O_3FS$: 287.0860 [MH]+, found: 287.0860.

Embodiment 59

Preparation of 3-(3,4,5-trimethoxybenzamido)piperidine-1-sulfonyl fluoride

Scheme 59 Preparation of 3-(3,4,5-trimethoxybenzamido)piperidine-1-sulfonyl fluoride

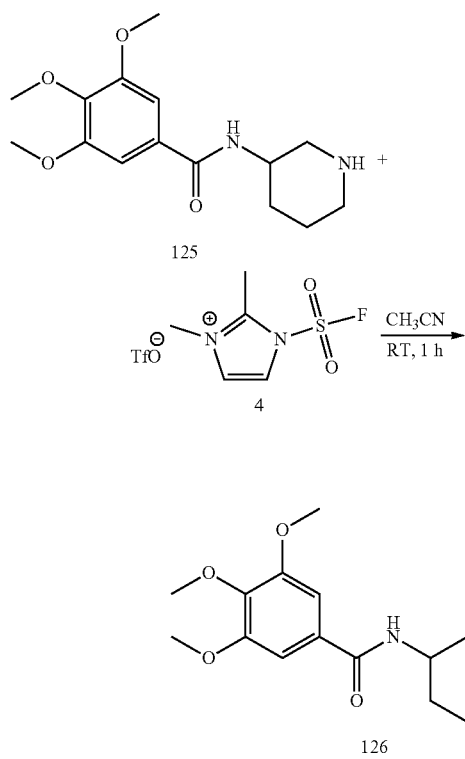

1-(Fluorosulfonyl)-2,3-dimethyl-1H-imidazolium trifluoromethanesulfonate [compound 4] (164 mg, 0.5 mmol) was dissolved in acetonitrile (5 mL) at room temperature, followed by addition of troxipide [compound 125] (148 mg, 0.5 mmol). The reaction was allowed to run for 1 hour. After completion of the reaction as indicated by LC-MS, column chromatography (silica gel 300-400 mesh, dichloromethane:ethyl acetate=10:1) afforded 3-(3,4,5-trimethoxybenzamido)piperidine-1-sulfonyl fluoride [compound 126] as a white solid (184 mg, 98%) (Scheme 59).

White solid, m.p. 184-186° C. 184 mg, 98% yield; $^1$H NMR (400 MHz, DMSO-$d_6$) δ 8.33 (d, J=6.8 Hz, 1H), 7.16 (s, 2H), 3.98 (m, 1H), 3.86 (m, 1H), 3.83 (s, 6H), 3.73 (m, 1H), 3.70 (s, 3H), 3.19 (t, J=11.6 Hz, 1H), 3.05 (m, 1H), 1.94 (t, J=10 Hz, 2H), 1.65 (sext, J=10 Hz, 2H); $^{13}$C NMR (100 MHz, DMSO-$d_6$) δ 165.8, 152.5, 140.2, 129.3, 105.1, 60.1, 56.0, 50.1, 47.0, 45.4, 28.2, 22.8; $^{19}$F NMR (MHz, DMSO-$d_6$) δ 43.8 (s, 1F); LC-MS ($t_R$): 1.4 min: ESI-MS (m/z): 377 [MH]+; HRMS (DART, m/z): calculated for $C_{15}H_{22}N_2O_6FS$: 377.1177 [MH]+, found: 377.1175.

Embodiment 60

Preparation of N-fluorosulfonylfluoxetine

Scheme 60 Preparation of N-fluorosulfonylfluoxetine

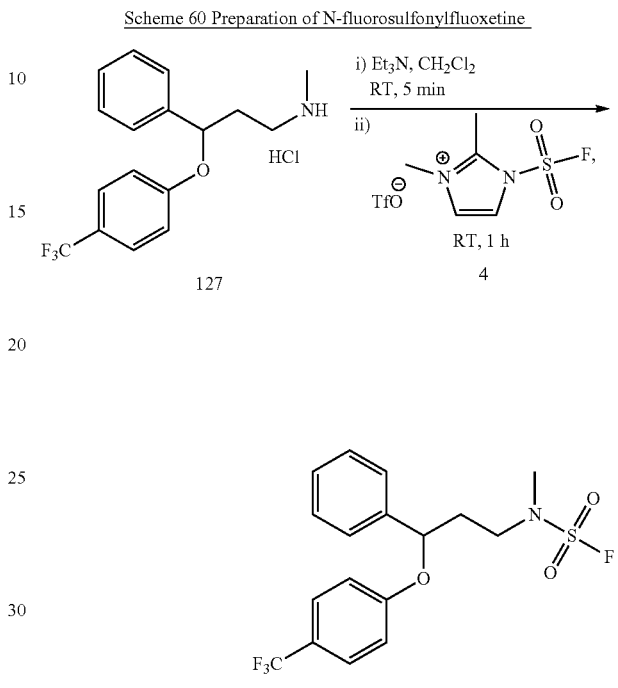

At room temperature, triethylamine (69 μL, 0.5 mmol) was added to a solution of fluoxetine hydrochloride (compound 127 (173 mg, 0.5 mmol) in dichloromethane (4 mL) and then stirred at room temperature for 5 minutes. Subsequently, 1-(fluorosulfonyl)-2,3-dimethyl-1H-imidazolium trifluoromethanesulfonate [compound 4] (164 mg, 0.5 mmol) was added and the reaction mixture was stirred at room temperature for 1 hour. After completion of the reaction as indicated by TLC (petroleum ether 60-90:ethyl acetate=9:1, product: $R_f$=0.4), column chromatography (silica gel 300-400 mesh, petroleum ether 60-90:ethyl acetate=6:1) afforded N-fluorosulfonylfluoxetine [compound 128] as a white solid (152 mg, 85%) (Scheme 60).

White solid, m.p 125-127° C., 152 mg, 85% yield; $^1$H NMR (400 MHz, CD$_3$CN) δ 7.50 (d, J=9 Hz, 2H), 7.43-7.28 (m, 5H), 7.00 (d, J=9 Hz, 2H), 5.41 (dd, J=9 Hz, J=4 Hz, 1H), 3.63 (m, 1H), 3.52 (m, 1H), 3.02 (d, J=2 Hz, 3H), 2.25 (m, 2H); $^{13}$C NMR (100 MHz, CD$_3$CN) δ161.4, 141.3, 129.8, 129.2, 127.7 (q, J=4 Hz), 127.1, 125.6 (q, J=269 Hz), 123.3 (q, J=32 Hz), 117.2, 77.8, 49.2, 36.8, 36.5; $^{19}$F NMR (376 MHz, CD$_3$CN) δ 41.7 (d, J=2 Hz, 1F), −60.8 (s, 3F). HRMS (DART, m/z): calculated for $C_{17}H_{21}F_4N_2O_3S$: 409.1204 [M+NH$_4$]+, found:409.1201.

Embodiment 61

Preparation of N-fluorosulfonylamoxapine

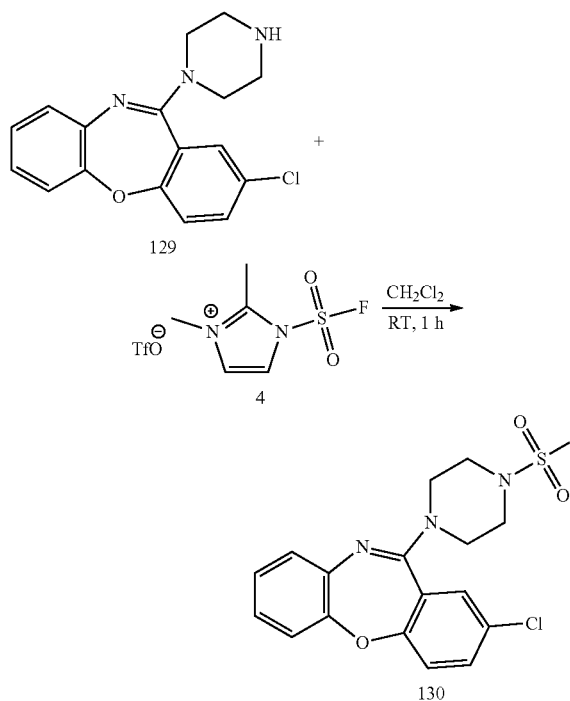

1-(Fluorosulfonyl)-2,3-dimethyl-1H-imidazolium trifluoromethanesulfonate [compound 4] (164 mg, 0.5 mmol) was added to a solution (5 mL) of amoxapine [compound 129] (157 mg, 0.5 mmol) in dichloromethane and the resulting mixture was stirred at room temperature for 1 hour. After completion of the reaction as indicated by TLC (petroleum ether 60-90:ethyl acetate=3:1, product: $R_f$=0.7), column chromatography (silica gel 300-400 mesh, petroleum ether 60-90:ethyl acetate=4:1) afforded N-fluorosulfonylamoxapine [compound 130] as a white solid (188 mg, 95%) (Scheme 61).

White solid, m.p. 147-150° C., 188 mg, 95% yield; $^1$H NMR (400 MHz, CD$_3$CN) δ 7.54-7.03 (m, 7H), 3.60 (m, 8H); $^{13}$C NMR (100 MHz, CD$_3$CN) δ 160.4, 159.6, 152.7, 140.8, 134.2, 131.3, 129.9, 127.9, 127.0, 126.2, 125.5, 123.9, 121.3, 47.5, 47.0; $^{19}$F NMR (376 MHz, CD$_3$CN) δ 39.4 (s). HRMS (DART, m/z): calculated for C$_{17}$H$_6$ClFN$_3$O$_3$S: 396.0579 [MH]$^+$, found: 396.0577.

Embodiment 62

Preparation of 1,4-bis(fluorosulfonyl)piperazine

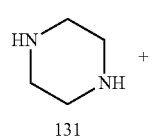

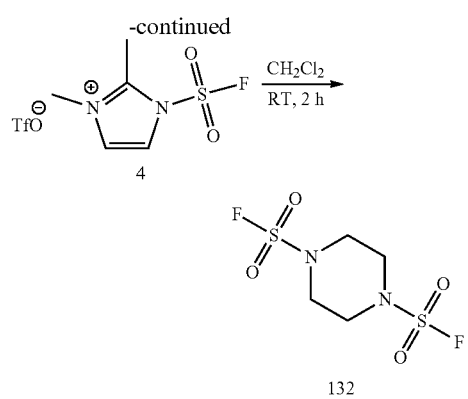

1-(Fluorosulfonyl)-2,3-dimethyl-1H-imidazolium trifluoromethanesulfonate [compound 4] (656 mg, 2.0 mmol) was added to a solution of piperazine [compound 131] (86 mg, 1.0 mmol) in dichloromethane (5 mL) and the resulting mixture was stirred at room temperature for 2 hours. After completion of the reaction as indicated by TLC, the reaction mixture was concentrated by a rotary evaporator, followed by addition of ethyl acetate (25 mL). The organic phase was washed with 2M hydrochloric acid (20 mL), 0.1M hydrochloric acid (20 mL×2), water (20 mL) and saturated brine (10 mL×2), dried over anhydrous sodium sulfate, and filtered through a filter paper. The filtrate was concentrated by a rotary evaporator and then suctioned by an oil pump to remove the residual solvent to give 1,4-bis(fluorosulfonyl)piperazine [compound 132] as a white solid (200 mg, 81%) (Scheme 62).

White solid, m.p. 246-248° C., 200 mg, 81% yield; $^1$H NMR (400 MHz, (CD$_3$)$_2$CO) δ 3.76 (s); $^{13}$C NMR (100 MHz, (CD$_3$)$_2$CO) δ 46.8; $^{19}$F NMR (376 MHz, (CD$_3$)$_2$CO) δ 41.2 (s). HRMS (DART, m/z): calculated for C$_4$H$_7$F$_2$N$_2$O$_4$S: 248.9821 [M−H]$^−$, found: 248.9820.

Embodiment 63

Preparation of (S)-2-benzyl-aziridine-1-sulfonyl fluoride

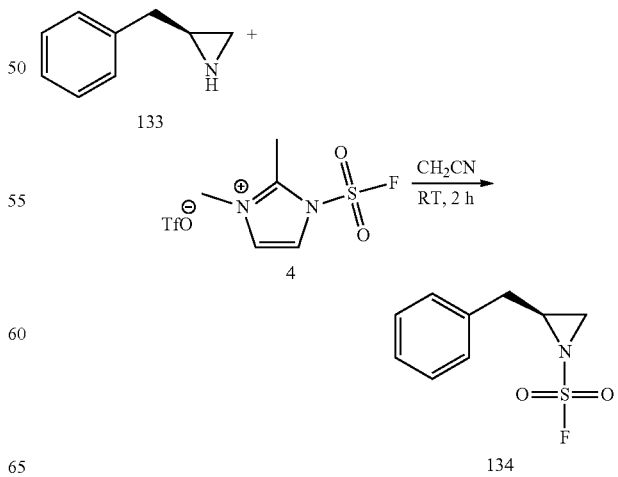

S-2-benzylazacyclopropane [compound 133] (266 mg, 2 mmol) was dissolved in acetonitrile (3 mL) at room temperature, followed by addition of 1-(fluorosulfonyl)-2,3-dimethyl-1H-imidazolium trifluoromethanesulfonate [compound 4] (656 mg, 2 mmol). The reaction was allowed to run for 2 hours. GC-MS monitored that the reaction proceeded well. Post-treatment was carried out by adding water (30 mL) to the reaction mixture and extracting the resulting mixture with ethyl acetate (20 mL×3). The combined organic phase was washed with water (20 mL) and saturated brine (20 mL), dried over anhydrous sodium sulfate, and filtered through a filter paper. The filtrate was concentrated by a rotary evaporator and then suctioned by an oil pump to remove the residual solvent. The expected product was not obtained.

GC-MS ($t_R$): 8.3 min; EI-MS (m/z): 215 [M]$^+$.

Embodiment 64

Preparation of Benzylamide Sulfonyl Fluoride

Scheme 64 Preparation of benzylamine sulfonyl fluoride

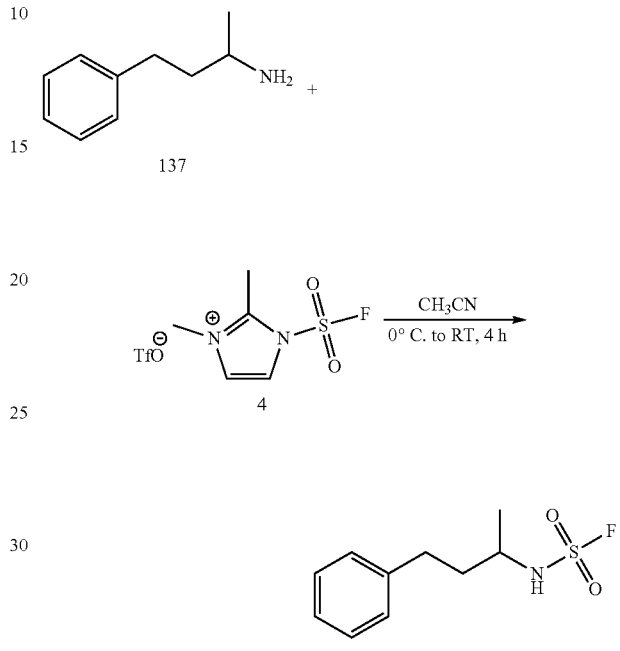

Benzylamine [Compound 135] (1.07 g, 10 mmol) was dissolved in acetonitrile (10 mL). The mixture was cooled in an ice bath, and then 1-(fluorosulfonyl)-2,3-dimethyl-1H-imidazolium trifluoromethanesulfonate [Compound 4] (3.28 g, 10 mmol) was added. After completion of the addition, the ice bath was removed, and the reaction was allowed to run for 4 hours at room temperature. After completion of the reaction as indicated by GC-MS, water (50 mL) was added to the reaction mixture, which was then extracted with ethyl acetate (30 mL×3). The combined organic phase was washed with water (30 mL) and saturated brine (30 mL), dried over anhydrous sodium sulfate, and filtered through a filter paper. The filtrate was concentrated by a rotary evaporator and then suctioned by an oil pump to remove the residual solvent to give benzylamine sulfonyl fluoride [Compound 136] as a yellow oil (1.6 g, 84%) (Scheme 64).

Yellow oil, 1.6 g, 84% yield; $^1$H NMR (400 MHz, CDCl$_3$) δ 7.42-7.33 (m, 5H), 5.15 (br, 1H), 4.45 (d, J=5.6 Hz, 2H); $^{13}$C NMR (100 MHz, CDCl$_3$) δ 134.8, 129.2, 128.8, 128.1, 48.5; $^{19}$F NMR (376 MHz, CDCl$_3$) δ50.4 (s, 1F); GC-MS ($t_R$): 8.1 min; EI-MS (m/z): 189 [M]$^+$; HRMS (EI, m/z): calculated for C$_7$H$_8$NO$_2$FS: 189.0260 [M]$^+$, found: 189.0259.

Embodiment 65

Preparation of 4-phenyl-2-butylamine sulfonyl fluoride

Scheme 65 Preparation of 4-phenyl-2-butylamine sulfonyl fluoride

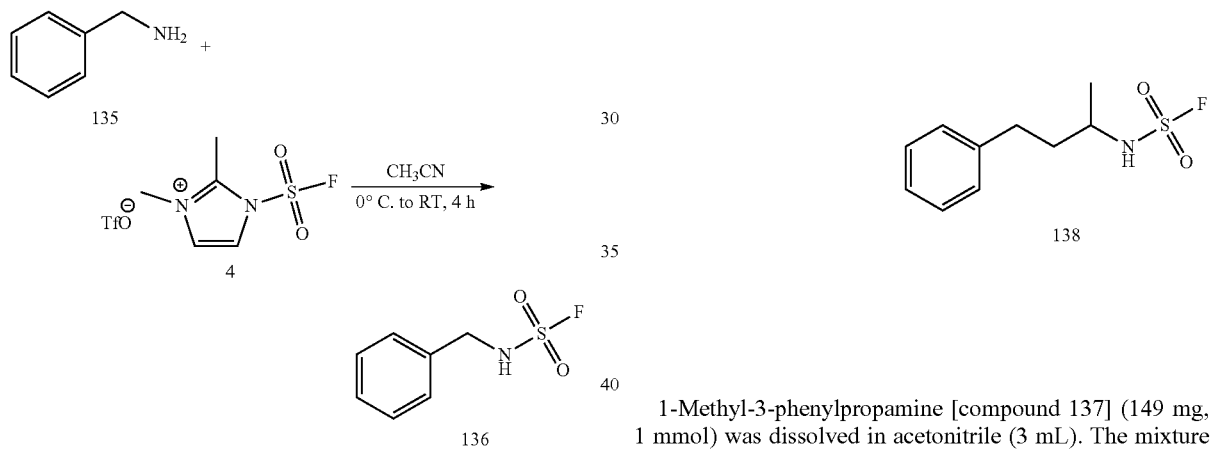

1-Methyl-3-phenylpropamine [compound 137] (149 mg, 1 mmol) was dissolved in acetonitrile (3 mL). The mixture was cooled in an ice bath, and then 1-(fluorosulfonyl)-2,3-dimethyl-1H-imidazolium trifluoromethanesulfonate [compound 4] (328 mg, 1 mmol) was added thereto. After completion of the addition, the ice bath was removed and the reaction was allowed to run for 4 hours at room temperature. After completion of the reaction as indicated by GC-MS, water (30 mL) was added to the reaction mixture, which was then extracted with ethyl acetate (20 mL×3). The combined organic phase was washed with water (20 mL) and saturated brine (20 mL), dried over anhydrous sodium sulfate, and filtered through a filter paper. The filtrate was concentrated by a rotary evaporator and then suctioned by an oil pump to remove the residual solvent to give 4-phenyl-2-butylamine sulfonyl fluoride [compound 138] as a yellow oil (207 mg, 90%) (Scheme 65).

Yellow oil, 207 mg, 90% yield; $^1$H NMR (400 MHz, CDCl$_3$) δ 7.30 (t, J=7.2 Hz, 2H), 7.22 (d, J=7.2 Hz, 1H), 7.18 (d, 2H, J=7.6 Hz), 4.91 (b 1H), 3.69 (m, 1H), 2.71 (m, 2H), 1.87 (m, 2H), 1.33 (d, J=6.8 Hz, 3H); $^{13}$C NMR (100 MHz, CDCl$_3$) δ 140.7, 128.7, 128.4, 126.3, 52.3, 38.5, 31.9, 21.3; $^{19}$F NMR (376 MHz, CDCl$_3$) δ 53.8 (d, J=5.6 Hz, 1F); LC-MS ($t_R$): 1.62 min ESI-MS (m/z): 230 [M−H]$^−$; HRMS (DART, m/z): calculated for C$_{10}$H$_{18}$N$_2$O$_2$FS: 249.1068 [M+NH$_4$]$^+$, found: 249.1067.

Embodiment 66

Preparation of 2-phenyl-1-ethylamine sulfonyl fluoride

Scheme 66 Preparation of 2-phenyl-1-ethylamine sulfonyl fluoride

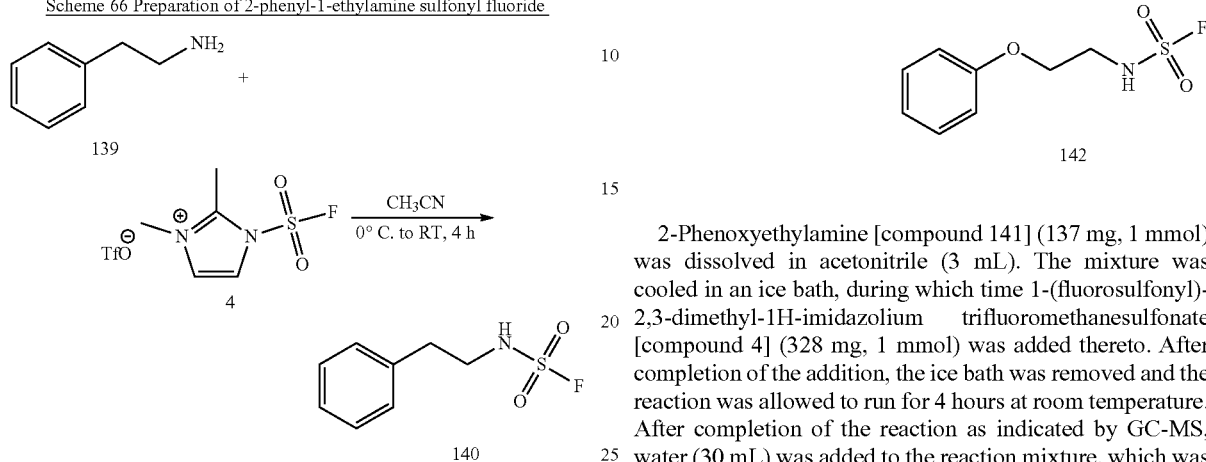

2-Phenylethylamine [compound 139] (121 mg, 1 mmol) was dissolved in acetonitrile (3 mL). The mixture was cooled in an ice bath, during which time 1-(fluorosulfonyl)-2,3-dimethyl-1H-imidazolium trifluoromethanesulfonate [compound 4] (328 mg, 1 mmol) was added thereto. After completion of the addition, the ice bath was removed and the reaction was allowed to run for 4 hours at room temperature. After completion of the reaction as indicated by GC-MS, water (30 mL) was added to the reaction mixture, which was then extracted with ethyl acetate (20 mL×3). The combined organic phase was washed with water (20 mL) and saturated brine (20 mL), dried over anhydrous sodium sulfate, and filtered through a filter paper. The filtrate was concentrated by a rotary evaporator and then suctioned by an oil pump to remove the residual solvent to give 2-phenyl-1-ethylamine sulfonyl fluoride [compound 140] as a yellow oil (196 mg, 97%) (Scheme 66).

Yellow oil, 196 mg, 97% yield; $^1$H NMR (400 MHz, CDCl$_3$) δ 7.38-7.20 (m, 5H), 4.88 (br, 1H), 3.57 (q, J=6.8 Hz, 2H), 2.94 (t, J=6.8 Hz, 2H); $^{13}$C NMR (100 MHz, CDCl$_3$) δ 136.9, 129.0, 128.9, 127.3, 45.6, 35.5; $^{19}$F N NMR (376 MHz, CDCl$_3$) δ 51.1 (s, 1F); LC-MS (t$_R$): 1.51 min; ESI-MS (m/z): 202 [M−H]$^-$; HRMS (DART, m/z): calculated for C$_8$H$_{14}$N$_2$O$_2$FS: 221.0755 [M+NH$_4$]$^+$, found: 221.0754.

Embodiment 67

Preparation of 2-phenoxy-1-ethylamine sulfonyl fluoride

Scheme 67 Preparation of 2-phenoxy-1-ethylaminosulfonyl fluoride

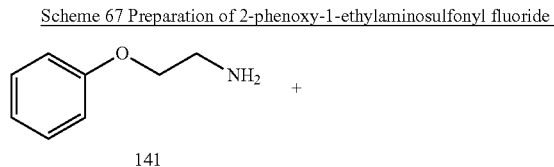

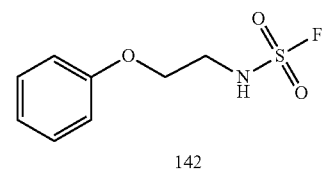

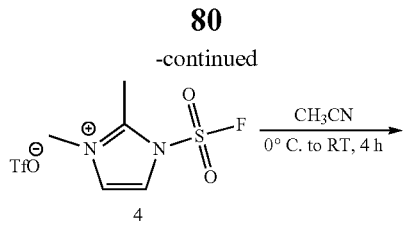

2-Phenoxyethylamine [compound 141] (137 mg, 1 mmol) was dissolved in acetonitrile (3 mL). The mixture was cooled in an ice bath, during which time 1-(fluorosulfonyl)-2,3-dimethyl-1H-imidazolium trifluoromethanesulfonate [compound 4] (328 mg, 1 mmol) was added thereto. After completion of the addition, the ice bath was removed and the reaction was allowed to run for 4 hours at room temperature. After completion of the reaction as indicated by GC-MS, water (30 mL) was added to the reaction mixture, which was then extracted with ethyl acetate (20 mL×3). The combined organic phase was washed with water (20 mL) and saturated brine (20 mL), dried over anhydrous sodium sulfate, and filtered through a filter paper. The filtrate was concentrated by a rotary evaporator and then suctioned by an oil pump to remove the residual solvent to give 2-phenoxy-1-ethylamine sulfonyl fluoride [Compound 142] as a pale yellow solid (203 mg, 92%) (Scheme 67).

Pale yellow solid, m.p. 46-49° C. 203 mg, 92% yield; $^1$H NMR (400 MHz, CDCl$_3$) δ 7.32 (t, J=8 Hz, 2H), 7.02 (t, J=7.6 Hz, 1H), 6.89 (d, J=7.6 Hz, 2H), 5.51 (br, 1H), 4.13 (t, J=4.8 Hz, 2H), 3.69 (m, 2H); $^{13}$C NMR (100 MHz, CDCl$_3$) δ 157.9, 129.8, 121.9, 114.6, 65.6, 44.0; $^{19}$F NMR (376 MHz CDCl$_3$) δ 51.1 (s, 1F); LC-MS (t$_R$): 1.48 min; ESI-MS (m/z): 218 [M−H]$^-$; HRMS (DART, m/z): calculated for C$_8$H$_{14}$N$_2$O$_3$FS: 237.0704 [M+NH$_4$]$^+$, found: 237.0703.

Embodiment 68

Preparation of (1,1'-biphenyl)-4-methylamine sulfonyl fluoride

Scheme 68 Preparation of (1,1'-biphenyl)-4-methylamine sulfonyl fluoride

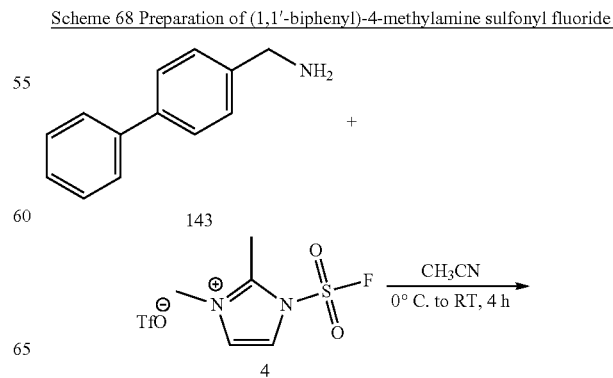

-continued

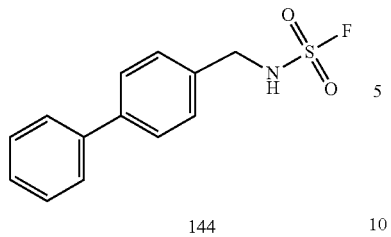

144

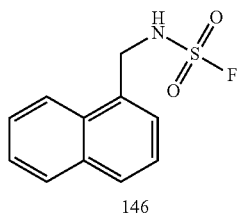

146

4-Phenylbenzylamine [compound 143] (183 mg, 1 mmol) was dissolved in acetonitrile (3 mL). The mixture was cooled in an ice bath, during which time 1-(fluorosulfonyl)-2,3-dimethyl-1H-imidazolium trifluoromethanesulfonate [compound 4] (328 mg, 1 mmol) was added thereto. After completion of the addition, the ice bath was removed and the reaction was allowed to run for 4 hours at room temperature. After completion of the reaction as indicated by LC-MS, water (30 mL) was added to the reaction mixture, which was then extracted with ethyl acetate (20 mL×3). The combined organic phase was washed with water (20 mL) and saturated NaCl solution (20 mL), dried over anhydrous sodium sulfate, and filtered through a filter paper. The filtrate was concentrated by a rotary evaporator and then suctioned by an oil pump to remove the residual solvent to give (1,1'-biphenyl)-4-methylamine sulfonyl fluoride [compound 144] as a pale yellow solid (246 mg, 93%) (Scheme 68).

Pale yellow solid, m.p. 107-111° C., 246 mg, 93% yield; $^1$H NMR (400 MHz, CDCl$_3$) δ 7.60 (m, 4H), 7.41 (m, 5H), 5.20 (br, 1H), 4.49 (d, J=5.6 Hz, 2H); $^{13}$C NMR (100 MHz, CD$_3$CN) δ 141.7, 141.2, 136.2, 129.9, 129.6, 128.6, 128.2, 127.9, 48.2; $^{19}$F NMR (376 MHz, CDCl$_3$) δ 50.6 (s, 1F); LC-MS (t$_R$): 1.64 min; ESI-MS (m/z): 264 [M−H]$^−$, HRMS (DART, m/z): calculated for C$_{13}$H$_{16}$N$_2$O$_2$FS: 283.0911 [M+NH$_4$]$^+$, found: 283.0911.

1-Naphthalenemethylamine [compound 145] (157 mg, 1 mmol) was dissolved in acetonitrile (3 mL). The mixture was cooled in an ice bath, during which time 1-(fluorosulfonyl)-2,3-dimethyl-1H-imidazolium trifluoromethanesulfonate [compound 4] (328 mg, 1 mmol) was added thereto. After completion of the addition, the ice bath was removed and the reaction was allowed to run for 4 hours at room temperature. After completion of the reaction as indicated by LC-MS, water (30 mL) was added to the reaction mixture, which was then extracted with ethyl acetate (20 mL×3). The combined organic phase was washed with water (20 mL) and saturated brine (20 mL), dried over anhydrous sodium sulfate, and filtered through a filter paper. The filtrate was concentrated by a rotary evaporator and then suctioned by an oil pump to remove the residual solvent to give naphthyl-1-methylamine sulfonyl fluoride [Compound 146] as a pale yellow solid (223 mg, 93%) (Scheme 69).

Pale yellow solid, m.p. 68-71° C., 223 mg, 93% yield; $^1$H NMR (400 MHz, CDCl$_3$) δ 8.00 (d, J=8.4 Hz, 1H), 7.90 (t, J=8.4 Hz, 2H), 7.64-7.44 (m, 4H), 5.14 (br, 1H), 4.89 (d, J=5.2 Hz, 2H); $^{13}$C NMR (100 MHz, CDCl$_3$) δ 133.9, 130.9, 129.9, 129.9, 129.1, 127.5, 127.3, 126.4, 125.4, 122.7, 46.5; $^{19}$F NMR (376 MHz, CDCl$_3$) δ 49.5 (s, 1F); LC-MS (t$_R$): 1.57 min; ESI-MS (m/z): 238 [M−H]$^−$, HRMS (DART, m/z): calculated for C$_{11}$H$_{14}$N$_2$O$_2$FS: 257.0755 [M+NH$_4$]$^+$, found: 257.0754.

Embodiment 69

Preparation of naphthyl-1-methylamine sulfonyl fluoride

Embodiment 70

Preparation of (S)-(−)-1-naphthyl)ethylamine sulfonyl fluoride

Scheme 69 Preparation of naphthyl-1-methylamine sulfonyl fluoride

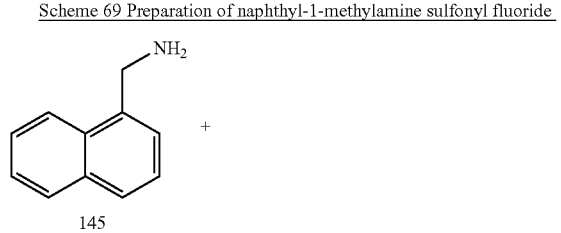

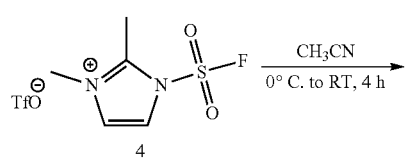

Scheme 70 Preparation of (S)-(−)-1-(1-naphthyl)ethylamine sulfonyl fluoride

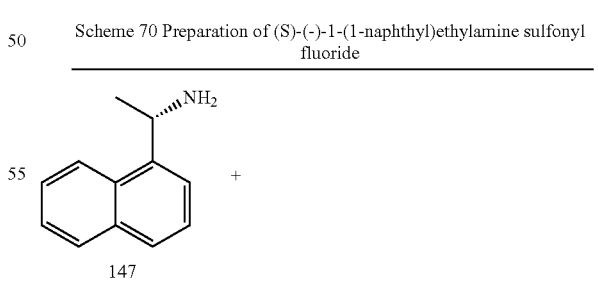

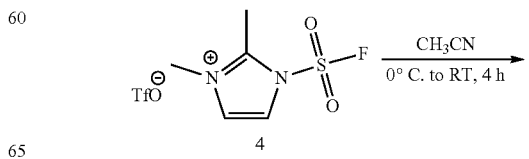

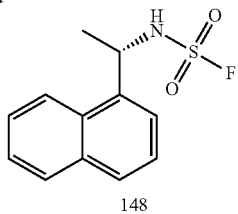

148

(S)-(−)-1-(1-Naphthyl)ethylamine [compound 147] (171 mg, 1 mmol) was dissolved in acetonitrile (3 mL). The mixture was cooled in an ice bath, during which time 1-(fluorosulfonyl)-2,3-dimethyl-1H-imidazolium trifluoromethanesulfonate [compound 4] (328 mg, 1 mmol) was added thereto. After completion of the addition, the ice bath was removed and the reaction was carried out for 4 hours at room temperature. After completion of the reaction as indicated by LC-MS, water (30 mL) was added to the reaction mixture, which was then extracted with ethyl acetate (20 mL×3). The combined organic phase was washed with water (20 mL) and saturated brine (20 mL), dried over anhydrous sodium sulfate, and filtered through a filter paper. The filtrate was concentrated by a rotary evaporator and then suctioned by an oil pump to remove the residual solvent to give (S)-(−)-1-(1-naphthyl)ethylamine sulfonyl fluoride [compound 148] as a pale yellow solid (252 mg, 99%) (Scheme 70).

Pale yellow solid, 252 mg, m.p. 69-71° C., 99% yield; $^1$H NMR (400 MHz, CDCl$_3$) δ 8.10 (d, J=8.4 Hz, 1H), 7.91 (d, J=8 Hz, 1H), 7.86 (d, J=8 Hz, 1H), 7.63-7.46 (m, 4H), 5.60 (quin, J=6.8 Hz, 1H), 5.28 (br, 1H), 1.82 (d, J=6.8 Hz, 3H); $^{13}$C NMR (100 MHz, CDCl$_3$) δ 135.7, 135.7, 134.0, 130.3, 129.3, 129.2, 127.1, 126.2, 125.4, 123.2, 122.5, 51.5, 21.9; $^{19}$F NMR (376 MHz, CDCl$_3$) δ 54.2 (s, 1F); LC-MS (t$_R$): 1.59 min; ESI-MS (m/z): 252 [M−H]$^−$, HRMS (DART, m/z): calculated for C$_{12}$H$_{16}$N$_2$O$_2$FS: 271.0911 [M+NH$_4$]$^+$, found: 271.0910.

Embodiment 71

Preparation of (N-fluorosulfonyl)-2-hydroxybenzylamine

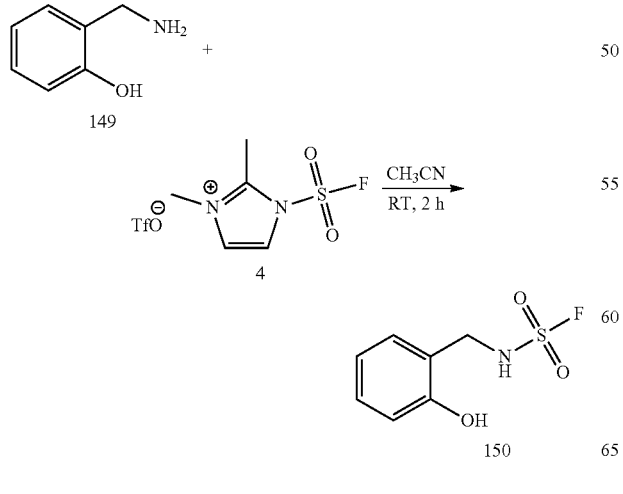

1-(Fluorosulfonyl)-2,3-dimethyl-1H-imidazolium trifluoromethanesulfonate [compound 4] (328 mg, 1.0 mmol) was added to a solution (6 mL) of 2-hydroxybenzylamine [compound 149] (123 mg, 1.0 mmol) in acetonitrile. The reaction mixture was stirred at room temperature for 2 hour. After completion of the reaction as indicated by TLC (petroleum ether 60-90:ethyl acetate=9:1, product: R$_f$=0.5), column chromatography (silica gel 300-400 mesh, petroleum ether 60-90:ethyl acetate=9:1) afforded (N-fluorosulfonyl)-2-hydroxybenzylamine [compound 150] as a white solid (97 mg, 47%) (Scheme 71).

White solid, m.p. 64-67° C., 97 mg, 47% yield; $^1$H NMR (400 MHz, CD$_3$CN) δ 7.26-6.86 (m, 6H), 4.37 (s, 2H); $^{13}$C NMR (100 MHz, (CD$_3$)$_2$CO) δ 156.1, 130.6, 130.3, 123.3, 120.5, 116.0, 44.0; $^{19}$F NMR (376 MHz, (CD$_3$)$_2$CO) δ 50.6 (s). HRMS (DART, m/z): calculated for C$_7$H$_7$FNO$_3$S: 204.0136 [M−H]$^−$, found: 204.0133.

Embodiment 72

Preparation of N-fluorosulfonyltyramine

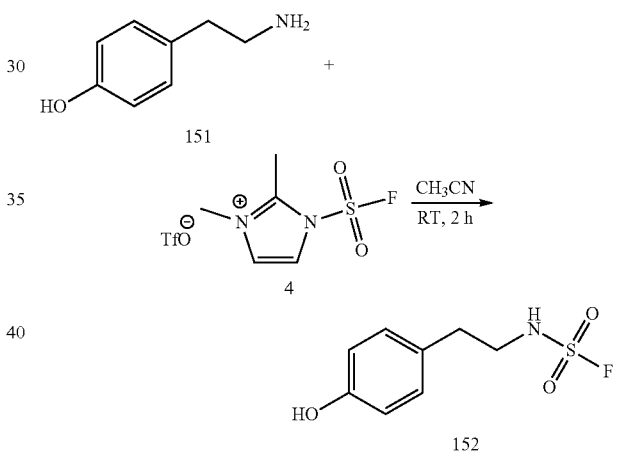

1-(Fluorosulfonyl)-2,3-dimethyl-1H-imidazolium trifluoromethanesulfonate [Compound 4] (328 mg, 1.0 mmol) was added to a solution (6 mL) of tyramine [Compound 151] (137 mg, 1.0 mmol) in acetonitrile. The resulting mixture was stirred at room temperature for 2 hours. After completion of the reaction as indicated by TLC (dichloromethane:ethyl acetate=6:1, product: R$_f$=0.5), column chromatography (silica gel 300-400 mesh, dichloromethane:ethyl acetate=6:1) afforded N-fluorosulfonyltyramine [compound 152] as a white solid (138 mg, 63%) (Scheme 72).

White solid, m.p. 90-92° C., 138 mg, 63% yield; $^1$H NMR (400 MHz, CD$_3$CN) δ 7.08 (d, J=8 Hz, 2H), 6.82 (br, 1H), 6.76 (d, J=8 Hz, 2H), 6.62 (br 1H), 3.41 (m, 2H), 2.78 (t, J=7 Hz, 2H); $^{13}$C NMR (100 MHz, (CD$_3$)$_2$CO) δ 157.1, 130.7, 129.5, 116.3, 46.7, 35.5; $^{19}$F NMR (376 MHz, (CD$_3$)$_2$CO) δ 50.8 (s). HRMS (DART, m/z): calculated for C$_8$H$_9$FNO$_3$S: 218.0293 [M−H]$^−$, found: 218.0290.

Embodiment 73

Preparation of tert-butyl (R)-2-(fluorosulfonyl)amino-2-phenylacetate

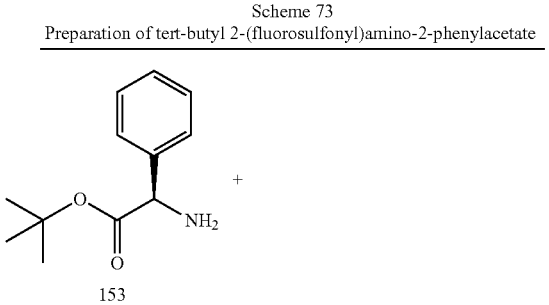

Embodiment 74

Preparation of 2-(4-fluorophenyl)-1,1-dimethylethylamine sulfonyl fluoride

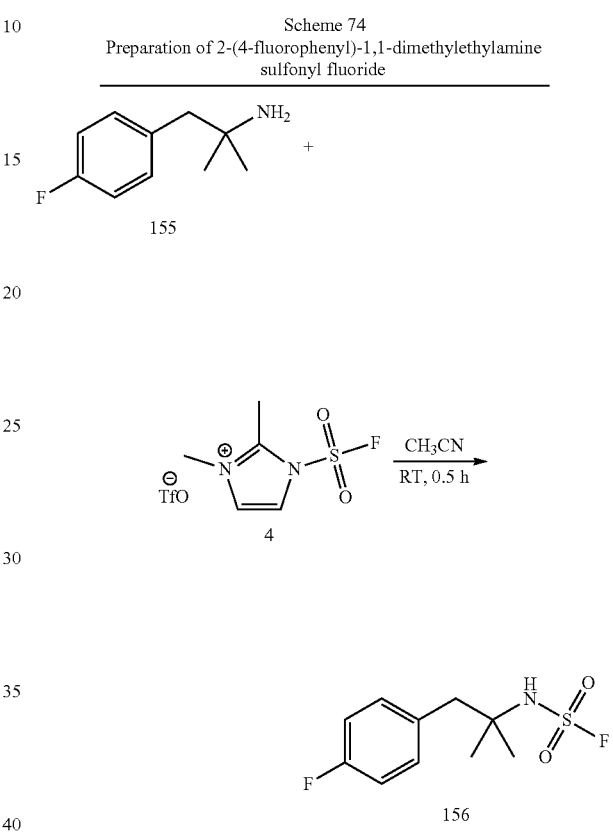

In an ice bath, a solution (3 mL) of tert-butyl (R)-2-amino-2-phenylacetate [compound 153] (1.45 g, 7.0 mmol) in acetonitrile was added dropwise to a solution (2 mL) of 1-(fluorosulfonyl)-2,3-dimethyl-1H-imidazolium trifluoromethanesulfonate [compound 4] (2.62 g, 8.0 mmol) in acetonitrile. After the addition was completed, the ice bath was removed and the reaction mixture was stirred at room temperature for 10 minutes. After completion of the reaction as indicated by TLC (petroleum ether:ethyl acetate=5:1, product: $R_f$=0.7), water (30 mL) was added to the reaction mixture, which was then extracted with ethyl acetate (25 mL×2). The combined organic phase was washed with water (20 mL) and saturated brine (10 mL×2), dried over anhydrous sodium sulfate, and filtered through a filter paper. The filtrate was concentrated by a rotary evaporator and then suctioned by an oil pump to remove the residual solvent to give tert-butyl (R)-2-(fluorosulfonyl)amino-2-phenylacetate [Compound 154] as a white solid (1.97 g, 97%) (Scheme 73).

White solid, m.p. 81-84° C., 1.97 g, 97% yield; $^1$H NMR (400 MHz, CDCl$_3$) δ 7.41-7.33 (m, 5H), 6.27 (br, 1H), 5.11 (s, 1H), 1.41 (s, 9H); $^{13}$C NMR (100 MHz, CDCl$_3$) δ 168.4, 134.8, 129.1, 129.1, 127.0, 84.7, 60.8, 27.7; $^{19}$F NMR (376 MHz, CDCl$_3$) δ 52.9 (s); LC-MS ($t_R$): 1.62 min; ESI-MS (m/z): 232 [M−$^t$Bu]$^-$.

1-(Fluorosulfonyl)-2,3-dimethyl-1H-imidazolium trifluoromethanesulfonate [compound 4] (164 mg, 0.5 mmol) was dissolved in acetonitrile (2 mL), followed by addition of 2-(4-fluorophenyl)-1,1-dimethylethylamine [compound 155] (84 mg, 0.5 mmol). The reaction mixture was stirred at room temperature for 0.5 hour. After completion of the reaction as indicated by TLC (petroleum ether:ethyl acetate=4:1, $R_f$=0.8), water (15 mL) was added to the reaction mixture, which was then extracted with ethyl acetate (15 mL×2). The combined organic phase was washed with water (10 mL) and saturated brine (5 mL×2), dried over anhydrous sodium sulfate, and filtered through a filter paper. The filtrate was concentrated by a rotary evaporator and then suctioned by an oil pump to remove the residual solvent to give 2-(4-fluorophenyl)-1,1-dimethylethylamine sulfonyl fluoride [compound 156] as a yellow oil (113 mg, 91%) (Scheme 74).

Yellow oil, 113 mg, 91% yield; $^1$H NMR (400 MHz, CDCl$_3$) δ 7.15 (m, 2H), 7.02 (m, 2H), 4.68 (br, 1H), 2.90 (s, 2H), 1.38 (s, 6H); $^{13}$C NMR (100 MHz, CDCl$_3$) δ 162.1 (d, J=244 Hz), 132.1 (d, J=7 Hz), 131.6 (d, J=3 Hz), 115.3 (d, J=22 Hz), 58.9 (s), 46.3 (d, J=2 Hz), 26.9 (s); $^{19}$F NMR (376 MHz, CDCl$_3$) δ 59.4 (s, 1F), −115.9 (s, 1F); GC-MS ($t_R$): 14.7 min; EI-MS (m/z): 249 [M]$^+$.

Embodiment 75

Preparation of (1R,2R)-1-benzyloxy-2-fluorosulfonylaminocyclopentane

Scheme 75
Preparation of (1R,2R)-1-benzyloxy-2-fluorosulfonylaminocyclopentane

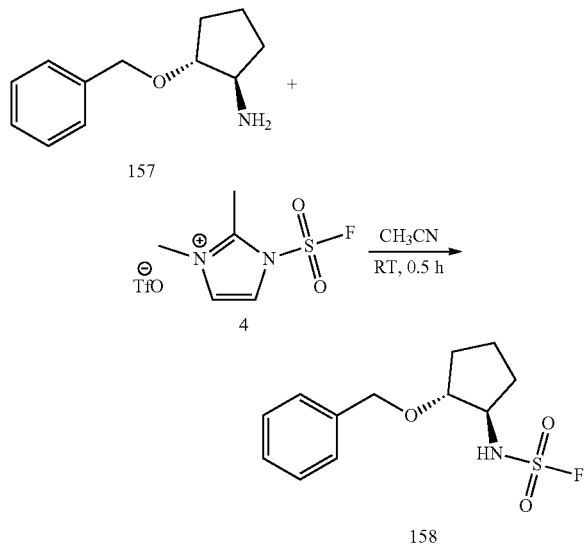

1-(Fluorosulfonyl)-2,3-dimethyl-1H-imidazolium trifluoromethanesulfonate [compound 4] (328 mg, 1.0 mmol) was dissolved in acetonitrile (3 mL), followed by addition of (1R,2R)-1-benzyloxy-2-aminocyclopentane [compound 157] (191 mg, 1.0 mmol). The reaction mixture was stirred at room temperature for 0.5 hour. After completion of the reaction as indicated by TLC (petroleum ether:ethyl acetate=10:1, product: $R_f$=0.6), water (20 mL) was added to the reaction mixture, which was then extracted with ethyl acetate (20 mL×2). Column chromatography (silica gel 300-400 mesh, petroleum ether:ethyl acetate=15:1) afforded (1R,2R)-1-benzyloxy-2-fluorosulfonylaminocyclopentane [Compound 158] as a white solid (168 mg, 62%) (Scheme 75).

White solid, m.p 76-78° C., 168 mg, 62% yield; $^1$H NMR (400 MHz, CDCl$_3$) δ 7.39-7.28 (m, 5H), 4.86 (br, 1H), 4.58 (d, J=12 Hz, 1H), 4.53 (d, J=12 Hz, 1H), 3.86 (m, 2H), 2.25 (m, 1H), 1.96 (m, 1H), 1.87-1.65 (m, 3H), 1.59 (m, 1H); $^{13}$C NMR (100 MHz, CDCl$_3$) δ 137.9, 128.5, 127.9, 127.8, 84.0, 71.5, 61.1, 30.2, 29.4, 20.8; $^{19}$F NMR (376 MHz, CDCl$_3$) δ 52.0 (s); GC-MS ($t_R$): 18.9 mm; EI-MS (m/z): 273 [M]$^+$.

Embodiment 76

Preparation of benzyl N-fluorosulfonylvalinate

Scheme 76 Preparation of benzyl N-fluorosulfonylvalinate

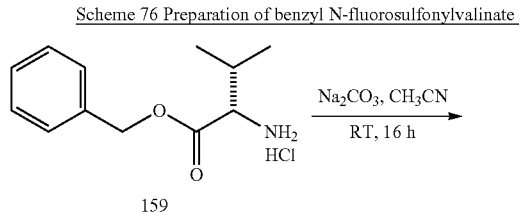

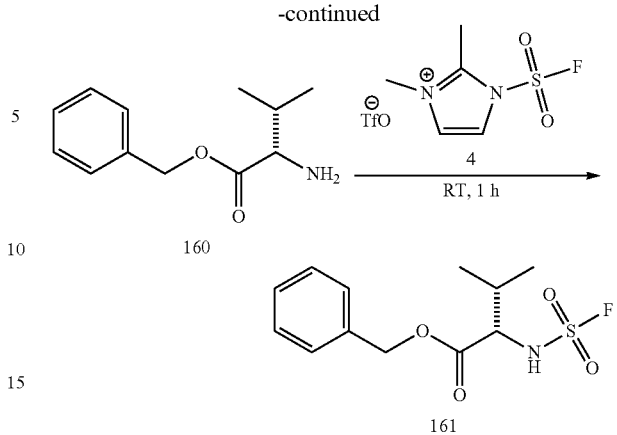

Benzyl(S)-valinate [Compound 159] (122 mg, 0.5 mmol) was dissolved in acetonitrile (2.5 mL), followed by addition of anhydrous sodium carbonate (106 mg, 1.0 mmol). The reaction mixture was stirred at room temperature for 16 hours, and then filtered to remove the solid, followed by addition of 1-(fluorosulfonyl)-2,3-dimethyl-1H-imidazolium trifluoromethanesulfonate [Compound 4] (164 mg, 0.5 mmol). The reaction mixture was stirred at room temperature for 1 hour. After completion of the reaction as indicated by TLC (petroleum ether ethyl acetate=5:1, product: $R_f$=0.7), water (20 mL) was added to the reaction mixture, which was then extracted with ethyl acetate (20 mL×2). The organic phase was washed with water (10 mL) and saturated brine (5 mL×2), dried over anhydrous sodium sulfate, and filtered through a filter paper. The filtrate was concentrated by a rotary evaporator and then suctioned by an oil pump to remove the residual solvent to give benzyl N-fluorosulfonylvalinate [Compound 161] as a colorless liquid (137 mg, 94%) (Scheme 76).

Colorless oil, 137 mg, 94% yield; $^1$H NMR (400 MHz, CDCl$_3$) δ 7.41-7.35 (m, 5H), 5.26 (d, J=12 Hz, 1H), 5.21 (d, J=12 Hz, 1H), 4.14 (d, J=4 Hz, 1H), 2.24 (m, 1H), 1.03 (d, J=7 Hz, 3H), 0.86 (d, J=7 Hz, 3H); $^{13}$C NMR (100 MHz, CDCl$_3$) δ 170.6, 134.6, 128.9, 128.8, 128.7, 68.2, 62.4, 31.4, 18.7, 16.9; $^{19}$F NMR (376 MHz, CDCl$_3$) δ 51.5; GC-MS ($t_R$): 17.4 min; EI-MS (m/z): 289 [M]$^+$.

Embodiment 77

Preparation of tert-butyl 3-(4-(tert-butoxy)phenyl)-2-(fluorosulfonyl)aminopropionate Scheme 77
Preparation of tert-butyl 3-(4-(tert-butoxy)phenyl)-2-(fluorosulfonyl)aminopropionate

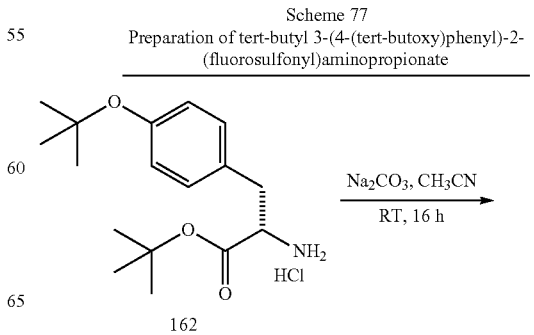

-continued

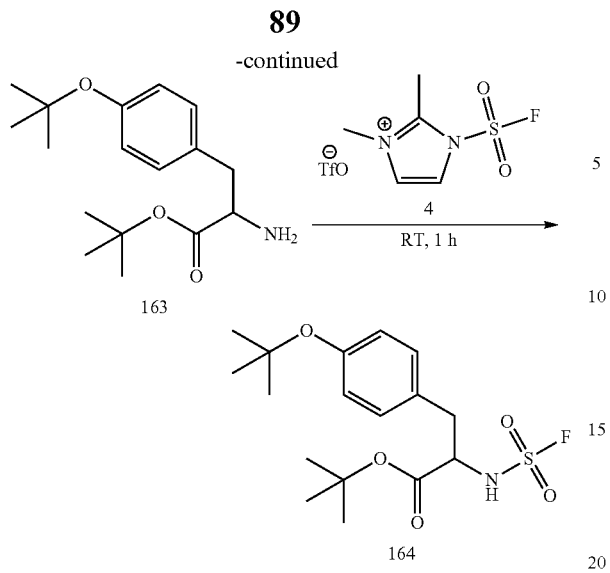

tert-Butyl (S)-3-(4-(tert-butoxy)phenyl)-2-aminopropionate [Compound 162] (165 mg, 0.5 mmol) was dissolved in acetonitrile (2.5 mL), followed by addition of anhydrous sodium carbonate (106 mg, 1.0 mmol). The resulting mixture was stirred at room temperature for 16 hours and then filtered to remove solid, followed by addition of 1-(fluorosulfonyl)-2,3-dimethyl-1H-imidazolium trifluoromethanesulfonate [compound 4] (164 mg, 0.5 mmol). The resulting mixture was stirred at room temperature for 1 hour. After completion of the reaction as indicated by TLC (petroleum ether:ethyl acetate=5:1, product: $R_f$=0.7), water (20 mL) was added to the reaction mixture, which was then extracted with ethyl acetate (20 mL×2). The organic phase was washed with water (10 mL) and saturated brine (5 mL×2), dried over anhydrous sodium sulfate, and filtered through a filter paper. The filtrate was concentrated by a rotary evaporator and then suctioned by an oil pump to remove the residual solvent to give tert-butyl 3-(4-tert-butoxy)phenyl)-2-(fluorosulfonyl) aminopropionate [Compound 164] as a colorless liquid (186 mg, 99%) (Scheme 77).

Colorless liquid, 186 mg, 99% yield; $^1$H NMR (400 MHz, CDCl$_3$) δ 7.08 (d, J=8 Hz, 2H), 6.93 (d, J=8 Hz, 2H), 5.56 (s, 1H), 4.36 (t, J=6 Hz, 1H), 3.16-3.05 (m, 2H), 1.41 (s, 9H), 1.33 (s, 9H); $^{13}$C NMR (100 MHz, CDCl$_3$) δ 169.0, 154.7, 130.1, 129.3, 124.3, 84.0, 78.6, 58.3, 38.1, 28.8, 27.8; $^{19}$F NMR (376 MHz, CDCl$_3$) δ 52.2; GC-MS ($t_R$): 20.9 min: EI-MS (m/z): 360 [M−Me]$^+$.

Embodiment 78

Preparation of N-fluorosulfonyl-α,α-dimethylbenzylamine

Scheme 78 Preparation of N-fluorosulfonyl-α, α-dimethylbeznylamine

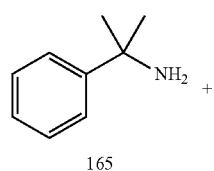

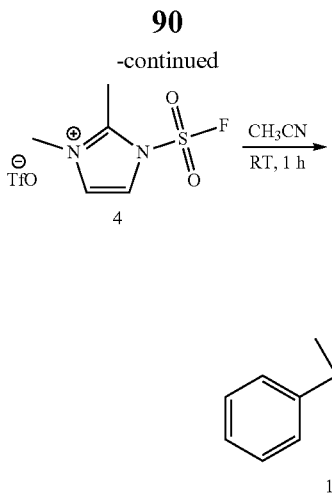

Cumylamine [compound 165] (135 mg, 1.0 mmol) was dissolved in acetonitrile (5.0 mL), followed by addition of 1-(fluorosulfonyl)-2,3-dimethyl-1H-imidazolium trifluoromethanesulfonate [compound 4] (328 mg, 1.0 mmol). The resulting mixture was stirred at room temperature for 1 hour. After completion of the reaction as indicated by TLC (petroleum ether 60-90:ethyl acetate=9:1, $R_f$=0.5), water (20 mL) was added to the reaction mixture, which was then extracted with ethyl acetate (30 mL). The organic phase was washed with water (20 mL×2) and saturated brine (10 mL×2), dried over anhydrous sodium sulfate, and filtered through a filter paper. The filtrate was concentrated by a rotary evaporator and then suctioned by an oil pump to remove the residual solvent to give N-fluorosulfonyl-α,α-dimethylbenzylamine [compound 166] as a pale yellow liquid (160 mg, 74%) (Scheme 78).

Pale yellow liquid, 160 mg, 74% yield; $^1$H NMR (400 MHz, CD$_3$CN) δ 7.51-7.28 (m, 5H), 7.13 (br, 1H), 1.71 (s, 6H): $^{13}$C NMR (100 MHz, CD$_3$CN) δ 146.0, 129.3, 128.3, 126.4, 61.2, 29.7; $^{19}$F NMR (376 MHz, CD$_3$CN) δ 59.7. HRMS (DART, m/z): calculated for C$_9$H$_{16}$FN$_2$O$_2$S: 235.0909 [M+NH$_4$]$^+$, found: 235.0911.

Embodiment 79

Preparation of methyl (S)—N-fluorosulfonyl-α-methylphenylalaninate

Scheme 79
Preparation of methyl (S)-N-fluorosulfonyl-α-methlphenylalaninate

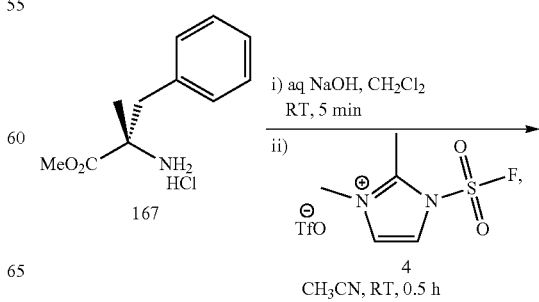

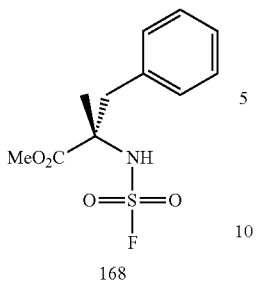

168

Methyl (S)-α-methylphenylalaninate hydrochloride [compound 167] (230 mg, 1.0 mmol) was added to 0.25M sodium hydroxide aqueous solution (4 mL), followed by addition of dichloromethane (5 mL). The resolution mixture was stirred at room temperature for 5 minutes. The organic phase was isolated, to which a solution (8 mL) of 1-(fluorosulfonyl)-2,3-dimethyl-1H-imidazolium trifluoromethanesulfonate [compound 4] (328 mg, 1.0 mmol) in acetonitrile was then added. The reaction mixture was stirred at room temperature for 0.5 hour. After completion of the reaction as indicated by TLC (petroleum ether 60-90:ethyl acetate=9:1, product: $R_f$=0.4), the reaction mixture was concentrated by a rotary evaporator, followed by addition of ethyl acetate (20 mL). The organic phase was washed with water (20 mL×2) and saturated brine (10 mL×2), dried over anhydrous sodium sulfate, and filtered through a filter paper. The filtrate was concentrated by a rotary evaporator and then suctioned by an oil pump to remove the residual solvent to give methyl (S)—N-fluorosulfonyl-α-methylphenylalaninate [compound 168] as a yellow liquid (205 mg, 75%) (Scheme 79).

Yellow liquid, 205 mg, 75% yield; $^1$H NMR (400 MHz, CDCl$_3$) δ 7.32-7.11 (m, 5H), 6.02 (br, 1H), 3.35 (d, J=14 Hz, 1H), 3.13 (d, J=14 Hz, 1H), 1.83 (s, 3H); $^{13}$C NMR (100 MHz, CDCl$_3$) δ 172.4, 134.5, 129.9, 128.7, 127.7, 64.8, 53.5, 44.1, 22.9; $^{19}$F NMR (376 MHz, CDCl$_3$) δ 60.3. HRMS (DART, m/z): calculated for C$_{11}$H$_{13}$FNO$_4$S: 274.0548 [M−H]$^-$, found: 274.0555.

Embodiment 80

Preparation of Ethyl (R)—N-fluorosulfonyl p-methylsulfonylphenylserinate

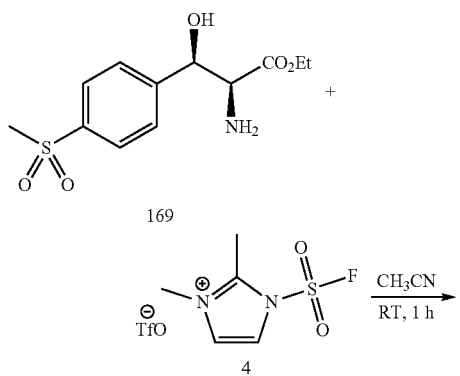

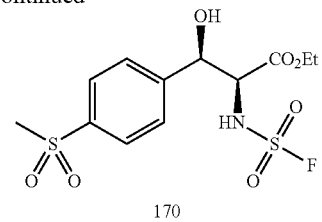

170

Ethyl (R)-p-methylsulfonylphenylserinate [compound 169] (287 mg, 1.0 mmol) was added into a solution (8 mL) of 1-(fluorosulfonyl)-2,3-dimethyl-1H-imidazolium trifluoromethanesulfonate [compound 4] (328 mg, 1.0 mmol) in acetonitrile. The resulting mixture was stirred at room temperature for 1 hour. After completion of the reaction as indicated by TLC (petroleum ether 60-90:ethyl acetate=1:2, $R_f$=0.5), water (25 mL) was added to the reaction mixture, which was then extracted with ethyl acetate (30 mL). The organic phase was washed with 0.1M hydrochloric acid (20 mL×2), saturated brine (10 mL×2), dried over anhydrous sodium sulfate, and filtered through a filter paper. The filtrate was concentrated by a rotary evaporator and then suctioned by an oil pump to remove the residual solvent to give ethyl (R)—(N-fluorosulfonyl) p-methylsulfonylphenylserinate [compound 170] as a white solid (267 mg, 72%) (Scheme 80).

White solid, decomposition at 136° C., 267 mg, 72% yield; $^1$H NMR (400 MHz, CD$_3$CN) δ 7.92 (d, J=8 Hz, 2H), 7.67 (d, J=8 Hz, 2H), 7.38 (br, 1H), 5.41 (d, J=3 Hz, 1H), 4.41 (d, J=3 Hz, 1H), 4.26 (m, 3H), 3.06 (s, 3H), 1.27 (t, J=7 Hz, 3H); $^{13}$C NMR (100 MHz, CD$_3$CN) δ 169.6, 147.6, 141.9, 128.9, 128.6, 73.3, 64.8, 63.8, 45.0, 14.9; $^{19}$F NMR (376 MHz, CD$_3$CN) δ 53.6 (s). HRMS (DART, m/z): calculated for C$_{12}$H$_{15}$FNO$_7$S$_2$: 368.0279 [M−H]$^-$, found: 368.0274.

Embodiment 81

Preparation of 4-chloroaniline sulfonyl fluoride

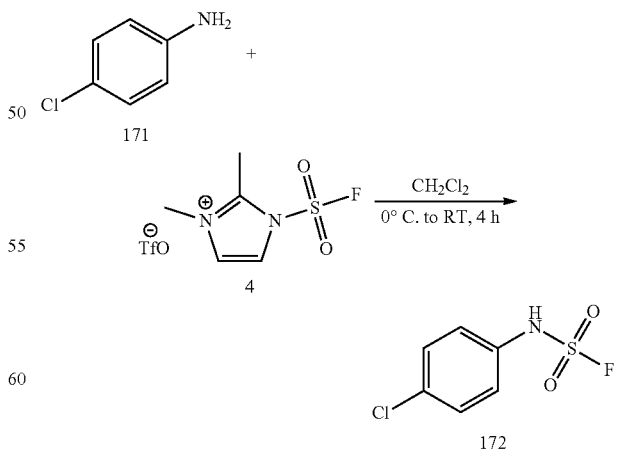

1-(Fluorosulfonyl)-2,3-dimethyl-1H-imidazolium trifluoromethanesulfonate [compound 4] (361 mg, 1.1 mmol) was suspended in dichloromethane (10 mL). The mixture was cooled in an ice bath and p-chloroaniline [compound 171] (128 mg, 1 mmol) was added thereto. After completion of the addition, the ice bath was removed and the reaction was allowed to run for 4 hours at room temperature. After completion of the reaction as indicated by LC-MS, column chromatography (silica gel 300-400 mesh, dichloromethane:ethyl acetate=20:1) afforded 4-chloroaniline sulfonyl fluoride [compound 172] as a pale yellow solid (185 mg, 88%) (Scheme 81).

Pale yellow solid, m.p. 44-48° C., 185 mg, 88% yield; $^1$H NMR (400 MHz, CDCl$_3$) δ 7.39 (m, 2H), 7.22 (m, 2H), 7.06 (br, 1H); $^{13}$C NMR (100 MHz, CDCl$_3$) δ 133.5 (s),132.3 (d, J=3 Hz), 130.0 (s), 124.6 (d, J=1 Hz); $^{19}$F NMR (376 MHz, CDCl$_3$) δ 50.5 (s, 1F); LC-MS (t$_R$): 1.52 min; ESI-MS (m/z): 208 [M−H]$^−$; HRMS (DART, m/z): calculated for C$_6$H$_4$NO$_2$ClFS: 207.9641 [M−H]$^−$, found: 207.9639.

Embodiment 82

Preparation of 4-fluoroaniline sulfonyl fluoride

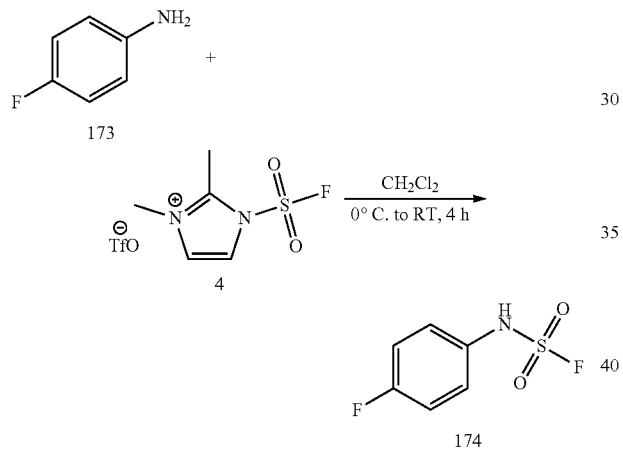

1-(Fluorosulfonyl)-2,3-dimethyl-1H-imidazolium trifluoromethanesulfonate [compound 4] (361 mg, 1.1 mmol) was suspended in dichloromethane (10 mL). The mixture was cooled in an ice bath and p-fluoroaniline [compound 173] (111 mg, 1 mmol) was added thereto. After completion of the addition, the ice bath was removed and the reaction was allowed to run for 4 hours at room temperature. After completion of the reaction as indicated by LC-MS, dichloromethane (20 mL) was added to the reaction mixture. The organic phase was washed with 0.1M hydrochloric acid (20 mL×3) and saturated brine (10 mL×2), dried over anhydrous sodium sulfate, and filtered through a filter paper. The filtrate was concentrated by rotary evaporator, and then suctioned by an oil pump to remove the residual solvent to give 4-fluoroaniline sulfonyl fluoride [compound 174] as a yellow oil (86 mg, 44%) (Scheme 82).

Yellow oil, 86 mg, 44% yield; $^1$H NMR (400 MHz, CDCl$_3$) δ 7.30 (m, 2H), 7.11 (m, 2H), 7.03 (br, 1H); $^{13}$C NMR (100 MHz, CDCl$_3$) δ 161.9 (d, J=247 Hz), 129.6 (t, J=3 Hz), 126.3 (dd, J=9 Hz. J=2 Hz), 116.8 (d, J=23 Hz); $^{19}$F NMR (376 MHz, CDCl$_3$) δ 49.9 (s, 1F), −113.4 (quin, J=4 Hz, 1F); LC-MS (t$_R$): 1.43 min; ESI-MS (m/z): 192 [M−H]$^−$.

Embodiment 83

Preparation of 3-Ethynylaniline Sulfonyl Fluoride

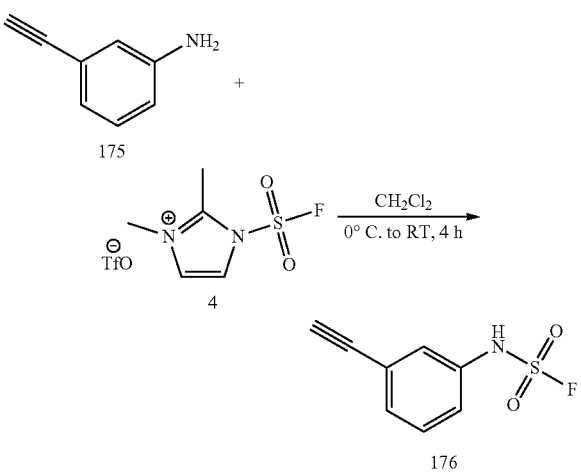

1-(Fluorosulfonyl)-2,3-dimethyl-1H-imidazolium trifluoromethanesulfonate [compound 4] (1807 mg, 5.5 mmol) was suspended in dichloromethane (50 mL). The mixture was cooled in an ice bath and 3-aminophenylacetylene [compound 175] (586 mg, 5 mmol) was added thereto. After completion of the addition, the ice bath was removed and the reaction was allowed to run for 4 hours at room temperature. After completion of the reaction as indicated by LC-MS, column chromatography (silica gel 300-400 mesh, dichloromethane:ethyl acetate=30:1) afforded 3-ethynylaniline sulfonyl fluoride [compound 176] as a yellow oil (882 mg, 88%) (Scheme 83).

Yellow oil, 882 mg, 88% yield; $^1$H NMR (400 MHz, CDCl$_3$) δ 7.44-7.35 (m, 3H), 7.28 (m, 1H), 7.08 (br, 1H), 3.15 (s, 1H); $^{13}$C NMR (100 MHz, CDCl$_3$) δ 134.0 (d, J=2 Hz), 131.1 (s), 129.9 (s), 126.2 (d, J=2 Hz), 124.0 (s), 123.3 (d, J=1 Hz), 82.2 (s), 79.0 (s); $^{19}$F NMR (376 MHz, CDCl$_3$) δ 50.9 (d, J=4 Hz, 1F); LC-MS (t$_R$): 1.46 min: ESI-MS (m/z): 198 [M−H]$^−$; HRMS (DART, m/z): calculated for C$_8$H$_5$NO$_2$FS: 198.0031 [M−H]$^−$, found: 198.0029.

Embodiment 84

Preparation of 4-isopropylaniline sulfonyl fluoride

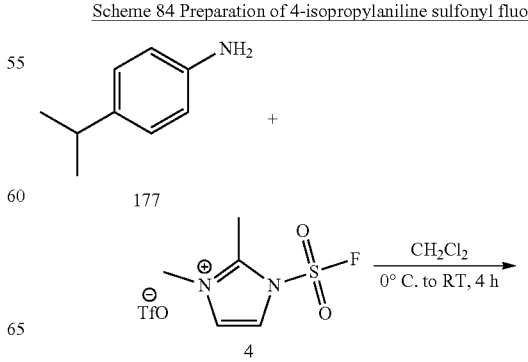

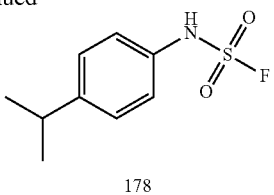

178

1-(Fluorosulfonyl)-2,3-dimethyl-1H-imidazolium trifluoromethanesulfonate [compound 4] (361 mg, 1.1 mmol) was suspended in dichloromethane (10 mL). The mixture was cooled in an ice bath, and 4-isopropylaniline [compound 177] (135 mg, 1 mmol) was added thereto. After completion of the addition, the ice bath was removed and the reaction was allowed to run for 4 hours at room temperature. After completion of the reaction as indicated by LC-MS, dichloromethane (20 mL) was added to the reaction mixture. The organic phase was washed with 0.1M hydrochloric acid (20 mL×3) and saturated brine (10 mL×2), dried over anhydrous sodium sulfate, and filtered through a filter paper. The filtrate was concentrated by rotary evaporator and then suctioned by an oil pump to remove the residual solvent to give 4-isopropylaniline sulfonyl fluoride [Compound 178] as a purple oil (191 mg, 88%) (Scheme 84).

Purple oil, 191 mg, 88% yield; $^1$H NMR (400 MHz, CDCl$_3$) δ 7.24 (m, 4H), 6.88 (br, 1H), 2.92 (sept, J=6.8 Hz, 1H), 1.24 (d, J=6.8 Hz, 6H); $^{13}$C NMR (100 MHz, CDCl$_3$) δ 148.7 (s), 131.4 (d, J=2 Hz), 127.8 (s), 123.7 (d, J=2 Hz), 33.8 (s), 23.9 (s); $^{19}$F NMR (376 MHz, CDCl$_3$) δ 50.5 (s, 1F); LC-MS (t$_R$): 1.61 min; ESI-MS (m/z): 216 [M−H]$^-$.

Embodiment 85

Preparation of 4-methoxyaniline sulfonyl fluoride

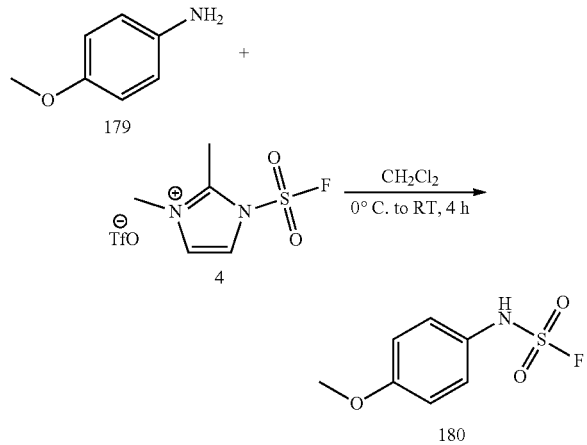

Scheme 85 Preparation of 4-methoxyaniline sulfonyl fluoride 1-(Fluorosulfonyl)-2,3-dimethyl-1H-imidazolium trifluoromethanesulfonate [Compound 4] (361 mg, 1.1 mmol) was suspended in dichloromethane (10 mL). The mixture was cooled in an ice bath, and p-methoxyaniline [Compound 179] (123 mg, 1 mmol) was added thereto. After completion of the addition, the ice bath was removed and the reaction was allowed to run for 4 hours at room temperature. After completion of the reaction as indicated by LC-MS, dichloromethane (20 mL) was added to the reaction mixture. The organic phase was washed with 0.1M hydrochloric acid (20 mL×3) and saturated brine (10 mL×2), dried over anhydrous sodium sulfate, and filtered through a filter paper. The filtrate was concentrated by a rotary evaporator and then suctioned by an oil pump to remove the residual solvent to give 4-methoxyaniline sulfonyl fluoride [compound 180] as a purple oil (187 mg, 91%) (Scheme 85).

Purple oil, 187 mg, 91% yield; $^1$H NMR (400 MHz, CDCl$_3$) δ 7.25 (m, 2H), 6.92 (m, 2H), 6.82 (br 1H), 3.82 (s, 3H); $^{13}$C NMR (100 MHz, CDCl$_3$) δ 159.3 (s), 126.8 (d, J=2 Hz), 126.2 (d, J=2 Hz), 115.0 (s), 55.7 (s); $^{19}$F NMR (376 MHz, CDCl$_3$) δ 49.2 (s, 1F); LC-MS (t$_R$): 1.41 min; ESI-MS (m/z): 204 [M−H]$^-$.

Embodiment 86

Preparation of 3-methoxyaniline sulfonyl fluoride

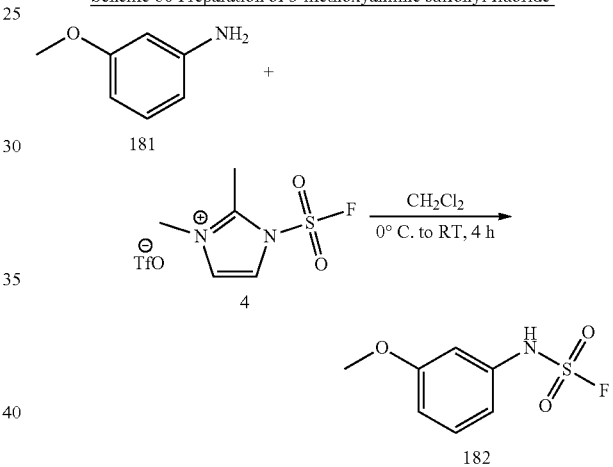

Scheme 86 Preparation of 3-methoxyaniline sulfonyl fluoride 1-(Fluorosulfonyl)-2,3-dimethyl-1H-imidazolium trifluoromethanesulfonate [compound 4] (361 mg, 1.1 mmol) was suspended in dichloromethane (10 mL). The mixture was cooled in an ice bath, and m-aminoanisole [compound 181] (123 mg, 1 mmol) was added thereto. After completion of the addition, the ice bath was removed and the reaction was allowed to run for 4 hours at room temperature. After completion of the reaction as indicated by LC-MS, dichloromethane (20 mL) was added to the reaction mixture. The organic phase was washed with 0.1M hydrochloric acid (20 mL×3) and saturated brine (10 mL×2), dried over anhydrous sodium sulfate, and filtered through a filter paper. The filtrate was concentrated by a rotary evaporator and then suctioned by an oil pump to remove the residual solvent to give 3-methoxyaniline sulfonyl fluoride [compound 182] as a red oil (183 mg, 89%) (Scheme 86).

Red oil, 183 mg, 89% yield; $^1$H NMR (400 MHz, CDCl$_3$) δ 37.30 (t, J=8 Hz, 1H), 7.22 (br, 1H), 6.84 (m, 3H), 3.81 (s, 6H); $^{13}$C NMR (100 MHz, CDCl$_3$) δ 160.5 (s), 135.1 (d, J=2 Hz), 130.6 (s), 114.9 (d, J=2 Hz),112.9 (s), 108.7 (d, J=2 Hz), 55.6 (s); $^{19}$F NMR (376 MHz, CDCl$_3$) δ 50.4 (s, 1F); LC-MS (t$_R$): 1.43 min; ESI-MS (m/z): 204 [M−H]$^-$.

Embodiment 87

Preparation of 4-fluorosulfonyloxyaniline sulfonyl fluoride

Scheme 87 Preparation of 4-fluorosulfonyloxyaniline sulfonyl fluoride

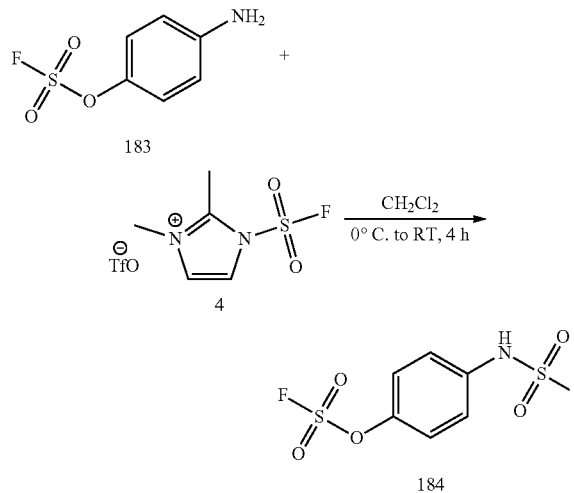

1-(Fluorosulfonyl)-2,3-dimethyl-1H-imidazolium trifluoromethanesulfonate [compound 4] (361 mg, 1.1 mmol) was suspended in dichloromethane (10 mL). The mixture was cooled in an ice bath, and 4-aminophenoxysulfonyl fluoride [compound 183] (191 mg, 1 mmol) was added thereto. After completion of the addition, the ice bath was removed and the reaction was allowed to run for 4 hours at room temperature. After completion of the reaction LC-MS, column chromatography (silica gel 300-400 mesh, dichloromethane:ethyl acetate=20:1) afforded 4-fluorosulfonyloxyaniline sulfonyl fluoride [compound 184] as a pale yellow solid (203 mg, 74%) (Scheme 87).

Pale yellow solid, m.p. 106-111° C., 203 mg, 74% yield; $^1$H NMR (400 MHz, CD$_3$CN) δ 9.11 (br, 1H), 7.53 (m, 2H), 7.47 (m, 2H); $^{13}$C NMR (100 MHz, CD$_3$CN) δ 148.9 (s), 136.3 (d, J=3 Hz), 125.1 (d, J=2 Hz), 123.5 (d, J=1 Hz); $^{19}$F NMR (376 MHz, CD$_3$CN) δ 50.7 (s, 1F), 38.1 (s, 1F); LC-MS (t$_R$): 1.52 min; ESI-MS (m/z): 272 [M–H]$^-$; HRMS (DART, m/z): calculated for C$_6$H$_4$NO$_5$F$_2$S$_2$: 271.9504 [M–H]$^-$, found: 271.9501.

Embodiment 88

This embodiment studies the stability of 1-(fluorosulfonyl)-2,3-dimethyl-1H-imidazolium trifluoromethanesulfonate in different humidity environments.

Experimental method: 1-(fluorosulfonyl)-2,3-dimethyl-1H-imidazolium trifluoromethanesulfonate was sampled (4.521 g, 4.298 g, 4.273 g) and placed into three plastic bottles (20 mL), which were then sealed with parafilm membrane. The three plastic bottles were placed on an experimental table (22° C.), in a refrigerator (4° C.) or in a dryer (22° C.). After 231 days of observation and testing, the results are shown in Table 1.

TABLE 1

| Different humidity environment | The substance placed on the experimental table (22° C.) | The substance placed in the refrigerator (4° C.) | The substance placed in the dryer (22° C.) |
| --- | --- | --- | --- |
| Observation of the state of the substance | White paste with a few bubbles | White powder with a few large agglomerations. | White powder with many small agglomerations |
| NMR identification of the substance | $^1$H NMR spectrum showed noise peaks, $^{19}$F NMR spectrum had noise peaks and the S-F signal decreased by 25% | $^1$H NMR spectrum did not change, and the S-F signal in $^{19}$F NMR spectrum decreased by 1% | $^1$H NMR spectrum showed noise peaks, and the S-F signal in $^{19}$F-NMR spectrum decreased by 4% |

In addition, 231 days later, three equal parts of triethylamine (220 μL, 1.59 mmol) were added into three systems of the solution of 4-cumylphenol [compound 32] (225 mg, 1.04 mmol) in acetonitrile (1 mL) at room temperature. After the mixture was stirred for 10 minutes, the solutions of 1-(fluorosulfonyl)-2-3-dimethyl-1H-imidazolium trifluoromethanesulfonate [Compound 4] (425 mg, 1.29 mmol) that were placed on the experimental table (22° C.), in the refrigerator (4° C.) and in the dryer (22° C.) in acetonitrile (1 mL) were added to the respective systems in one portion. The reaction was carried out for 1 hour under argon atmosphere, during which time the reaction was monitored by TLC (petroleum ether ethyl acetate=10:1, product: R$_f$=0.68). The mixtures were subjected to column chromatography (silica gel 300-400 mesh, petroleum ether ethyl acetate=10:1) to give 4-(2-phenyl-2-propyl)phenoxysulfonyl fluoride [compound 33] as a colorless liquid (Scheme 88). The results are shown in Table 2:

TABLE 2

| Different humidity environment | The substance placed on the experimental table (22° C.) | The substance placed in the refrigerator (4° C.) | The substance placed in the dryer (22° C.) |
| --- | --- | --- | --- |
| After the reaction, the mass of the obtained compound 33 | 226 mg | 298 mg | 298 mg |
| After the reaction, the yield of obtained compound 33 | 73% | 97% | 97% |

Scheme 88
Preparation of
4-(2-phenyl-2-propyl)phenoxysulfonyl fluoride

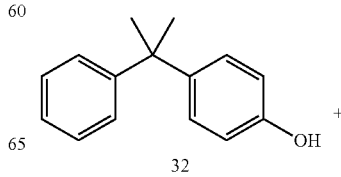

-continued

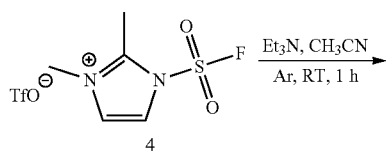

4

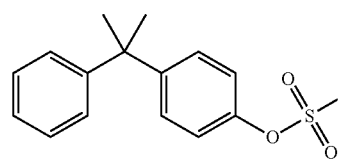

33

Embodiment 89

This embodiment studies the melting range and thermal stability of 1-(fluorosulfonyl)-2,3-dimethyl-1H-imidazolium trifluoromethanesulfonate Experimental method: On a melting point meter, the temperature was set at 30-70° C. and the heating gradient at 0.5° C./min, the melting range of the substance of the embodiment was measured to be 62.1-64.2° C.: the temperature was set at 129-240° C. and the heating gradient at 1.0° C./min, the substance slowly bubbled at 135.2° C., and then turned from colorless to pale yellow at 176.5° C., turned to yellow at 185.6° C., turned to dark yellow at 189.9° C., and finally turned to black at 199.4° C.

Embodiment 90

This embodiment studies the stability of 1-(fluorosulfonyl)-2,3-dimethyl-1H-imidazolium trifluoromethanesulfonate in deionized water The experimental method: 1-(fluorosulfonyl)-2,3-dimethyl-1H-imidazolium trifluoromethanesulfonate (36 mg, 0.1 mmol) was dissolved in deionized water (1 mL) at room temperature to prepare a solution, and the pH value of the obtained solution was measured to be pH=1, $^{19}$F-NMR tracked the change of the S—F signal of the solution, and the results are shown in Table 3.

TABLE 3

| | Standing time | | | | |
|---|---|---|---|---|---|
| | 12 min | 30 min | 58 min | 2 h | 2 h 46 min | 13 h 19 min |
| S-F signal of the solution | 0.77 | 0.58 | 0.35 | 0.11 | 0.05 | — |

Embodiment 91

Preparation of 1-(fluorosulfonyl)-2,3-dimethyl-1H-imidazolium fluorosulfonate

Scheme 91
Preparation of 1-(fluorosulfonyl)-2,3-dimethyl-1H-imidazolium trifluoromethanesulfonate

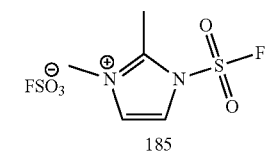

185

2-Methylimidazole [Compound 1] (1.65 g, 20 mmol) was added to a suspension of sodium carbonate (5.31 g, 50 mmol) in acetonitrile (20 mL) at room temperature. The reaction system was degassed to generate negative pressure by a water pump, and then sulfuryl fluoride gas [Compound 2] (0.6 L, 24 mmol) was introduced from a balloon filled with the gas. The reaction mixture was stirred overnight. After completion of the reaction as indicated by TLC (petroleum ether:ethyl acetate=10:1, product: $R_f$=0.44), the reaction mixture was filtered through silica gel (10-40 mesh), the filter cake was washed with dichloromethane (40 mL), and the filtrate was extracted with distilled water (100 mL×3). The combined aqueous phase was back extracted with dichloromethane (40 mL). The combined organic phase was washed with saturated brine (40 mL), and dried over anhydrous sodium sulfate. The filtrate was concentrated by a rotary evaporator (as the boiling point of 2-methyl-1H-imidazole-1-sulfonyl fluoride is relatively low, the temperature was controlled below 20° C. and the pressure was controlled above 140 torr during concentration) to give 6.72 g of a mixed solution of 2-methyl-1H-imidazole-1-sulfonyl fluoride [Compound 3], dichloromethane and acetonitrile. After being quantified with p-toluenesulfonyl fluoride, the amount of the product was 3.07 g and the yield was 93.5%. Dichloromethane (18 mL) was added to the mixed solution prepared above under nitrogen atmosphere. The resulting mixture was cooled to 0° C. in an ice bath, and methyl fluorosulfonate (1.5 mL, 18.7 mmol) was slowly added to the mixture under stirring dropwise by a syringe. The ice bath was allowed to naturally melt and warm to room temperature, and the reaction was allowed to run for 2 hours. After completion of the reaction as indicated by LC-MS, the reaction mixture was concentrated by a rotary evaporator to give a viscous oil, to which methyl tert-butyl ether (20 mL) was added. The resulting mixture was stirred, during which time a solid precipitated out. The supernatant was poured out. The solid was washed with methyl tert-butyl ether (20 mL×2) and then suctioned by an oil pump to remove the residual solvent to give 1-(fluorosulfonyl)-2,3-dimethyl-1H-imidazolium fluorosulfonate [Compound 185] as a white solid (4.78 g, 91.8%; overall yield 86%) (Scheme 91).

White solid, m.p. 172-176° C., 4.77 g, overall yield 86%; $^1$H NMR (400 MHz, CD$_3$CN) δ 7.89 (d, J=2.8 Hz, 1H), 7.60 (d, J=2.8 Hz, 1H), 3.88 (s, 3), 2.87 (s, 3H); $^{13}$C NMR (100 MHz, CD$_3$CN) δ 151.4, 125.5, 122.1, 37.5, 12.9; $^{19}$F NMR (376 MHz, CD$_3$CN) δ 61.4 (s, 1F), 38.2 (s, 1F); HRMS (DART, m/z): Calculated for C$_5$H$_8$O$_2$N$_2$FS: 179.0285 [M]$^+$, Found: 179.0287; HRMS (DART, m/z): Calculated for O$_3$FS: 98.9558 [M]$^-$, Found: 98.9562.

Embodiment 92

Preparation of 1-(fluorosulfonyl)-2-methyl-1H-imidazolium bisulfate

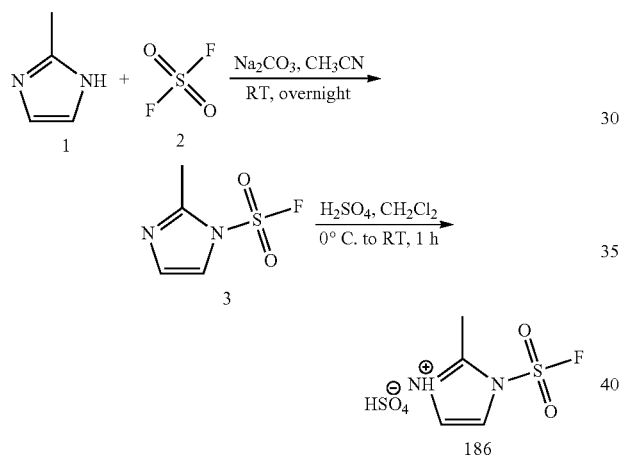

2-Methylimidazole [Compound 1] (1.64 g, 20 mmol) was added to a suspension of sodium carbonate (5.31 g, 50 mmol) in acetonitrile (20 mL) at room temperature. The reaction system was degassed to generate negative pressure by a water pump, and then sulfuryl fluoride gas [Compound 2] (0.6 L, 24 mmol) was introduced from a balloon filled with the gas. The reaction mixture was stirred overnight. After completion of the reaction as indicated by TLC (petroleum ether:ethyl acetate=10:1, product: R$_f$=0.44), the reaction mixture was filtered through silica gel (10-40 mesh), and the filter cake was washed with dichloromethane (40 mL). The filtrate was extracted with distilled water (100 mL×3), and then the combined aqueous phase was back extracted with dichloromethane (40 mL). The combined organic phase was washed with saturated brine (40 mL) and dried over anhydrous sodium sulfate. The filtrate was concentrated by a rotary evaporator (as the boiling point of 2-methyl-1H-imidazole-1-sulfonyl fluoride is relatively low, the temperature was controlled below 20° C. and the pressure was controlled above 140 torr during concentration) to give 5.89 g of a mixed solution of 2-methyl-1H-imidazole-1-sulfonyl fluoride [Compound 3], dichloromethane and acetonitrile. After being quantified with p-toluenesulfonyl fluoride, the amount of the product was 3.00 g and the yield was 91.5%. Dichloromethane (18 mL) was added to the mixed solution prepared above under nitrogen atmosphere. The resulting mixture was cooled to 0° C. in an ice bath, and concentrated sulfuric acid (980 μL, 18.3 mmol) was slowly added dropwise to the mixture under stirring by a syringe. The ice bath was allowed to naturally melt and warm to room temperature, and the reaction was allowed to run for 2 hours. After completion of the reaction as indicated by LC-MS, the reaction mixture was concentrated by a rotary evaporator to give a viscous oil, to which methyl tert-butyl ether (30 mL) was then added. The resulting mixture was stirred, during which time a solid precipitated out. The supernatant was poured out. The solid was washed with methyl tert-butyl ether (20 mL×2) and then suctioned by an oil pump to remove the residual solvent to give 1-(fluorosulfonyl)-2-methyl-1H-imidazolium bisulfate [Compound 186] as a white solid (4.38 g, 91.3%; overall yield 83.5%) (Scheme 1).

On a melting point meter, the heating gradient was set at 1° C./min, the sample started to melt at 99.2° C., completely melted to be milky white liquid at 100.6° C., and started bubbling at 106.3° C. and gradually became colorless and transparent liquid.

White solid, 4.38 g, overall yield 83.5%; $^1$H NMR (400 MHz, CD$_3$CN) δ 10.31 (s, 2H), 7.81 (d, J=2.4 Hz, 1H), 7.57 (d, J=2.4 Hz, 1), 2.93 (s, 3H); $^{13}$C NMR (100 MHz, CD$_3$CN) δ 151.8, 122.9, 122.1, 14.0; $^{19}$F NMR (376 MHz, CD$_3$CN) δ 61.6 (s, 1F); HRMS (DART, m/z): Calculated for C$_4$H$_6$O$_2$N$_2$FS: 165.0129 [M]$^+$, Found: 165.0130; HRMS (DART, m/z): Calculated for HO$_4$S: 96.9601 [M]$^-$, Found: 96.9602.

Embodiment 93

Preparation of 1-(fluorosulfonyl)-3-methyl-1H-imidazolium fluorosulfonate

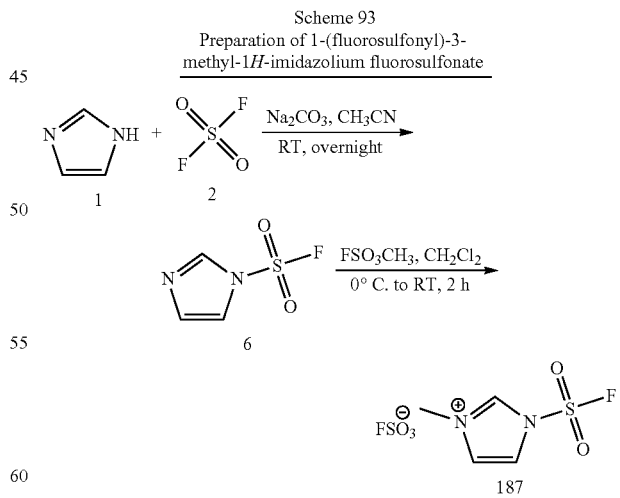

Imidazole [Compound 5] (1.36 g, 20 mmol) was added to a suspension of sodium carbonate (5.31 g, 50 mmol) in acetonitrile (20 mL) at room temperature. The reaction system was degassed to generate negative pressure by a water pump, and then sulfuryl fluoride gas [Compound 2]

(0.6 L, 24 mmol) was introduced from a balloon filled with the gas. The resulting mixture was stirred overnight. After completion of the reaction as indicated by TLC (petroleum ether:ethyl acetate=10:1, $R_f$=0.48), the reaction mixture was filtered through silica gel (10-40 mesh), and the filter cake was washed with dichloromethane (40 mL). The filtrate was extracted with distilled water (100 mL×3), and then the combined aqueous phase was back extracted with dichloromethane (40 mL). The combined organic phase was washed with saturated brine (40 mL) and dried over anhydrous sodium sulfate. The filtrate was concentrated by a rotary evaporator (as the boiling point of 1H-imidazole-1-sulfonyl fluoride is relatively low, the temperature was controlled below 20° C. and the pressure was controlled above 140 torr during concentration) to give 5.79 g of a mixed solution of 1H-imidazole-1-sulfonyl fluoride [Compound 6], dichloromethane and acetonitrile. After being quantified with p-toluenesulfonyl fluoride, the amount of the product was 2.49 g and the yield was 83%. Dichloromethane (16 mL) was added to the mixed solution prepared above under nitrogen atmosphere. The resulting mixture was cooled to 0° C. in an ice bath, and methyl fluorosulfonate (1.35 mL, 16.6 mmol) was slowly added to the mixture under stirring by a syringe. After the dropwise addition, the ice bath was removed and the reaction was allowed to run for 2 hours at room temperature. After completion of the reaction as indicated by LC-MS, the reaction mixture was concentrated by a rotary evaporator to give a viscous oil, to which methyl tert-butyl ether (20 mL) was then added. The resulting mixture was stirred, during which time a solid precipitated out. The supernatant was poured out. The solid was washed with methyl tert-butyl ether (20 mL×2) and then suctioned by an oil pump to remove the residual solvent to give 1-(fluorosulfonyl)-3-methyl-1H-imidazolium fluorosulfonate [compound 17] as a white solid (4.33 g, 98.7%; overall yield 81.9/*)(Scheme 93).

White solid, m.p. 169-173° C., 4.33 g, over yield 81.9%; $^1$H NMR (400 MHz, CD$_3$CN) δ 9.50 (s, 1H), 8.02 (s, 1H), 7.72 (s, 1H), 4.01 (s, 3H); $^{13}$C NMR (100 MHz, CD$_3$CN) δ 141.3, 127.7, 122.4, 38.6; $^{19}$F NMR (376 MHz, CD$_3$CN) δ 61.2 (s, 1F), 38.3 (s, 1F); HRMS (DART, m/z): Calculated for C$_4$H$_6$O$_2$N$_2$FS: 165.0129 [M]$^+$, Found: 165.0130; HRMS (DART, m/z): Calculated for O$_3$FS: 98.9558 [M]$^-$, Found 98.9562.

Embodiment 94

Preparation of 1-(fluorosulfonyl)-2-isopropyl-3-methyl-1H-imidazolium trifluoromethanesulfonate Scheme 94
Preparation of 1-(fluorosulfonyl)-2-isopropyl-3-methyl-1H-imidazolium trifluoromethanesulfonate

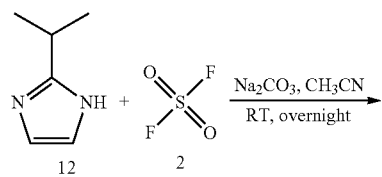

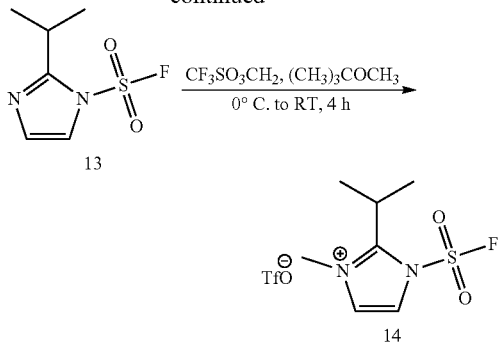

2-Isopropylimidazole [Compound 12] (2.21 g, 20 mmol) was added to a suspension of sodium carbonate (5.30 g, 50 mmol) in acetonitrile (20 mL) at room temperature. The reaction system was degassed to generate negative pressure by a water pump, and then sulfuryl fluoride gas [Compound 2] (0.8 L, 32 mmol) was introduced from a balloon. The reaction mixture was stirred overnight, during which time the reaction was monitored by LC-MS. The reaction mixture was filtered through silica gel (10-40 mesh), and the filter cake was washed with ethyl acetate (40 mL). The organic phase was washed with distilled water (100 mL×3), and then the combined aqueous phase was back extracted by ethyl acetate (40 mL). The combined organic phase was washed with saturated brine (40 mL), dried over anhydrous sodium sulfate, and filtered through a filter paper. The filtrate was concentrated by a rotary evaporator and subjected to column chromatography (silica gel 300-400 mesh, petroleum ether:dichloromethane=5:1) to give 2-isopropyl-1-H-imidazole-1-sulfonyl fluoride [compound 13] as a pale yellow oil (583 mg, 15%).

Pale yellow oil, 583 mg, 15% yield $^1$HNMR (400 MHz, CDCl$_3$) δ 7.32 (d, J=1.8 Hz, 1H), 7.03 (d, J=1.8 Hz, 1H), 3.47 (sept, J=6.8 Hz, 1H), 1.38 (d, J=6.8 Hz, 6H); $^{13}$C NMR (100 MHz, CDCl$_3$) δ 155.8, 128.9 (d, J=19 Hz),119.8, 27.7, 21.7; $^{19}$F NMR (376 MHz, CDCl$_3$) δ 58.9 (s, 1F); HRMS (DART, m/z): Calculated for C$_6$H$_{10}$O$_2$N$_2$FS: 193.0442 [M+H]$^+$, Found: 193.0441.

Under nitrogen atmosphere, dichloromethane (2.7 mL) was added to the 2-isopropyl-1-H-imidazole-1-sulfonyl fluoride [compound 13] (519 mg, 2.7 mmol) prepared above. The resulting mixture was cooled to 0° C. in an ice bath, and methyl trifluoromethanesulfonate (305 μL, 2.7 mmol) was slowly added to the mixture under stirring by a syringe. After completion of the dropwise addition, the ice bath was removed, and the reaction was allowed to run for 8 hours at room temperature, during which time the reaction was monitored by TLC. The reaction mixture was concentrated by a rotary evaporator, followed by addition of methyl ten-butyl ether (20 mL). The resulting mixture was stirred, during which time a solid precipitated out. The supernatant was poured out. The solid was washed with methyl tert-butyl ether (20 mL×3) and then suctioned by an oil pump to remove the residual solvent to give 1-(fluorosulfonyl)-2-isopropyl-3-methyl-1H-imidazolium trifluoromethanesulfonate [Compound 14] as a white solid (646 mg, 67%) (Scheme 94).

White solid, m.p. 77-80° C., 646 mg, 67% yield; $^1$HNMR (400 MHz, CD$_3$CN) δ 7.85 (d, J=2.6 Hz, 1H), 7.54 (d, J=2.6 Hz, 1H), 3.94 (m, 4H), 1.52 (d, J=7.2 Hz, 6H); $^{13}$C NMR (100 MHz, CD$_3$CN) δ 155.5, 126.5, 123.1, 122.0 (q, J=318 Hz), 39.1, 27.8, 18.2; $^{19}$F NMR (376 MHz, CD$_3$CN) δ 62.1

(s, 1F), −78.1 (s, 3F); HRMS (DART, in): Calculated for C₇H₁₂O₂N₂FS: 207.0598 [M]⁺, Found: 207.0600; HRMS (DART, m/z): Calculated for CO₃F₃S: 148.9526 [M]⁻, Found: 148.9525.

Embodiment 95

Preparation of 1-(fluorosulfonyl)-3-methyl-1H-benzimidazolium trifluoromethanesulfonate

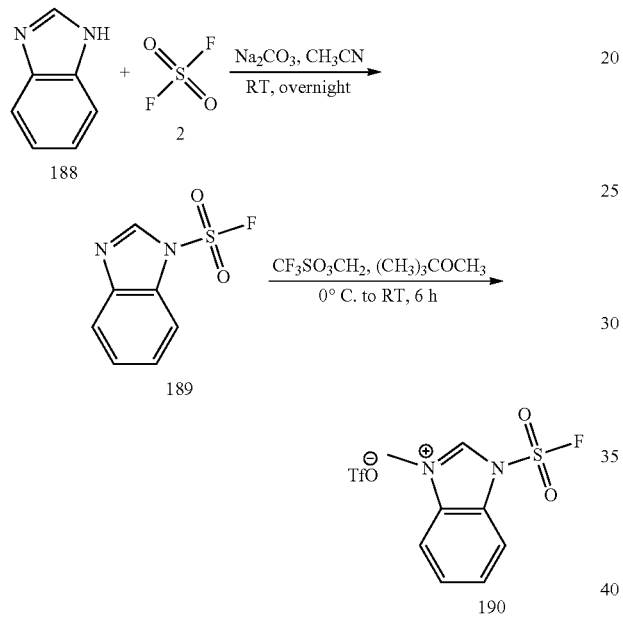

Benzimidazole [Compound 188] (2.37 g, 320 mmol) was added to a suspension of sodium carbonate (5.31 g, 50 mmol) in acetonitrile (20 mL) at room temperature. The reaction system was degassed to generate negative pressure by a water pump, and then sulfuryl fluoride gas [Compound 2] (0.8 L, 32 mmol) was introduced from a balloon filled with the gas. The reaction mixture was stirred overnight, during which time the reaction was monitored by LC-MS. The reaction mixture was filtered through silica gel (10-40 mesh), and the filter cake was washed with ethyl acetate (40 mL). The organic phase was washed with distilled water (100 mL×3), and then the combined aqueous phase was combined and back extracted with ethyl acetate (40 mL). The combined organic phase was washed with saturated brine (40 mL), dried over anhydrous sodium sulfate, and filtered through a filter paper. The filtrate was concentrated by a rotary evaporator, and subjected to column chromatography (silica gel 300-400 mesh, petroleum ether:dichloromethane=2:3) to give 1H-benzimidazole-1-sulfonyl fluoride [Compound 189] as a white solid (2.64 g, 66%).

White solid, m.p. 40-42° C., 2.64 g, 66% yield; ¹H NMR (400 MHz, CDCl₃) δ 8.27 (s, 1H), 7.90-7.80 (m, 2H), 7.55-7.48 (m, 2H); ¹³C NMR (100 MHz, CDCl₃) δ 143.4 (d, J=1.7 Hz), 140.3 (d, J=1.5 Hz), 130.5, 126.9, 126.3, 121.8, 112.6; ¹⁹F NMR (376 MHz, CDCl₃) δ 56.4 (s); HRMS (DART, m/z): Calculated for C₇H₆O₂N₂FS: 201.0129 [M+H]⁺, Found: 201.0128.

Under nitrogen atmosphere, dichloromethane (13 mL) was added to the 1H-benzimidazole-1-sulfonyl fluoride [compound 189] (2.57 g, 12.8 mmol) prepared above. The resulting mixture was cooled to ° C. in an ice bath, and methyl trifluoromethanesulfonate (1.45 mL, 12.8 mmol) was slowly added to the mixture under stirring by a syringe. After the completion of the dropwise addition, the ice bath was removed, and the reaction was allowed to run for 6 hours at room temperature, during which time the reaction was monitored by TLC. The reaction mixture was concentrated by a rotary evaporator to give a white solid, which was dissolved in acetonitrile (4 mL), followed by addition of methyl tert-butyl ether (40 mL). The resulting mixture was stirred, during which time a solid precipitated out. The supernatant was poured out. The solid was washed with methyl tert-butyl ether (20 mL×3) and then suctioned by an oil pump to remove the residual solvent to give 1-(fluorosulfonyl)-3-methyl-1H-benzimidazolium trifluoromethanesulfonate [compound 190] as a white solid (3.24 g, 69%) (Scheme 95).

White solid, m.p. 121-125° C., 3.24 g, 69% yield; ¹HNMR (400 MHz. CD₃CN) δ 9.91 (s, 1H), 8.11-8.05 (m, 2H), 7.98-7.90 (m, 2H), 4.25 (s, 3H); ¹³C NMR (100 MHz, CD₃CN) δ 145.8, 133.3, 131.5, 130.4, 129.3, 121.8 (q, J=318 Hz), 116.2, 115.0, 36.1; ¹⁹F NMR (376 MHz, CD₃CN) δ 59.8 (s, 1F), −78.1 (s, 3F); HRMS (DART, m/z): Calculated for C₈H₁₀O₃N₂FS: 233.0391 [M+H₂O]⁺, Found: 233.0392; HRMS (DART, m/z): Calculated for CO₃F₃S: 148.9526 [M]⁻, Found: 148.9525.

Embodiment 96

Preparation of Aniline Sulfonyl Fluoride

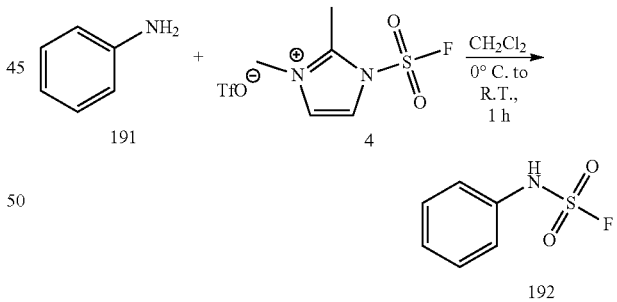

1-(Fluorosulfonyl)-2,3-dimethyl-1H-imidazolium trifluoromethanesulfonate [compound 4] (3.61 g, 1 mmol) was suspended in dichloromethane (50 mL). The mixture was cooled in an ice bath, and aniline [compound 191] (932 mg, 10 mmol) was added. After completion of the addition, the ice bath was removed and the reaction was allowed to run for 1 hour at room temperature. After completion of the reaction as indicated by LC-MS, the reaction mixture was diluted with dichloromethane (100), washed with 0.1 M hydrochloric acid (100 mL×3) and saturated brine (50 mL×2), dried over anhydrous sodium sulfate and filtered through a filter paper. The filtrate was concentrated by a rotary evaporator and then suctioned by an oil pump to remove the residual solvent to give aniline sulfonyl fluoride [compound 192] as a yellow oil (1.55 g, 88%) (Scheme 96).

Yellow solid, 1.55 g, 88% yield; $^1$H NMR (400 MHz, CD$_3$CN) δ 8.85 (br, 1H), 7.44 (m, 2H), 7.33 (m, 3H); $^{13}$C NMR (101 MHz, CD$_3$CN) δ 135.6 (d, J=2.7 Hz), 130.7, 128.1, 123.9 (d, J=1.8 Hz); F NMR (376 MHz, CD$_3$CN) δ 50.1 (s). HRMS (DART, m/z): calculated for C$_6$H$_5$NO$_2$FS: 174.0031 [M−H]$^−$, found: 174.0029.

Embodiment 97

Preparation of 4-hydroxyaniline sulfonyl fluoride

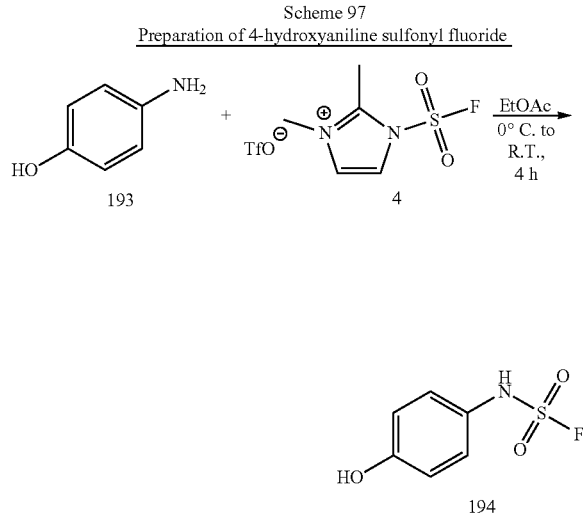

Embodiment 98

Preparation of N-phenylbis(fluorosulfonyl)imine

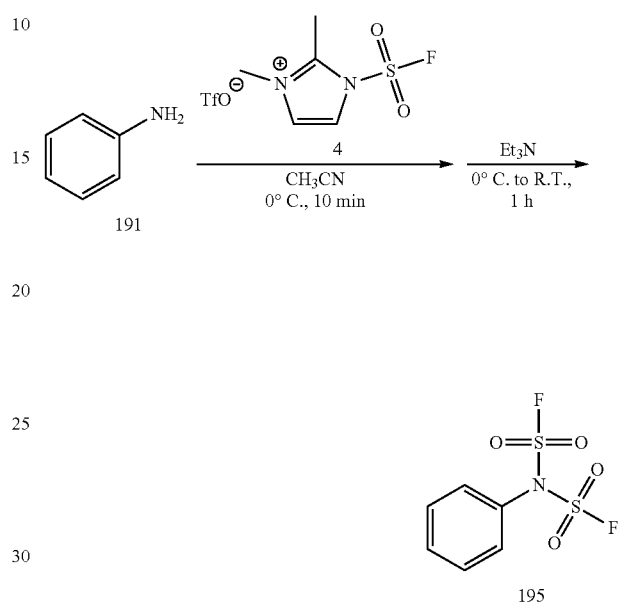

1-(Fluorosulfonyl)-2,3-dimethyl-1H-imidazolium trifluoromethanesulfonate [compound 4] (361 mg, 1.1 mmol) was suspended in dichloromethane (10 mL). The mixture was cooled in an ice bath, and 4-aminophenol [compound 193] (109 mg, 1 mmol) was added. After completion of the addition, the ice bath was removed and the reaction was allowed to run for 4 hours at room temperature. After completion of the reaction as indicated by LC-MS, the reaction mixture was diluted with ethyl acetate (20 mL), washed with 0.1M hydrochloric acid (20 mL×3) and saturated brine (20 mL×2), dried over anhydrous sodium sulfate, and filtered through a filter paper. The filtrate was concentrated by a rotary evaporator and then suctioned by an oil pump to remove the residual solvent to give 4-hydroxyaniline sulfonyl fluoride [compound 194] as a brown oil (174 mg, 891%) (Scheme 97).

Brown oil, 174 mg, 91% yield; $^1$H NMR (400 MHz, CDCl$_3$) δ 7.21-7.17 (m, 2H), 6.89 (br, 1H), 6.86-6.82 (m, 2H), 6.53 (br, 1H); $^{13}$C NMR (100 MHz, CD$_3$CN) δ 157.6, 127.8 (d, J=1.9 Hz), 126.9 (d, J=2.7 Hz), 117.1; $^{19}$F NMR (376 MHz, CDCl$_3$) δ 48.7 (s, 1F). HRMS (DART, m/z): calculated for C$_6$H$_5$FNO$_2$S: 189.9980 [M−H]$^−$, found: 189.9977.

Aniline [Compound 191] (460 μL, 5.0 mmol) was dissolved in acetonitrile (20 mL). The mixture was cooled in an ice bath, and 1-(fluorosulfonyl)-2,3-dimethyl-1H-imidazolium trifluoromethanesulfonate [Compound 4] (4.27 g, 13 mmol) was added. After the mixture was stirred for 10 minutes, triethylamine (360 μL, 2.6 mmol) was added thereto. After completion of the addition, the ice bath was removed, and the reaction was allowed to run for 1 hour at room temperature. After completion of the reaction as indicated by TLC (petroleum ether:ethyl acetate=9:1, product: R$_f$=0.65), the reaction mixture was concentrated by a rotary evaporator, followed by addition of ethyl acetate (25 mL). The organic phase was washed with 0.1 M hydrochloric acid (30 mL×3), deionized water (40 mL×2) and saturated brine (40 mL×2), dried over anhydrous sodium sulfate, and filtered through a filter paper. The filtrate was concentrated by a rotary evaporator and then suctioned by an oil pump to remove the residual solvent to give N-phenylbis(fluorosulfonyl)imine [Compound 195] as a yellow solid (1.05 g, 81%) (Scheme 98).

Yellow solid, m.p. 41-43° C., 1.05 g, 81% yield; $^1$H NMR (400 MHz, CD$_3$CN) δ 7.72-7.62 (m); $^{13}$C NMR (101 MHz, CD$_3$CN) δ 134.1 (t, J=1.8 Hz), 133.7, 131.9, 130.3 (t, J=1.2 Hz); $^{19}$F NMR (376 MHz, CD$_3$CN) δ 56.9 (s); HRMS (DART, m/z): calculated for C$_6$H$_9$F$_2$N$_2$O$_4$S$_2$: 274.9966 [M+NH$_4$]$^+$, found: 274.9965.

Embodiment 99

Preparation of N-(3,4-methylenedioxy)phenyl bis(fluorosulfonyl)imine

Scheme 99
Preparation of N-(3,4-methylenedioxy)phenyl bis(fluorosulfonyl)imine

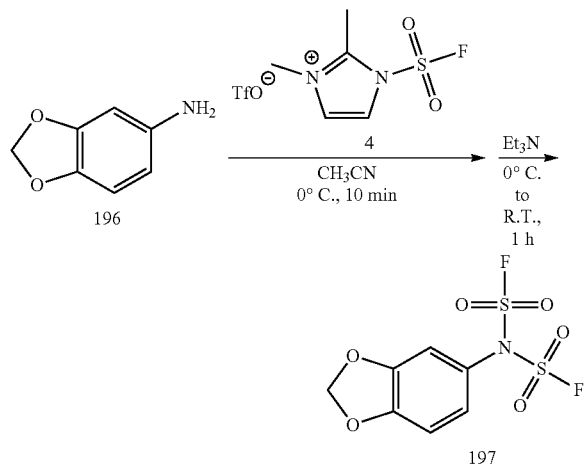

3,4-Methylenedioxy aniline [Compound 196] (137 mg, 1.0 mmol) was dissolved in acetonitrile (5 mL), followed by addition of 1-(fluorosulfonyl)-2,3-dimethyl-1H-imidazolium trifluoromethanesulfonate [Compound 4] (820 mg, 2.5 mmol) to the solution under an ice bath. After the mixture was stirred for 10 minutes, triethylamine (69 μL, 0.5 mmol) was added thereto. After completion of the addition of triethylamine, the ice bath was removed, and the reaction was allowed to run for 1 hour at room temperature. After completion of the reaction as indicated by LC-MS, column chromatography (silica gel 300-400 mesh, petroleum ether:dichloromethane=6:1) afforded N-(3,4-methylenedioxy)phenyl bis(fluorosulfonyl)imine [compound 197] as a yellow solid (259 mg, 86%) (Scheme 99).

Yellow solid, m.p. 49-51° C., 259 mg, 86% yield; $^1$H NMR (400 MHz, CDCl$_3$) δ 7.01 (m, 1H), 6.90 (m, 2H), 6.11 (s, 2H); $^{13}$C NMR (101 MHz, CDCl$_3$) δ 151.1, 149.3, 125.7, 124.0, 109.6, 109.3, 103.0; $^{19}$F NMR (376 MHz, CDCl$_3$) δ 55.2 (s). HRMS (DART, m/z): calculated for C$_7$H$_4$NO$_6$F$_2$S$_2$: 299.9443 [M−H]$^-$, found: 299.9451.

Embodiment 100

Preparation of N-(4-ethynyl)phenyl bis(fluorosulfonyl)imine

Scheme 100
Preparation of N-(4-ethynyl)phenyl bis(fluorosulfonyl)imine

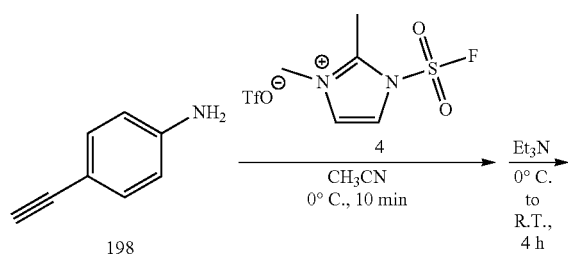

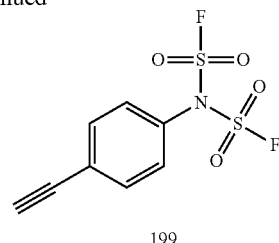

4-Ethynylaniline [Compound 198] (117 mg, 1.0 mmol) was dissolved in acetonitrile (5 mL), followed by addition of 1-(fluorosulfonyl)-2,3-dimethyl-1H-imidazolium trifluoromethanesulfonate [Compound 4] (821 mg, 2.5 mmol) to the solution under an ice bath. The resulting mixture was stirred for 10 minutes, followed by addition of triethylamine (69 μL, 0.5 mmol). After completion of the addition, the ice bath was removed, and the reaction was allowed to run for 4 hours at room temperature. After completion of the reaction as indicated by LC-MS, column chromatography (silica gel 300-400 mesh, petroleum ether:dichloromethane=4:1) afforded N-(4-ethynyl)phenylbis(fluorosulfonyl)imine [compound 199] as a pale yellow solid (203 ng, 72%) (Scheme 100).

Pale yellow solid, m.p. 53-56° C., 203 ng, 72% yield; $^1$H NMR (400 MHz, CDCl$_3$) δ 7.66 (m, 2H), 7.45 (m, 2H), 3.27 (s, 1H); $^{13}$C NMR (101 MHz, CDCl$_3$) δ 134.4, 132.8 (t, J=1.8 Hz), 129.3 (t, J=1.4 Hz), 127.0, 81.5, 81.3; $^{19}$F NMR (376 MHz, CDCl$_3$) δ 56.2 (s). HRMS (DART, m/z): calculated for C$_8$H$_9$N$_2$O$_4$F$_2$S$_2$: 298.9966 [M+NH$_4$]$^+$, found: 298.9965.

Embodiment 101

Preparation of N-3-fluorophenyl bis(fluorosulfonyl)imine

Scheme 101
Preparation of N-3-fluorophenyl bis(fluorosulfonyl)imine

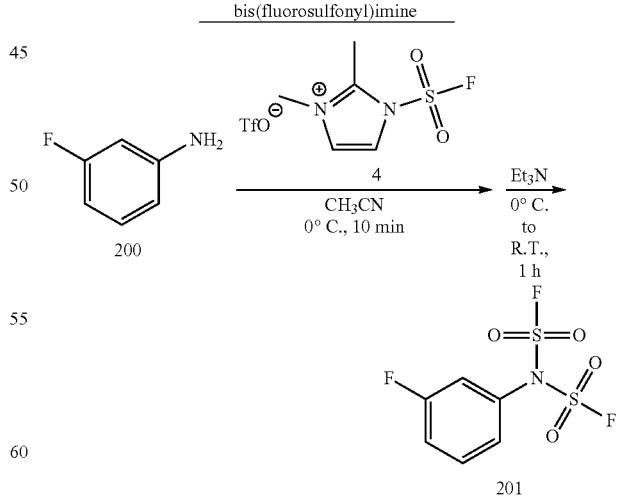

3-Fluoroaniline [Compound 198] (111 mg, 1.0 mmol) was dissolved in acetonitrile (5 mL), followed by addition of 1-(fluorosulfonyl)-2,3-dimethyl-1H-imidazolium trifluoromethanesulfonate [Compound 4] (821 mg, 2.5 mmol) to the solution under an ice bath. The resulting mixture was stirred for 10 minutes, and then triethylamine (69 μL, 0.5 mmol) was added. After completion of the reaction, the ice bath was removed, and the reaction was allowed to run for 1 hour at room temperature. After completion of the reaction as indicated by LC-MS, column chromatography (silica gel 300-400 mesh, petroleum ether:dichloromethane=4:1) afforded N-3-fluorophenyl bis(fluorosulfonyl)imine [compound 201] as a colorless oily liquid (177 mg, 64%) (Scheme 101).

Colorless oil, 177 mg, 64% yield; $^1$H NMR (400 MHz, CD$_3$CN) δ 7.67 (m, 1H), 7.56 (m, 2H), 7.48 (m, 1H); $^{13}$C NMR (101 MHz, CDCl$_3$) δ 163.0 (d, J=251.1 Hz), 133.8 (d, J=9.9 Hz), 132.0 (d, J=9.0 Hz), 125.3 (d, J=3.6 Hz), 120.0 (d, J=20.5 Hz), 117.2 (d, J=24.0 Hz); $^{19}$F NMR (376 MHz, CD$_3$CN) δ 57.3 (s, 2F), −108.8 (m, 1H), HRMS (DART, m/z): calculated for C$_6$H$_8$N$_2$O$_4$F$_3$S$_2$: 292.9872 [M+NH$_4$]$^+$, found: 292.9871.

Embodiment 102

Preparation of N-(2,6-diisopropyl)phenyl bis(fluorosulfonyl)imine

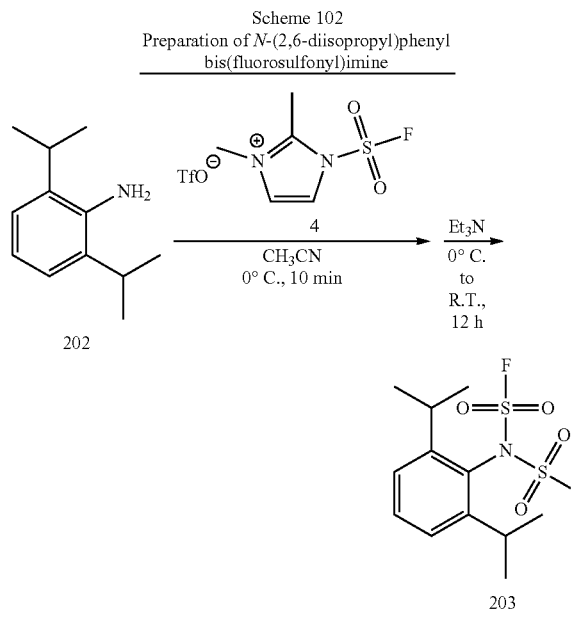

2,6-Diisopropylaniline [Compound 202] (177 mg, 1.0 mmol) was dissolved in acetonitrile (5 mL), followed by addition of 1-(fluorosulfonyl)-2,3-dimethyl-1H-imidazolium trifluoromethanesulfonate [Compound 4] (821 mg, 2.5 mmol) to the solution under an ice bath. After the mixture was stirred for 10 minutes, triethylamine (69 μL, 0.5 mmol) was added. After completion of the addition, the ice bath was removed, and the reaction was carried out at room temperature for 12 hours. After completion of the reaction as indicated by LC-MS, column chromatography (silica gel 300-400 mesh, petroleum ether:dichloromethane=9:1) afforded N-(2,6-diisopropyl) phenyl bis(fluorosulfonyl)imine [compound 203] as a colorless oily liquid (180 mg, 53%) (Scheme 102).

White solid, m.p. 110-114° C., 180 mg, 53% yield, 1H NMR (400 MHz, CDCl$_3$) δ 7.51 (t, J=7.8 Hz, 1H), 7.30 (d, J=7.8 Hz, 2H), 3.13 (sept, J=6.8 Hz, 2H), 1.28 (d, J=6.8 Hz, 12H); $^{13}$C NMR (101 MHz, CDCl$_3$) δ 149.1, 132.7, 129.1, 126.0, 29.5, 24.0; $^{19}$F NMR (376 MHz, CDCl$_3$) δ 55.2 (s); HRMS (DART, m/z): calculated for C$_{12}$H$_{21}$N$_2$O$_4$F$_2$S$_2$: 359.0905 [M+NH$_4$]$^+$, found: 359.0904.

Embodiment 103

Preparation of N-(2-phenoxy)ethyl bis(fluorosulfonyl)imine

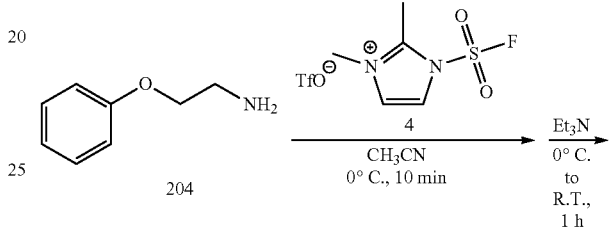

2-Phenoxyethylamine [Compound 204] (137 mg, 1.0 mmol) was dissolved in acetonitrile (5 mL), followed by addition of 1-(fluorosulfonyl)-2,3-dimethyl-1H-imidazolium trifluoromethanesulfonate [Compound 4] (821 mg, 2.5 mmol) to the solution under an ice bath. The resulting mixture was stirred for 10 minutes, followed by addition of triethylamine (69 μL, 0.5 mmol). After completion of the addition, the ice bath was removed, and the reaction was allowed to run for 1 hour at room temperature. After completion of the reaction as indicated by LC-MS, the reaction mixture was diluted with ethyl acetate (20 mL), washed with deionized water (20 mL×3) and saturated brine (20 mL×2), dried over anhydrous sodium sulfate, and filtered through a filter paper. The filtrate was concentrated by a rotary evaporator and then suctioned by an oil pump to remove the residual solvent to give N-(2-phenoxy)ethyl bis(fluorosulfonyl)imide [Compound 201] as a yellow oil (291 mg, 96%) (Scheme 103).

Yellow oil, 291 mg, 96% yield; $^1$H NMR (400 MHz, CDCl$_3$) δ 7.31 (m, 2H), 7.02 (M, 1H), 6.90 (m, 2H), 4.42 (t, J=5.1 Hz, 2H), 4.26 (t, J=5.1 Hz, 2H); $^{13}$C NMR (101 MHz, CDCl$_3$) δ 157.7, 129.8, 122.1, 114.6, 64.1, 54.0; $^{19}$F NMR (376 MHz, CDCl$_3$) δ 58.4 (s); HRMS (DART, m/z): calculated for C$_8$H$_9$NO$_3$F$_2$S$_2$: 300.9885 [M]$^+$, found: 300.9884.

Embodiment 104

Preparation of N-phenyl bis(fluorosulfonyl)imine

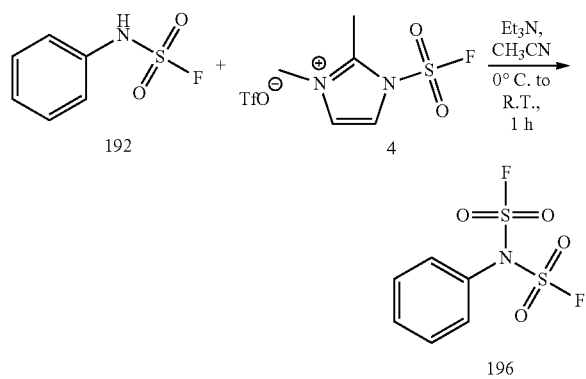

Aniline sulfonyl fluoride [compound 192] (175 mg, 1.0 mmol) was dissolved in acetonitrile (5 mL), followed by addition of 1-(fluorosulfonyl)-2,3-dimethyl-1H-imidazolium trifluoromethanesulfonate [compound 4] (492 mg, 1.5 mmol) and triethylamine (360 μL, 2.6 mmol) to the solution under an ice bath. After completion of the addition, the ice bath was removed, and the reaction was allowed to run for 1 hour at room temperature. After completion of the reaction as indicated by LC-MS, the reaction mixture was diluted with ethyl acetate (20 mL), washed with deionized water (20 mL×3) and saturated brine (20 mL×2), dried over anhydrous sodium sulfate, and filtered through a filter paper. The filtrate was concentrated by a rotary evaporator and then suctioned by an oil pump to remove the residual solvent to give N-phenyl bis(fluorosulfonyl)imine [Compound 195] as a pale yellow solid (212 mg, 82%) (Scheme 104).

Pale yellow solid, m.p. 41-43° C., 212 mg, 82% yield; $^1$H NMR (400 MHz, CD$_3$CN) δ 7.72-7.62 (m); $^{13}$C NMR (101 MHz, CD$_3$CN) δ 134.1 (t, J=1.8 Hz), 133.7, 131.9, 130.3 (t, J=1.2 Hz); $^{19}$F NMR (376 MHz, CD$_3$CN) δ 56.9 (s).

Embodiment 105

Preparation of benzenesulfonic acid isopropylbenzylamide

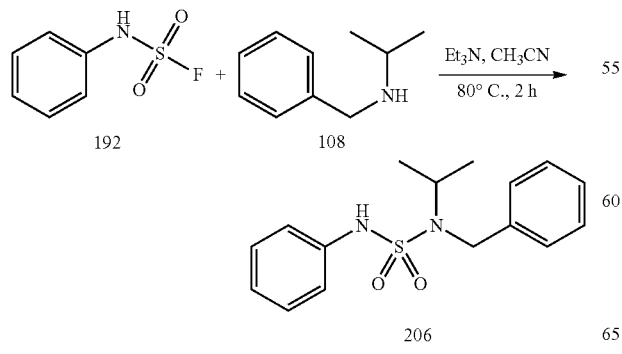

N-Benzylisopropylamine [compound 108] (224 mg, 1.5 mmol) was dissolved in acetonitrile (5 mL) at room temperature, followed by addition of triethylamine (208 μL, 1.5 mmol) and aniline sulfonyl fluoride [compound 192] (175 mg, 1.0 mmol). After completion of the addition, the reaction mixture was heated to 80° C. in an oil bath, and the reaction was allowed to run for 2 hours. After completion of the reaction as indicated by LC-MS, the reaction mixture was restored to room temperature and diluted with ethyl acetate (20 mL), washed with 1 M hydrochloric acid (20 mL×3) and saturated brine (20 mL×2), dried over anhydrous sodium sulfate, and filtered through a filter paper. The filtrate was concentrated by a rotary evaporator and then suctioned by an oil pump to remove the residual solvent to give benzenesulfonic acid isopropylbenzylamide [compound 206] as a white solid (271 mg, 89%) (Scheme 105).

White solid, m.p. 91-95° C., 271 mg, 89% yield; $^1$H NMR (400 MHz, CD$_3$CN) δ 7.67 (br, 1H), 7.33-7.09 (m, 10H), 4.35 (s, 2H), 4.00 (sept, J=6.7 Hz, 1H), 0.97 (d, J=6.8 Hz, 6H). $^{13}$C NMR (101 MHz, CD$_3$CN) δ 140.2, 139.1, 130.1, 129.1, 128.5, 128.0, 124.8, 120.6, 51.5, 48.2, 21.3. HRMS (DART, m/z): calculated for C$_{16}$H$_{21}$O$_2$N$_2$S: 305.1318 [M+H]$^+$, found: 305.1315.

Embodiment 106

Preparation of fluorosulfonyl azide (FSO$_2$N$_3$)

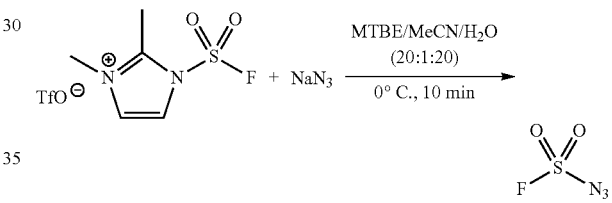

Under an ice bath, a solution of 1-(fluorosulfonyl)-2,3-dimethyl-1H-imidazolium trifluoromethanesulfonate (6 mmol 9, 1 mL MeCN) in acetonitrile was added into a mixture of sodium azide aqueous solution (0.25 M, 20 mL; containing 5 mmol NaN$_3$) and methyl tert-butyl ether (20 mL). The reaction mixture was stirred in an ice bath for 10 minutes, followed by standing at room temperature (25° C.) for 5 minutes. The aqueous phase in the reaction system was removed, and the obtained organic phase was fluorosulfonyl azide (FSO$_2$N$_3$) solution with a yield of 92% (determined by signal integration of $^{19}$F NMR, relative to the mole number of the sodium azide used). The obtained solution can be directly used for diazo transfer reaction of primary amino compounds without further purification.

Embodiment 107

Preparation of 4-benzylpiperidine-1-sulfonyl fluoride

Scheme 107 Preparation of 4-benzylpiperidine-1-sulfonyl fluoride

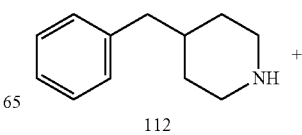

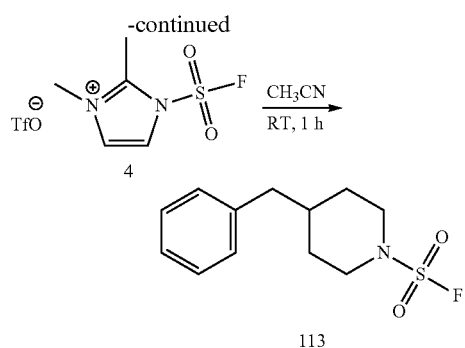

4-Benzylpiperidine [compound 112] (175 mg, 1 mmol) was dissolved in acetonitrile (2 mL) at room temperature, followed by addition of 1-(fluorosulfonyl)-2,3-dimethyl-1H-imidazolium trifluoromethanesulfonate [compound 4] (329 mg, 1 mmol). The reaction was allowed to run for 1 hour. After completion of the reaction as indicated by LC-MS, water (10 mL) was added to the reaction mixture, which was then extracted with ethyl acetate (10 mL×3). The combined organic phase was washed with water (15 mL) and saturated brine (15 mL), dried over anhydrous sodium sulfate, and filtered through a filter paper. The filtrate was concentrated by a rotary evaporator and then suctioned by an oil pump to remove the residual solvent to give 4-benzylpiperidine-1-sulfonyl fluoride [compound 113] as a pale yellow solid (254 mg, 99%) (Scheme 107).

Pale yellow solid, m.p. 58-61° C., 254 mg, 99% yield: $^1$H NMR (400 MHz, CDCl$_3$) δ 7.30-7.11 (m, 5H), 3.90-3.85 (m, 2H), 2.94-2.85 (m, 2H), 2.56 (d, J=6.8 Hz, 2H), 1.75-1.62 (m, 3H), 1.35 (dq, J=4 Hz, J=11.6 Hz, 2H); $^{13}$C NMR (100 MHz, CDCl$_3$) δ 139.4, 129.1, 128.5, 126.3, 47.6, 42.6, 37.0, 30.7; $^{19}$F NMR (376 MHz, CDCl$_3$) δ 39.6 (s, 1F); LC-MS (t$_R$): 1.71 min: ESI-MS (m/z) 258 [MH]$^+$.

Embodiment 108

Preparation of 4-benzylpiperidine-1-sulfonyl fluoride

Scheme 108 Preparation of 4-benzylpiperidine-1-sulfonyl fluoride

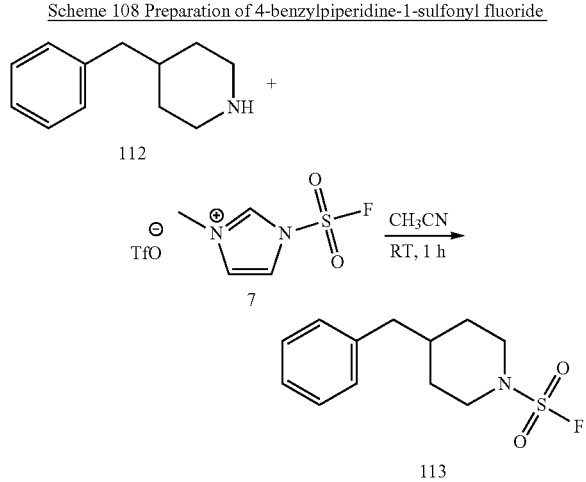

4-Benzylpiperidine [compound 112] (175 mg, 1 mmol) was dissolved in acetonitrile (2 mL) at room temperature, followed by addition of 1-(fluorosulfonyl)-2,3-dimethyl-1H-imidazolium trifluoromethanesulfonate [compound 7] (314 mg, 1 mmol). The reaction was allowed to run for 1 hour. After completion of the reaction as indicated by LC-MS, water (10 mL) was added to the reaction mixture, which was then extracted with ethyl acetate (10 mL×3). The combined organic phase was washed with water (15 mL) and saturated brine (15 mL), dried over anhydrous sodium sulfate, and filtered through a filter paper. The filtrate was concentrated by a rotary evaporator and then suctioned by an oil pump to remove the residual solvent to give 4-benzylpiperidine-1-sulfonyl fluoride [Compound 113] as a pale yellow solid (238 mg, 92%) (Scheme 108).

Pale yellow solid, m.p. 58-61° C., 238 mg, 92% yield; $^1$H NMR (400 MHz, CDCl$_3$) δ 7.30-7.11 (m, 5H), 2.94-2.85 (m, 2H), 2.56 (d, J=6.8 Hz, 2H), 1.75-1.62 (m, 3H), 1.35 (dq, J=4 Hz, J=11.6 Hz, 2H; $^{19}$F NMR (376 MHz, CDCl$_3$) δ 39.6 (s, 1F); LC-MS (t$_R$): 1.71 min; ESI-MS (m/z): 258 [MH]$^+$.

Embodiment 109

Preparation of 4-benzylpiperidine-1-sulfonyl fluoride

Scheme 109 Preparation of 4-benzylpiperidine-1-sulfonyl fluoride

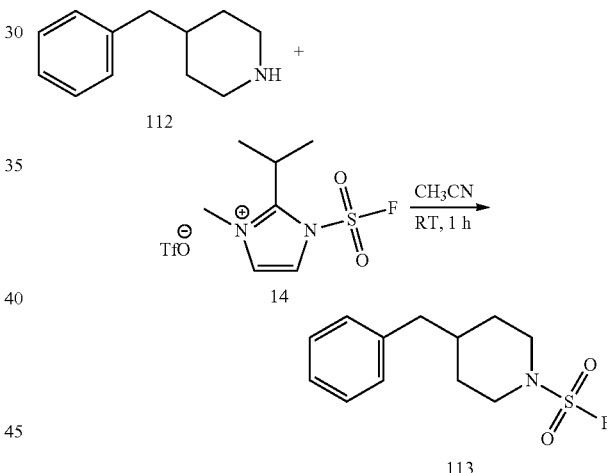

4-Benzylpiperidine [Compound 112] (175 mg, 1 mmol) was dissolved in acetonitrile (2 mL) at room temperature, followed by addition of 1-(fluorosulfonyl)-2,3-dimethyl-1H-imidazolium trifluoromethanesulfonate [Compound 14] (357 mg, 1 mmol). The reaction was allowed to run for 1 hour. After completion of the reaction as indicated by LC-MS, water (10 mL) was added to the reaction mixture, which was then extracted with ethyl acetate (10 mL×3). The combined organic phase was washed with water (15 mL) and saturated brine (15 mL), dried over anhydrous sodium sulfate, and filtered through a filter paper. The filtrate was concentrated by a rotary evaporator, and subjected to column chromatography (silica gel 300-400 mesh, petroleum ether:ethyl acetate=20:1) to give 4-benzylpiperidine-1-sulfonyl fluoride [compound 113] as a pale yellow solid (215 mg, 84%) (Scheme 109).

Pale yellow solid, m.p. 58-61° C., 215 mg, 84% yield, 1H NMR (400 MHz, CDCl$_3$) δ 7.30-7.11 (m, 5H), 3.90-3.85 (m, 2H), 2.94-2.85 (m, 2H), 2.56 (d, J=6.8 Hz, 2H), 1.75-1.62

(m, 3H), 1.35 (dq, J=4 Hz, J=11.6 Hz, 2H); $^{19}$F NMR (376 MHz, CDCl$_3$) δ 39.6 (s, 1F); LC-MS (t$_R$): 1.71 min; ESI-MS (m/z): 258 [M]$^+$.

Embodiment 111

Preparation of 4-benzylpiperidine-1-sulfonyl fluoride

Scheme 111 Preparation of 4-benzylpiperidine-1-sulfonyl fluoride

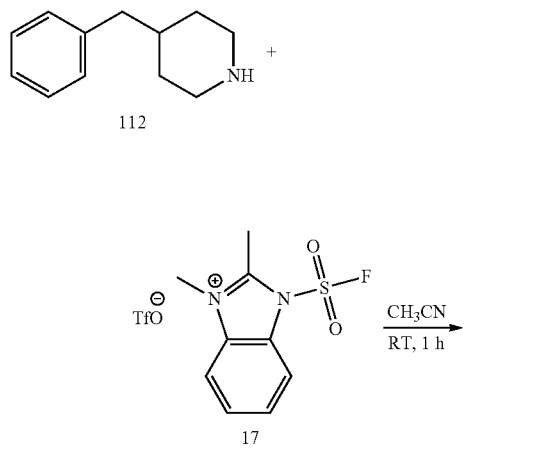

4-Benzylpiperidine [compound 112] (175 mg, 1 mmol) was dissolved in acetonitrile (2 mL) at room temperature, followed by addition of 1-(fluorosulfonyl)-2,3-dimethyl-1H-imidazolium trifluoromethanesulfonate [compound 17] (379 mg, 1 mmol). The reaction was allowed to run for 1 hour. After completion of the reaction as indicated by LC-MS, water (10 mL) was added to the reaction mixture, which was then extracted with ethyl acetate (10 mL×3). The combined organic phase was washed with water (15 mL) and saturated brine (15 mL), dried over anhydrous sodium sulfate, and filtered through a filter paper. The filtrate was concentrated by a rotary evaporator, and subjected to column chromatography (silica gel 300-400 mesh, petroleum ether:ethyl acetate=20:1) to give 4-benzylpiperidine-1-sulfonyl fluoride [compound 113] as a pale yellow solid (205 mg, 80%) (Scheme 111).

Pale yellow solid, m.p. 58-61° C., 205 mg, 80% yield: $^1$H NMR (400 MHz, CDCl$_3$) δ 7.30-7.11 (m, 5H), 3.90-3.85 (m, 2H), 2.94-2.85 (m, 2H), 2.56 (d, J=6.8 Hz, 2H), 1.75-1.62 (m, 3H), 1.35 (dq, J=4 Hz, J=11.6 Hz, 2H); $^{19}$F NMR (376 MHz, CDCl$_3$) δ 39.6 (s, 1F); LC-MS (t$_R$): 1.71 min ESI-MS (m/z): 258 [MH]$^+$.

Embodiment 112

Preparation of 4-benzylpiperidine-1-sulfonyl fluoride

Scheme 112 Preparation of 4-benzylpiperidine-1-sulfonyl fluoride

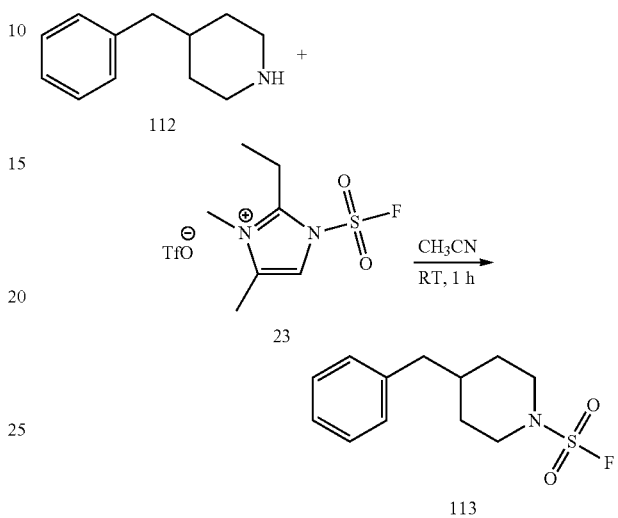

4-Benzylpiperidine [compound 112] (175 mg, 1 mmol) was dissolved in acetonitrile (2 mL) at room temperature, followed by addition of 1-(fluorosulfonyl)-2,3-dimethyl-1H-imidazolium trifluoromethanesulfonate [compound 23] (357 mg, 1 mmol). The reaction was allowed to run for 1 hour. After completion of the reaction as indicated by LC-MS, water (10 mL) was added to the reaction mixture, which was then extracted with ethyl acetate (10 mL×3). The combined organic phase was washed with water (15 mL) and saturated brine (15 mL), dried over anhydrous sodium sulfate, and filtered through a filter paper. The filtrate was concentrated by a rotary evaporator, and subjected to column chromatography (silica gel 300-400 mesh, petroleum ether:ethyl acetate=20:1) to give 4-benzylpiperidine-1-sulfonyl fluoride [compound 113] as a pale yellow solid (212 mg, 82%) (Scheme 112).

Pale yellow solid, m.p. 58-61° C., 212 mg, 82% yield; $^1$H NMR (400 MHz, CDCl$_3$) δ 7.30-7.11 (m, 5H), 3.90-3.85 (m, 2H), 2.94-2.85 (m, 2H), 2.56 (d, J=6.8 Hz, 2H), 1.75-1.62 (m, 3H), 1.35 (dq, J=4 Hz, J=11.6 Hz, 2H); $^{19}$F NMR (376 MHz, CDCl$_3$) δ 9.6 (s, 1F); LC-MS (t$_R$): 1.71 min; ESI-MS (m/z): 258 [MH]$^+$.

Embodiment 113

Preparation of 4-benzylpiperidine-1-sulfonyl fluoride

Scheme 113 Preparation of 4-benzylpiperidine-1-sulfonyl fluoride

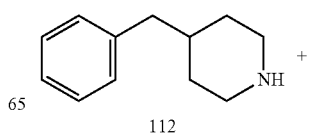

-continued

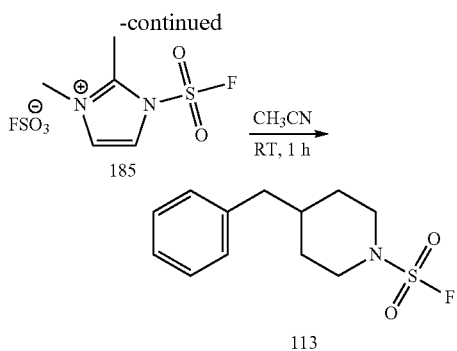

4-Benzylpiperidine [compound 112] (175 mg, 1 mmol) was dissolved in acetonitrile (2 mL) at room temperature, followed by addition of 1-(fluorosulfonyl)-2,3-dimethyl-1H-imidazolium trifluoromethanesulfonate [compound 185] (279 mg, 1 mmol). The reaction was allowed to run for 1 hour. After completion of the reaction as indicated by LC-MS, water (10 mL) was added to the reaction mixture, which was then extracted with ethyl acetate (10 mL×3). The combined organic phase was washed with water (15 mL) and saturated brine (15 mL), dried over anhydrous sodium sulfate, and filtered through a filter paper. The filtrate was concentrated by a rotary evaporator and then suctioned by an oil pump to remove the residual solvent to give 4-benzylpiperidine-1-sulfonyl fluoride [compound 113] as a pale yellow solid (252 mg, 98%) (Scheme 113).

Pale yellow solid, m.p. 58-61° C., 252 mg, 98% yield: $^1$H NMR (400 MHz, CDCl$_3$) δ 7.30-7.11 (m, 5H), 3.90-3.85 (m, 2H), 2.94-2.85 (m, 2H), 2.56 (d, J=6.8 Hz, 2H), 1.75-1.62 (m, 3H), 1.35 (dq, J=4 Hz, J=11.6 Hz, 2H); $^{19}$F NMR (376 MHz, CDCl$_3$) δ 39.6 (s, 1F); LC-MS (t$_R$): 1.71 min; ESI-MS (m/z): 258 [MH]$^+$.

Embodiment 114

Preparation of 4-benzylpiperidine-1-sulfonyl fluoride

Scheme 114 Preparation of 4-benzylpiperidine-1-sulfonyl fluoride

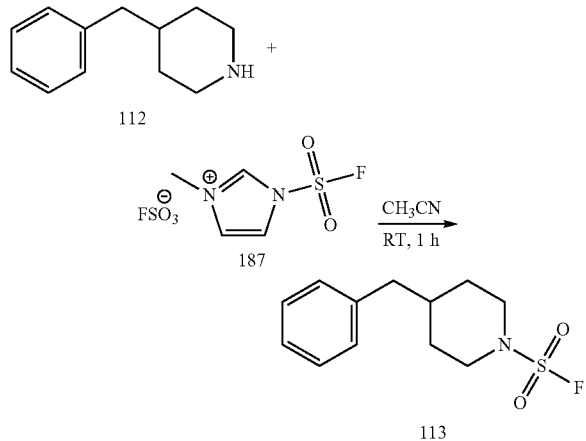

4-Benzylpiperidine [compound 112] (175 mg, 1 mmol) was dissolved in acetonitrile (2 mL) at room temperature, followed by addition of 1-(fluorosulfonyl)-2,3-dimethyl-1H-imidazolium trifluoromethanesulfonate [compound 187] (265 mg, 1 mmol). The reaction was allowed to run for 1 hour. After completion of the reaction as indicated by LC-MS, water (10 mL) was added to the reaction mixture, which was then extracted with ethyl acetate (10 mL×3). The combined organic phase was washed with water (15 mL) and saturated brine (15 mL), dried over anhydrous sodium sulfate, and filtered through a filter paper. The filtrate was concentrated by a rotary evaporator and then suctioned by an oil pump to remove the residual solvent to give 4-benzylpiperidine-1-sulfonyl fluoride [Compound 113] as a pale yellow solid (235 mg, 91%) (Scheme 114).

Pale yellow solid, m.p. 57-61° C., 235 mg, 91% yield; $^1$H NMR (400 MHz, CDCl$_3$) δ 7.30-7.11 (m 5H), 3.90-3.85 (m, 2H), 2.94-2.85 (m, 2H), 2.56 (d, J=6.8 Hz, 2H), 1.75-1.62 (m 3H), 1.35 (dq, J=4 Hz, J=11.6 Hz, 2H); $^{19}$F NMR (376 MHz, CDCl$_3$) δ 39.6 (s, 1F); LC-MS (t$_R$): 1.71 min; ESI-MS (m/z): 258 [MH]$^+$.

Embodiment 115

Preparation of 4-benzylpiperidine-1-sulfonyl fluoride

Scheme 115 Preparation of 4-benzylpiperidine-1-sulfonyl fluoride

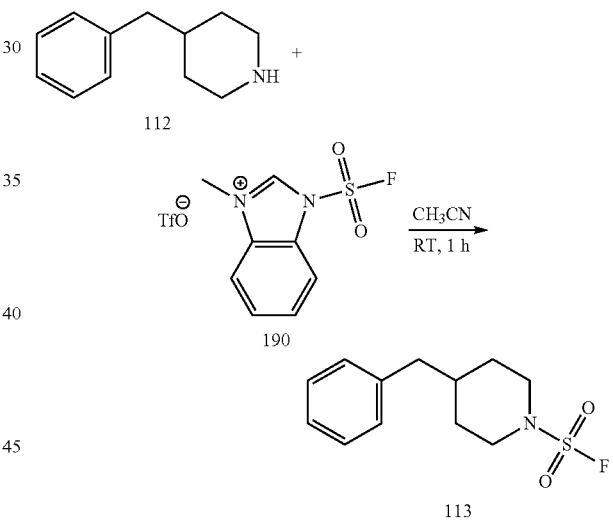

4-Benzylpiperidine [compound 112] (175 mg, 1 mmol) was dissolved in acetonitrile (2 mL) at room temperature, followed by addition of 1-(fluorosulfonyl)-2,3-dimethyl-1H-imidazolium trifluoromethane sulfonate compound [4] (329 mg, 1 mmol). The reaction was allowed to run for 1 hour. After completion of the reaction as indicated by LC-MS, water (10 mL) was added to the reaction mixture, which was then extracted with ethyl acetate (10 mL×3). The combined organic phase was washed with water (15 mL) and saturated brine (15 mL), dried over anhydrous sodium sulfate, and filtered through a filter paper. The filtrate was concentrated by a rotary evaporator, and subjected to column chromatography (silica gel 300-400 mesh, petroleum ether:ethyl acetate=9:1) to give 4-benzylpiperidine-1-sulfonyl fluoride [compound 113] as a pale yellow solid (196 mg, 76%) (Scheme 115).

Pale yellow solid, m.p. 58-61° C., 196 mg, 76% yield; $^1$H NMR (400 MHz, CDCl$_3$) δ 7.30-7.11 (m, 5H), 3.90-3.85 (m, 2H), 2.94-2.85 (m, 2H), 2.56 (d, J=6.8 Hz, 2),1.75-1.62 (m, 3H), 1.35 (dq, J=4 Hz, J=11.6 Hz, 2H); $^{19}$F NMR (376 MHz, CDCl$_3$) δ 39.6 (s, 1F); LC-MS (t$_R$): 1.71 min; ESI-MS (m/z): 258 [MH]$^+$.

Embodiment 116

Scheme 116 Preparation of N-benzylisopropylamine sulfonyl fluoride

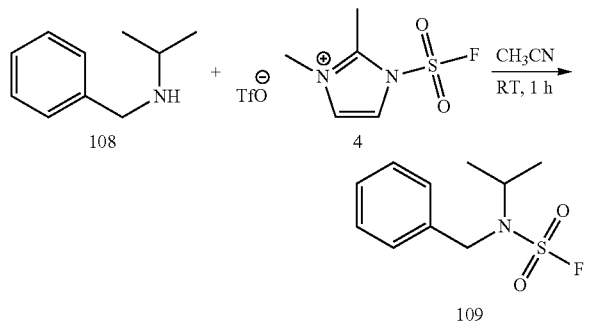

N-Benzylisopropylamine [compound 108] (149 mg, 1 mmol) was dissolved in acetonitrile (2 mL) at room temperature, followed by addition of 1-(fluorosulfonyl)-2,3-dimethyl-1H-imidazolium trifluoromethanesulfonate [compound 4] (329 mg, 1 mmol). The reaction was allowed to run for 1 hour. After completion of the reaction as indicated by LC-MS, water (10 mL) was added to the reaction mixture, which was then extracted with ethyl acetate (10 mL×3). The combined organic phase was washed with water (15 mL) and saturated brine (15 mL), dried over anhydrous sodium sulfate, and filtered through a filter paper. The filtrate was concentrated by a rotary evaporator and then suctioned by an oil pump to remove the residual solvent to give N-benzylisopropylamine sulfonyl fluoride [Compound 109](198 mg, 86%) as a yellow oil (Scheme 116).

Yellow oil, 198 mg, 86% yield; $^1$H NMR (400 MHz, CDCl$_3$) δ 7.37-7.29 (m, 5H), 4.49 (s, 2H), 4.07 (sept, J=6.8 Hz, 1H), 1.23 (d, J=6.8 Hz, 6H); $^{13}$C NMR (100 MHz, CDCl$_3$) δ 136.3 (d, J=2.2 Hz), 128.8, 128.1, 127.6, 53.5 (d, J=2.3 Hz), 49.7 (d, J=1.8 Hz), 20.6 (d, J=2.0 Hz); $^{19}$F NMR (376 MHz, CDCl$_3$) δ 50.6 (s, 1F).

Embodiment 117

Preparation of N-isopropylbenzylamine sulfonyl fluoride

Scheme 117 Preparation of N-benzylisopropylamine sulfonyl fluoride

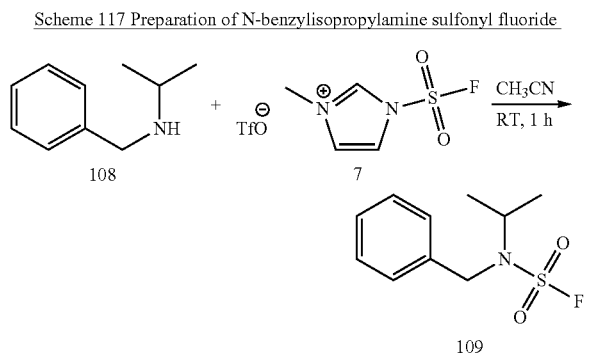

N-Benzylisopropylamine [compound 108] (149 mg, 1 mmol) was dissolved in acetonitrile (2 mL) at room temperature, followed by addition of 1-(fluorosulfonyl)-2,3-dimethyl-1H-imidazolium trifluoromethanesulfonate [compound 7] (315 mg, 1 mmol). The reaction was allowed to run for 1 hour. After completion of the reaction as indicated by LC-MS, water (10 mL) was added to the reaction mixture, which was then extracted with ethyl acetate (10 mL×3). The combined organic phase was washed with water (15 mL) and saturated brine (15 mL), dried over anhydrous sodium sulfate, and filtered through a filter paper. The filtrate was concentrated by a rotary evaporator and then suctioned by an oil pump to remove the residual solvent to give N-benzylisopropylamine sulfonyl fluoride [Compound 109] as a yellow oil (170 mg, 74%) (Scheme 117).

Yellow oil, 170 mg, 74% yield; $^1$H NMR (400 MHz, CDCl$_3$) δ 7.37-7.29 (m, 5H), 4.49 (s, 2H), 4.07 (sept, J=6.8 Hz, 1H), 1.23 (d, J=6.8 Hz, 6H); $^{19}$F NMR (376 MHz, CDCl$_3$) δ 50.6 (s, 1F).

Embodiment 118

Preparation of N-isopropylbenzylamine sulfonyl fluoride

Scheme 118 Preparation of N-benzylisopropylamine sulfonyl fluoride

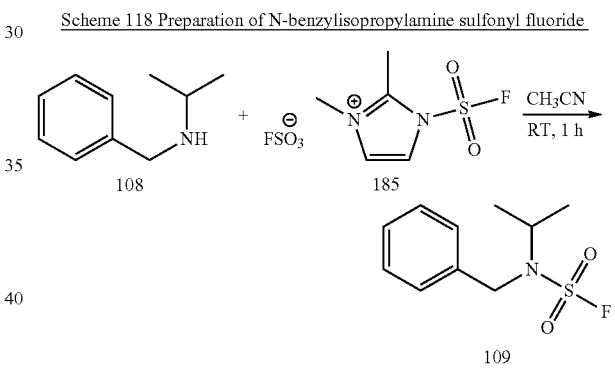

N-Benzylisopropylamine [compound 108] (149 mg, 1 mmol) was dissolved in acetonitrile (3 mL) at room temperature, followed by addition of 1-(fluorosulfonyl)-2,3-dimethyl-1H-imidazolium trifluoromethanesulfonate [compound 185] (279 mg, 1 mmol). The reaction was allowed to run for 1 hour. After completion of the reaction as indicated by LC-MS, water (10 mL) was added to the reaction mixture, which was then extracted with ethyl acetate (10 mL×3). The combined organic phase was washed with water (15 mL) and saturated brine (15 mL), dried over anhydrous sodium sulfate, and filtered through a filter paper. The filtrate was concentrated by a rotary evaporator and then suctioned by an oil pump to remove the residual solvent to give N-benzylisopropylamine sulfonyl fluoride [Compound 109] as a yellow oil (195 mg, 84%) (Scheme 118).

Yellow oil, 195 mg, 84% yield; $^1$H NMR (400 MHz, CDCl$_3$) δ7.37-7.29 (m, 5H), 4.49 (s, 2H), 4.07 (sept, J=6.8 Hz, 1H), 1.23 (d, J=6.8 Hz, 6H); $^{19}$F NMR (376 MHz, CDCl$_3$) δ 50.6 (s, 1F).

Embodiment 119

Preparation of N-isopropylbenzylamine sulfonyl fluoride

Scheme 119 Preparation of N-benzylisopropylamine sulfonyl fluoride

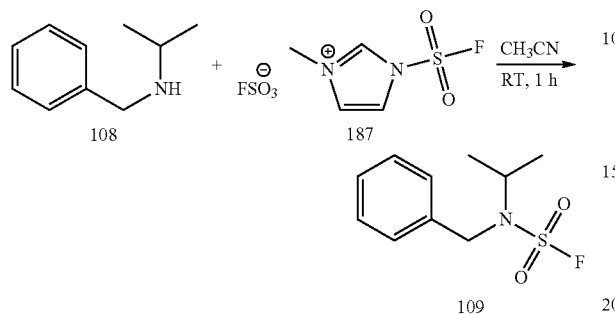

N-Benzylisopropylamine [compound 108] (149 mg, 1 mmol) was dissolved in acetonitrile (3 mL) at room temperature, followed by addition of 1-(fluorosulfonyl)-2,3-dimethyl-1H-imidazolium trifluoromethanesulfonate [compound 187] (265 mg, 1 mmol). The reaction was allowed to run for 1 hour. After completion of the reaction as indicated by LC-MS, water (10 mL) was added to the reaction mixture, which was then extracted with ethyl acetate (10 mL×3). The combined organic phase was washed with water (15 mL) and saturated brine (15 mL), dried over anhydrous sodium sulfate, and filtered through a filter paper. The filtrate was concentrated by a rotary evaporator and then suctioned by an oil pump to give N-benzylisopropylamine sulfonyl fluoride [Compound 109] as a yellow oil (186 mg, 80%) (Scheme 119).

Yellow oil, 186 mg, 80% yield; $^1$H NMR (400 MHz, CDCl$_3$) δ 7.37-7.29 (m, 5H), 4.49 (s, 2H), 4.07 (sept, J=6.8 Hz, 1H), 1.23 (d, J=6.8 Hz, 6H); $^{19}$F NMR (376 MHz, CDCl$_3$) δ 50.6 (s, 1F).

Although specific embodiments of the present disclosure have been described above, those skilled in the art should understand that these were merely for illustration, and various changes or modifications can be made to these embodiments without departing from the principle and essence of the present disclosure. Therefore, the scope of protection of the present disclosure is as defined in the appended claims.

What is claimed is:

1. A fluorosulfonyl-containing compound, wherein the compound consists of a cation and an anion, the cation is as shown in formula 1:

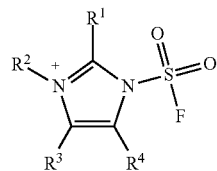

wherein each of $R^1$, $R^2$, $R^3$ and $R^4$ is independently H or C$_{1-6}$ alkyl, or $R^3$ and $R^4$ together with the carbon atoms between them form unsaturated C$_5$-C$_8$ cyclohydrocarbyl.

2. The fluorosulfonyl-containing compound as defined in claim 1, wherein
each of $R^1$ and $R^2$ is independently H or C$_{1-6}$ alkyl, $R^4$ is H, $R^3$ is H or C$_{1-6}$ alkyl, or $R^3$ and $R^4$ together with the carbon atoms between them form benzene ring.

3. The fluorosulfonyl-containing compound as defined in claim 1, wherein, when $R^1$ is C$_{1-6}$ alkyl, then the C$_{1-6}$ alkyl is C$_{1-4}$ alkyl;
and/or, when $R^2$ is C$_{1-6}$ alkyl, then the C$_{1-6}$ alkyl is C$_{1-4}$ alkyl;
and/or, when $R^3$ is C$_{1-6}$ alkyl, then the C$_{1-6}$ alkyl is C$_{1-4}$ alkyl;
and/or, when $R^4$ is C$_{1-6}$ alkyl, then the C$_{1-6}$ alkyl is C$_{1-4}$ alkyl;
and/or, when $R^3$ and $R^4$ together with the carbon atoms between them form unsaturated C$_5$-C$_8$ cyclohydrocarbyl, then the "unsaturated C$_5$-C$_8$ cyclohydrocarbyl" is benzene ring;
and/or, the anion is $^-R^5$, wherein $R^5$ is

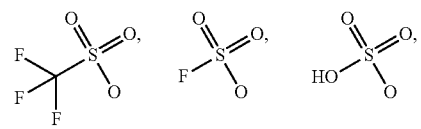 [SMILES: O=S(=O)(O)C(F)(F)F ; O=S(=O)(O)F ; O=S(=O)(O)O]

BF$_4$ or PF$_6$.

4. The fluorosulfonyl-containing compound as defined in claim 3, wherein,
when $R^1$ is C$_{1-6}$ alkyl and the C$_{1-6}$ alkyl is C$_{1-4}$ alkyl, then the C$_{1-4}$ alkyl is methyl, ethyl, isopropyl or butyl;
and/or, when $R^2$ is C$_{1-6}$ alkyl and the C$_{1-6}$ alkyl is C$_{1-4}$ alkyl, then the C$_{1-4}$ alkyl is methyl or butyl;
and/or, when $R^3$ is C$_{1-6}$ alkyl and the C$_{1-6}$ alkyl is C$_{1-4}$ alkyl, then the C$_{1-4}$ alkyl is methyl or butyl;
and/or, when $R^4$ is C$_{1-6}$ alkyl and the C$_{1-6}$ alkyl is C$_{1-4}$ alkyl, then the C$_{1-4}$ alkyl is methyl or butyl;
and/or, the anion is $^-R^5$, and $R^5$ is

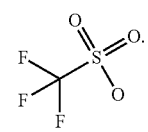

5. The fluorosulfonyl-containing compound as defined in claim 4, wherein, when $R^1$ is C$_{1-6}$ alkyl and the C$_{1-6}$ alkyl is butyl, then the butyl is n-butyl.

6. The fluorosulfonyl-containing compound as defined in claim 1, wherein, the cation is

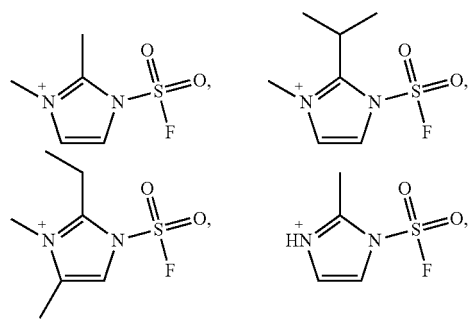

-continued

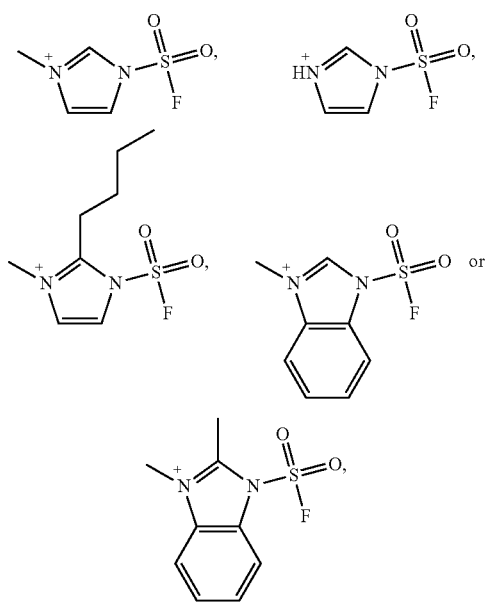

7. The fluorosulfonyl-containing compound as defined in claim 1, wherein the fluorosulfonyl-containing compound is selected from the group consisting of:

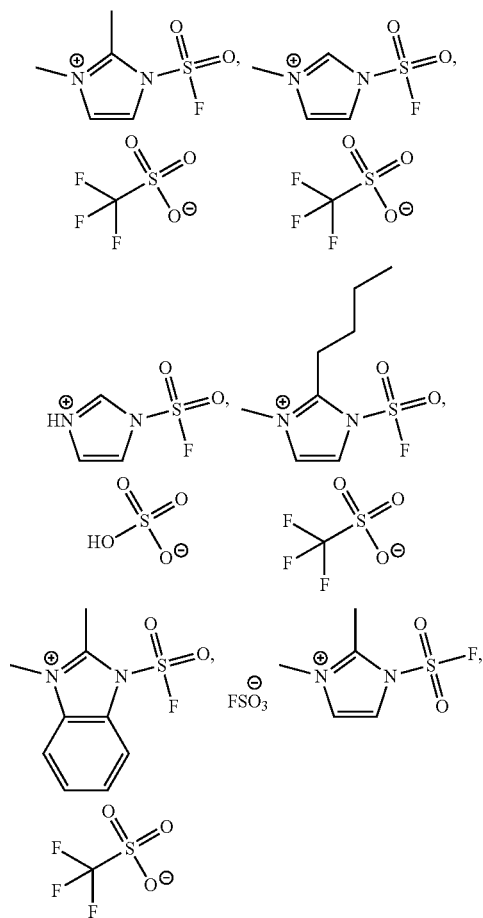

-continued

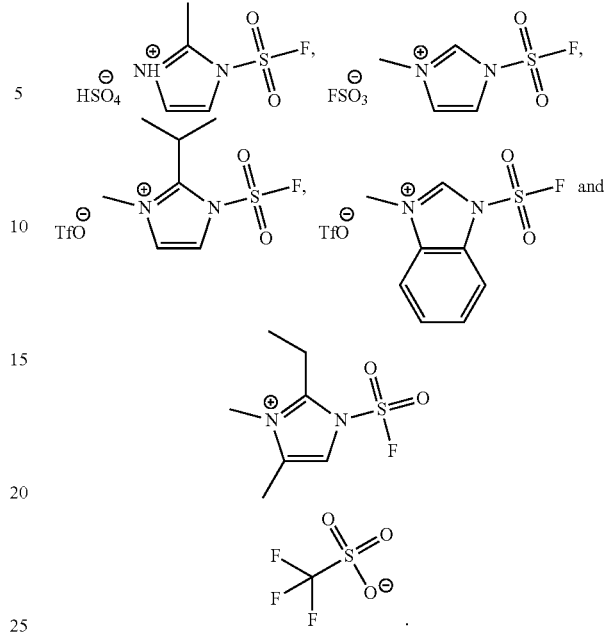

8. A method for preparing the fluorosulfonyl-containing compound as defined in claim 1, wherein the method comprises
reacting

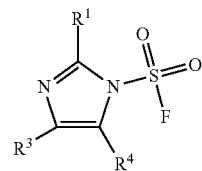

with "$R^2$-anion" in a first organic solvent.

9. The method for preparing the fluorosulfonyl-containing compound as defined in claim 8, wherein,
in the structure of the "$R^2$-anion", the anion is actually formed by $R^5$; in the reaction, $R^2$ is linked to the N in the compound represented by formula 2, forming the cation represented by formula 1; and $R^5$ forms the anion $^-R^5$;
and/or, the first organic solvent is one or more selected from the group consisting of acetonitrile, dichloromethane, diethyl ether, tetrahydrofuran, 1,2-dichloroethane, dimethyl sulfoxide, N,N-dimethylformamide, methyl tert-butyl ether and chloroform;
and/or, the reaction is performed at $(-15)°$ C.-20° C.

10. The method for preparing the fluorosulfonyl-containing compound as defined in claim 8, wherein the method further comprises: reacting

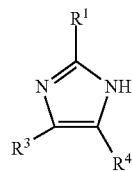

with sulfuryl fluoride in the presence of a base in a second organic solvent to give

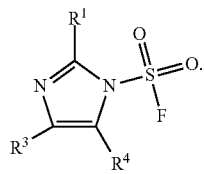

11. The method for preparing the fluorosulfonyl-containing compound as defined in claim 10, wherein,
the second organic solvent is one or more selected from the group consisting of acetonitrile, dichloromethane, ethyl acetate, benzene, toluene, acetone, 1,4-dioxane, diethyl ether, tetrahydrofuran, 1,2-dichloroethane, dimethyl sulfoxide, N,N-dimethylformamide, N-methylpyrrolidone, methyl tert-butyl ether and chloroform;
and/or, the base includes an inorganic base and/or an organic base;
and/or, the reaction is performed at (−20)° C.-35° C.

12. The method for preparing the fluorosulfonyl-containing compound as defined in claim 11, wherein,
the inorganic base is one or more selected from the group consisting of sodium carbonate, potassium carbonate, cesium carbonate, sodium hydroxide, potassium hydroxide, sodium bicarbonate and potassium bicarbonate; the organic base is one or more selected from the group consisting of triethylamine, N,N-diisopropylethylamine, pyrrole and pyridine;
and/or, the reaction is performed at 5° C.-30° C.

13. A method for converting phenolic hydroxyl and/or amino to fluorosulfonyl, wherein the method comprises reacting a substrate with the fluorosulfonyl-containing compound as defined in claim 1;
wherein the substrate is a phenolic hydroxyl-containing compound, a primary amine or a secondary amine.

14. The method as defined in claim 13, wherein the number of the phenolic hydroxyl in the phenolic hydroxyl-containing compound is one, two or three.

15. The method as defined in claim 13, wherein,
when the substrate is a phenolic hydroxyl-containing compound, then the product obtained by the reaction is selected from the group consisting of:

33

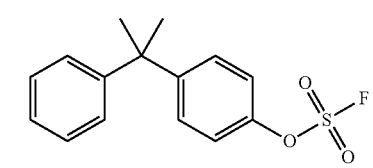

35

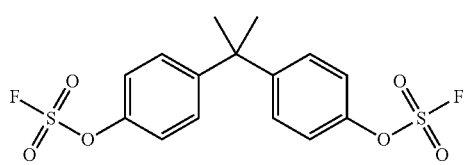

37

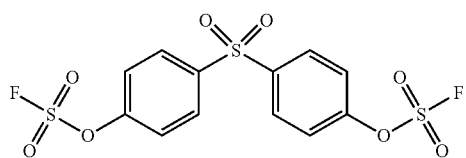

39

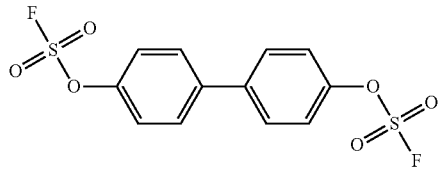

41

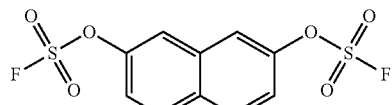

43

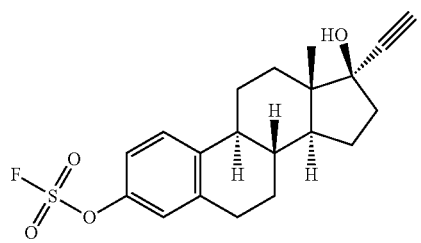

45

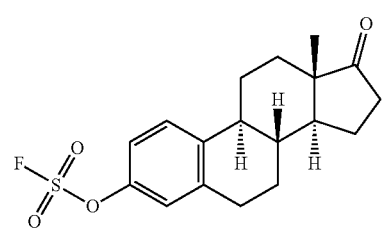

47

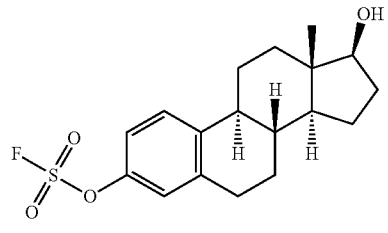

49

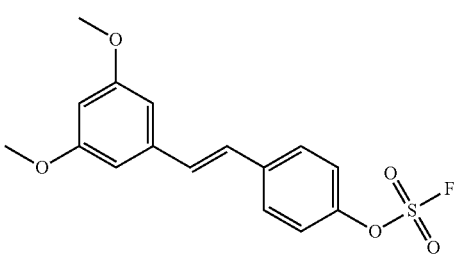

51

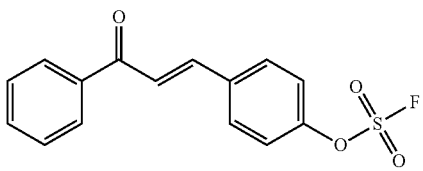

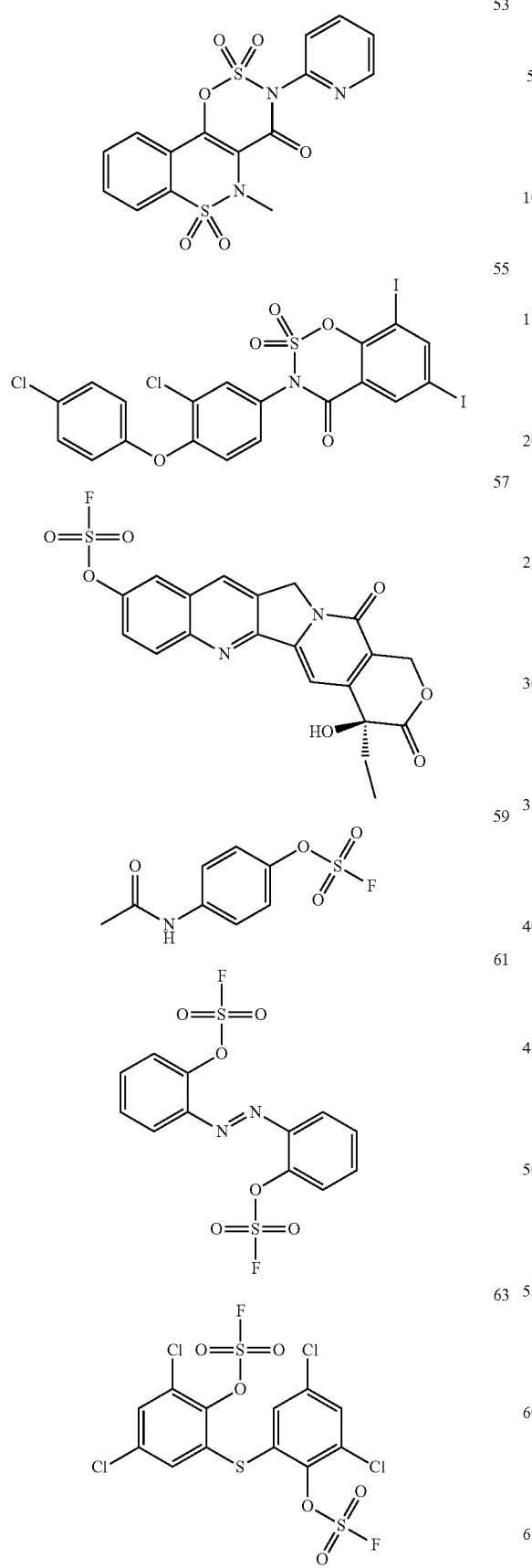

79
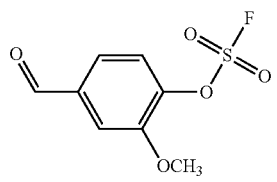
81
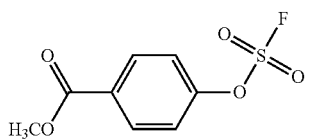
83
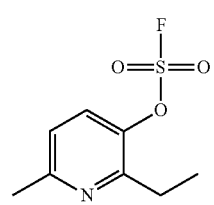
85
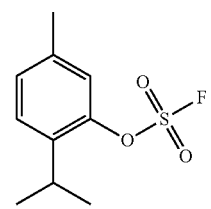
87
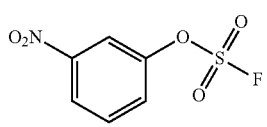
89
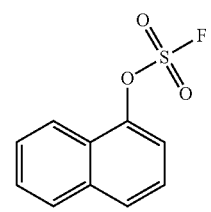
91-1
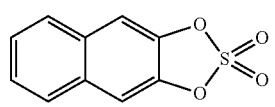
91-2
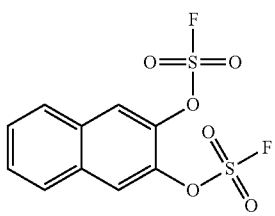
93
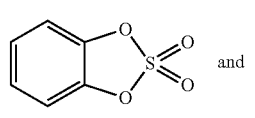 and
95
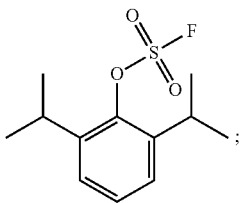
and/or, when the substrate is a primary amine, then the product obtained by the reaction is selected from the group consisting of:
136
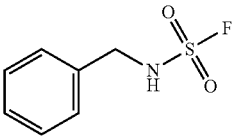
138
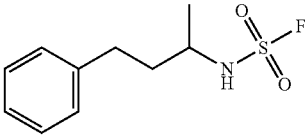
140
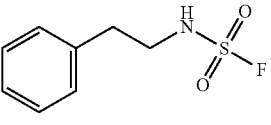
142
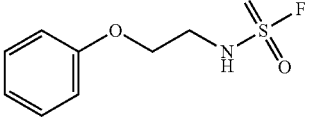
144
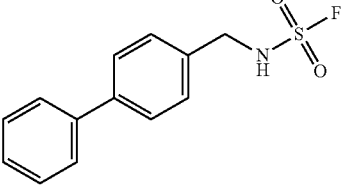
146
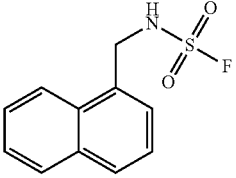
148
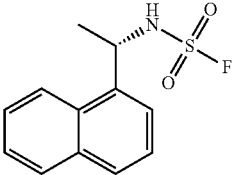

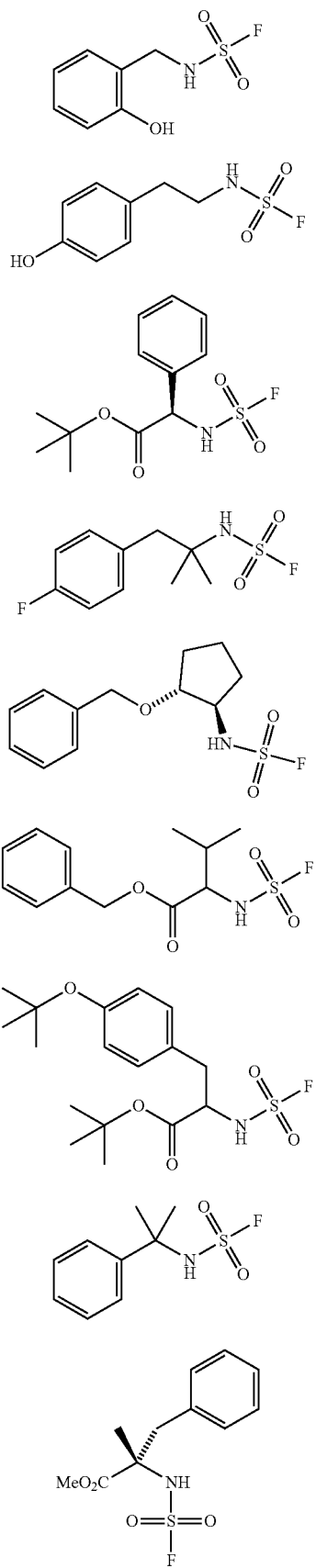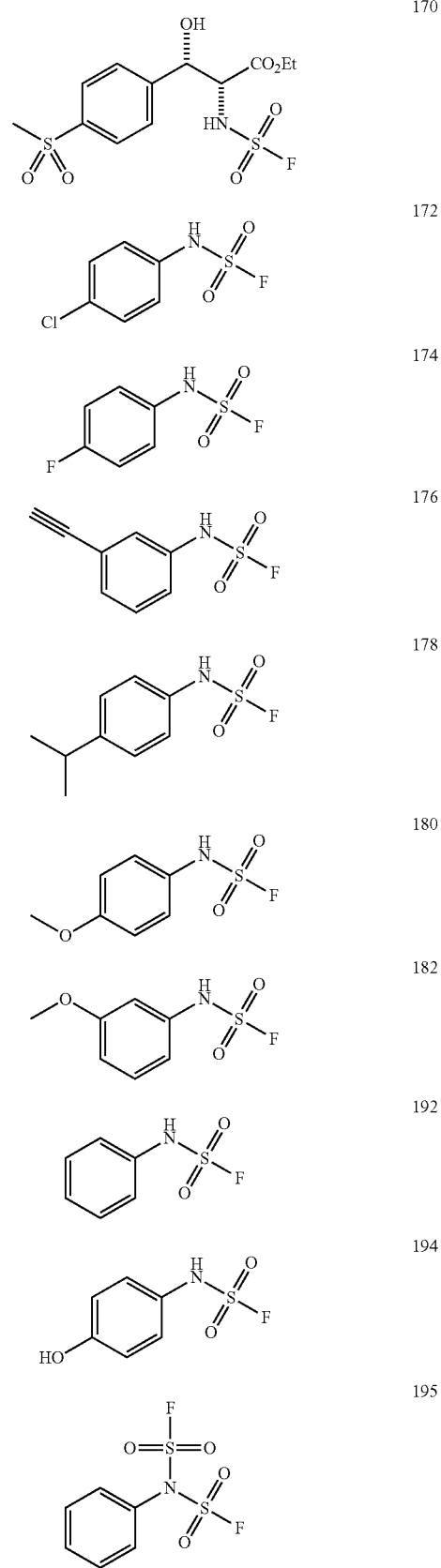

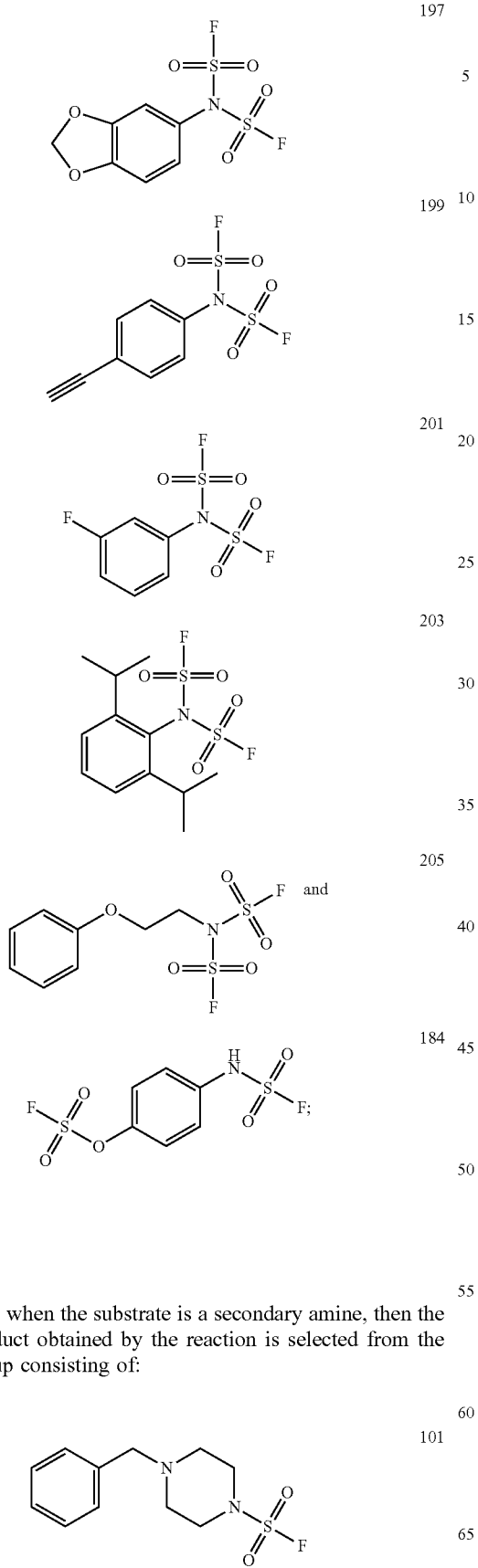
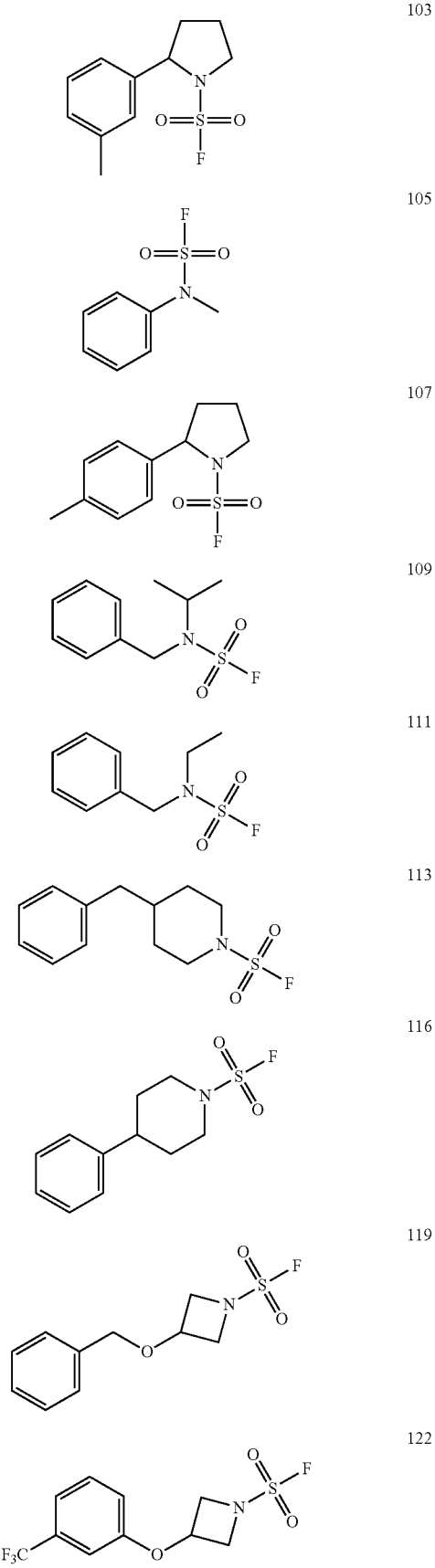
and/or, when the substrate is a secondary amine, then the product obtained by the reaction is selected from the group consisting of:

-continued

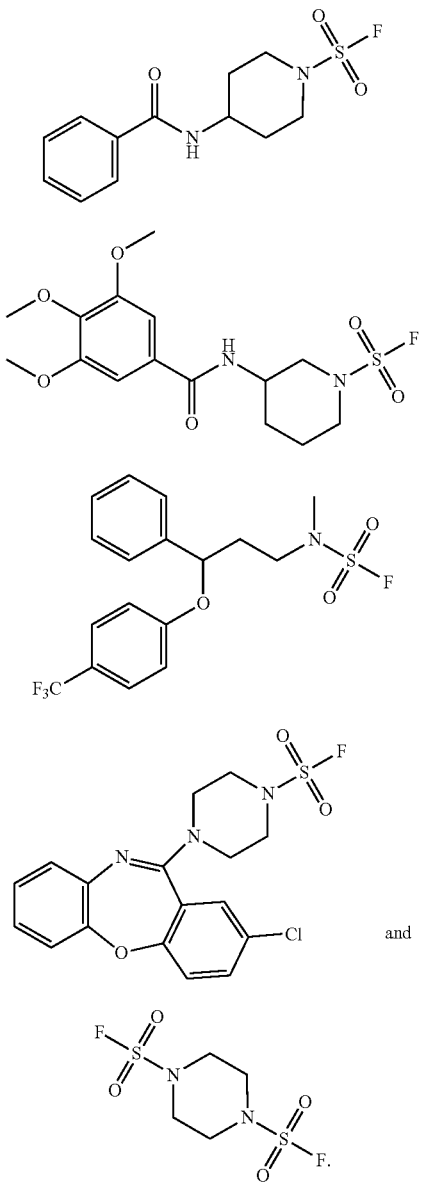

16. The method as defined in claim 13, wherein,
the reaction is carried out at 0-35° C.;
and/or, the time of the reaction is 5 min-6 h;
and/or, the reaction is carried out in an organic solvent, and the organic solvent is acetonitrile, dichloromethane or ethyl acetate.

17. A compound represented by formula 2:

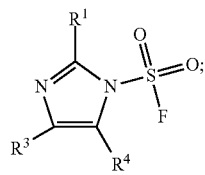

wherein $R^1$ is $C_{1-6}$ alkyl, $R^3$ and $R^4$ are as defined in claim 1.

18. The fluorosulfonyl-containing compound as defined in claim 1, wherein the cation is

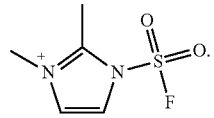

19. The method for preparing the fluorosulfonyl-containing compound as defined in claim 9, wherein the first organic solvent is methyl tert-butyl ether;
and/or, the reaction is performed at 0° C.

20. The method for preparing the fluorosulfonyl-containing compound as defined in claim 11, wherein the second organic solvent is acetonitrile.

* * * * *